(12) United States Patent
Okamoto et al.

(10) Patent No.: US 8,383,792 B2
(45) Date of Patent: *Feb. 26, 2013

(54) COMPOUND HAVING STRUCTURE DERIVED FROM MONONUCLEOSIDE OR MONONUCLEOTIDE, NUCLEIC ACID, LABELING SUBSTANCE, AND METHOD AND KIT FOR DETECTION OF NUCLEIC ACID

(75) Inventors: Akimitsu Okamoto, Wako (JP); Shuji Ikeda, Wako (JP); Takeshi Kubota, Wako (JP)

(73) Assignee: Riken, Saitama (JP)

( * ) Notice: Subject to any disclaimer, the term of this patent is extended or adjusted under 35 U.S.C. 154(b) by 479 days.

This patent is subject to a terminal disclaimer.

(21) Appl. No.: 12/530,574

(22) PCT Filed: Mar. 6, 2008

(86) PCT No.: PCT/JP2008/054054
§ 371 (c)(1),
(2), (4) Date: Sep. 9, 2009

(87) PCT Pub. No.: WO2008/111485
PCT Pub. Date: Sep. 18, 2008

(65) Prior Publication Data
US 2010/0092971 A1 Apr. 15, 2010

(30) Foreign Application Priority Data

Mar. 9, 2007 (JP) ................. 2007-059921
Sep. 21, 2007 (JP) ................. 2007-246253
Dec. 26, 2007 (JP) ................. 2007-335352

(51) Int. Cl.
*C07H 21/00* (2006.01)
*C07H 21/02* (2006.01)
*C12Q 1/68* (2006.01)

(52) U.S. Cl. ...... 536/23.1; 536/4.1; 536/24.3; 536/26.6; 435/6.1

(58) Field of Classification Search .............. 536/4.1, 536/23.1, 24.3, 26.6; 435/6
See application file for complete search history.

(56) References Cited

U.S. PATENT DOCUMENTS

| 5,547,860 | A | 8/1996 | Kocher et al. |
| 8,067,162 | B2 * | 11/2011 | Hayashizaki et al. ....... 435/6.12 |
| 2002/0192670 | A1 | 12/2002 | Tokunaga et al. |
| 2007/0048773 | A1 | 3/2007 | Lee et al. |
| 2008/0227104 | A1 | 9/2008 | Hayashizaki et al. |

FOREIGN PATENT DOCUMENTS

| EP | 0 527 433 | 2/1993 |
| EP | 0 608 737 | 8/1994 |
| EP | 1 712 618 | 10/2006 |
| JP | 6-271599 | 9/1994 |
| JP | 11-127862 | 5/1999 |
| JP | 2002-327130 | 11/2002 |
| JP | 2004-081057 | 3/2004 |
| JP | 2004-529618 | 9/2004 |
| JP | 2005-518819 | 6/2005 |
| JP | 2006-320267 | 11/2006 |
| WO | 98/58942 | 12/1998 |
| WO | 02/061121 | 8/2002 |
| WO | 03/076566 | 9/2003 |
| WO | 2003/344290 | 12/2003 |
| WO | 2004/074503 | 9/2004 |
| WO | 2006/097320 | 9/2006 |

OTHER PUBLICATIONS

Office Action issued for the corresponding Japanese Application No. 2009-504009, dated Nov. 4, 2010 with its partial English translation (4 pages).

Tainaka et al, "Development of novel base-discriminating fluorescent probes containing polarity-sensitive chromophore", Lecture Summary of Photochemistry Forum, vol. 2006, p. 560, 2006 with English translation (4 pages).

Kodate et al, "New Interpretation for Dual Fluorescence Mechanism of Pyrene Type DNA Fluorescence Probe", Lecture Summary of Photochemistry Forum, vol. 2006, p. 385, 2006 with English translation (3 pages).

Imae, T. et al, "Interaction between acridine orange and polyriboadenylic acid", International Journal of Biological Macromolecules, vol. 3, No. 4, p. 259-266, 1981 (8 pages).

Office Action of the related European Patent Application No. 08004171.8 dated May 12, 2010—5 pages.
Telser, et al., "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements", J. Am. Chem. Soc., vol. 111, 1989, pp. 6966-6976.
Supplementary European Search Report of the corresponding European Patent Application No. 08721474.8 dated May 18, 2010—14 pages.
Kasha, "Energy Transfer Mechanisms and Molecular the Exciton Model for Molecular Aggregates", Radiation Research, vol. 20, pp. 55-70, 1963.
Kasha, et al., "The Exciton Model in Molecular Spectroscopy", Pure Appl. Chem., vol. 11, , pp. 371-392, 1965.
Tyagi, et al., "Molecular Beacons: Probes that Fluoresce Upon Hybridization", Nature Biotechnology, vol. 14, pp. 303-308, Mar. 1996.
Nazarenko, et al., "A closed tube format for amplification and detection of DNA based on energy transfer", Nucleic Acids Research, vol. 25, No. 12, pp. 2516-2521, 1997.
Gelmini, et al., "Quantitative polymerase chain reaction-based homogeneous assay with fluorogenic probes to measure c-$erb$B-2 oncogene amplification", Clinical Chemistry, vol. 43, No. 5, pp. 752-758, 1997.
Whitcombe, et al., "Detection of PCR products using self-probing amplicons and fluorescence", Nature Biotechnology, vol. 17, pp. 804-807, 1999.
Nygren, et al., "The Interactions Between the Fluorescent Dye Thiazole Orange and DNA", Biopolymers, vol. 46, pp. 39-51, 1998.
Wang, et al., "Tethered thiazole orange intercalating dye for development of fibre-optic nucleic acid biosensors", Analytica Chimica Acta vol. 470, pp. 57-70, 2002.
Lartia, et al., "New Cyanine-Oligonucleotide Conjugates: Relationships between Chemical Structures and Properties", Chemistry—A European Journal, vol. 12, pp. 2270-2281, 2006.
Mitani, et al., "Rapid SNP diagnostics using asymmetric isothermal amplification and a new mismatch-suppression technology", Nature Methods, vol. 4, No. 3, pp. 257-262, 2007.
Ikeda, et al., Novel Fluorescent probes for detection of nucleic acids , Book of Abstracts for the Annual Meeting on Photochemistry, p. 182, Sep. 21, 2007.
Written Opinion of the International Searching Authority of PCT/JP2008/054054 dated May 20, 2008 with its partial translation—5 pages.
International Search Report of PCT/JP2008/054054 dated May 20, 2008—4 pages.
Partial European Search Report of the relative EP application No. 08004171.8, dated Jun. 18, 2008—8 pages.
Mitsui, et al., "Characterization of fluorescent, unnatural base pairs", Tetrahedron, vol. 63, Issue 17, pp. 3528-3537, 2007.
Office Action of the relative JP Application No. 2008-035325 dated Oct. 14, 2008 with its partial translation—7 pages.
Hwang, et al., "Fluorescent oligonucleotide incorporating 5-(1-ethynylpyrenyl)-2'-deoxyuridine: sequence-specific fluorescence changes upon duplex formation", Tetrahedron Letters, vol. 45, Issue 18, pp. 3543-3546, 2004.
Okamoto, et al., "Synthesis and ESR studies of nitronyl nitroxide-tethered oligodeoxynucleotides", Tetrahedron Letters, vol. 46, Issue 5, pp. 791-795, 2005.
Jarikote, et al., "Divergent and Linear Solid-Phase Synthesis of PNA Containing Thiazole Orange as Artificial Base", European Journal of Organic Chemistry, No. 15, pp. 3187-3195, 2005.
Bordelon, et al., "Viscometry and Atomic Force Microscopy Studies of the Interactions of a Dimeric Cyanine Dye with DNA", The Journal of Physical Chemistry B., vol. 106, pp. 4838-4843, 2002.
Inoue, et al., "Fluorescence Property of Oxazole Yellow-linked Oligonucleotide. Triple Helix Formation and Photocleavage of Duble-stranded DNA in the Presence of Spermine", Bioorganic and Medicinal Chemistry, vol. 7, No. 6, pp. 1207-1211, 1999.
Office Action of the relative JP Application No. 2008-035325 dated Jan. 26, 2009 with its partial translation—6 pages.
Office Action of the relative EP application No. 08004171.8 dated Jun. 2, 2009—4 pages.
Okamoto, et al., "Pyrene-Labeled Oligodeoxynucleotide Probe for Detecting Base Insertion by Excimer Fluorescene Emission", Journal of the American Chemical Society, vol. 126, No. 27, pp. 8364-8365, 2004.
Fïstenberg, et al., "Ultrafast Excited-State Dynamics of DNA Fluorescent Intercalators: New Insight into the Fluorescence Enhancement Mechanism", Journal of the American Chemical Society, vol. 128, No. 23, pp. 7661-7669, 2006.
Stratagene, Catalog, 1988, p. 39.

* cited by examiner

*Primary Examiner* — Jezia Riley
(74) *Attorney, Agent, or Firm* — Hamre, Schumann, Mueller & Larson, P.C.

(57) ABSTRACT

The present invention provides, for example, a labeling substance that allows the double helix structure of a nucleic acid to be detected effectively. The present invention provides a compound having a structure derived from mononucleoside or mononucleotide, with the structure being represented by the following formula (1), (1b), or (1c), a tautomer or stereoisomer thereof, or a salt thereof.

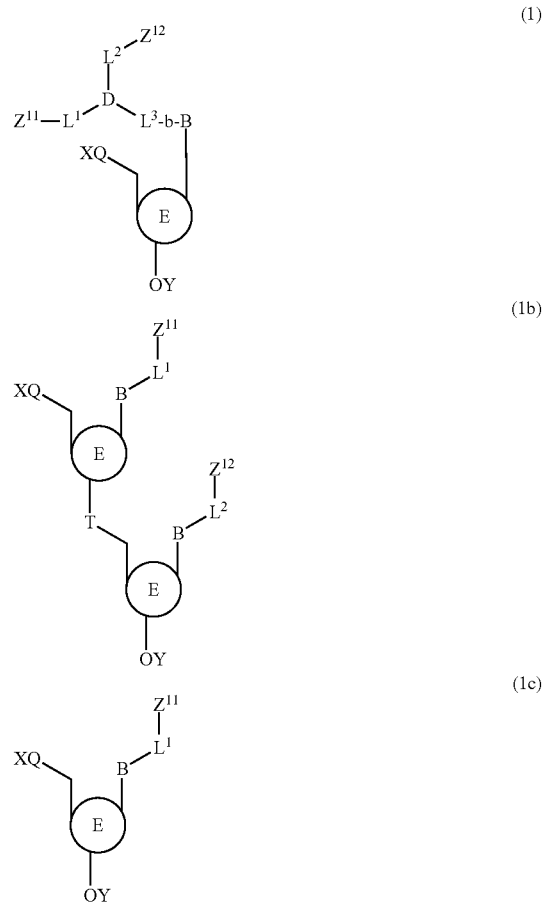

In the above formulae, B is an atomic group having a nucleobase skeleton, E is an atomic group having a deoxyribose skeleton, a ribose skeleton, or a structure derived from either one of them, or an atomic group having a peptide structure or a peptoid structure, and $Z^{11}$ and $Z^{12}$ each are a hydrogen atom, a protecting group, or an atomic group that exhibits fluorescence and may be identical to or different from each other.

21 Claims, 30 Drawing Sheets

¹H NMR spectrum

¹³C NMR spectrum

¹H NMR spectrum

¹³C NMR spectrum (a) Spots of 4.5S  ◯ ◯ ◯ ◯

Spots of B1  ◯ ◯ ◯ ◯

(b)

(c)

COMPOUND HAVING STRUCTURE DERIVED FROM MONONUCLEOSIDE OR MONONUCLEOTIDE, NUCLEIC ACID, LABELING SUBSTANCE, AND METHOD AND KIT FOR DETECTION OF NUCLEIC ACID

TECHNICAL FIELD

The present invention relates to a compound having a structure derived from mononucleoside or mononucleotide, a nucleic acid, a labeling substance, and a method and a kit for detecting a nucleic acid.

BACKGROUND ART

In, for example, genetic diagnoses of diseases and gene expression analysis, it is necessary to detect a nucleic acid having a specific sequence. For the detection, methods utilizing fluorescence are used widely, and for instance, a fluorescence probe obtained by covalently bonding one type of fluorescent dye to DNA often is used as a labeling substance.

Such a labeling substance (a fluorescence probe) has a problem in that, for example, it emits fluorescence even when it has not formed a double helix with a complementary nucleic acid. For the purpose of quenching fluorescence of only the probe, the method using fluorescence resonance energy transfer (FRET) is effective (e.g., Non-Patent Documents 1 to 4). However, it has problems in, for example, cost due to the introduction of two types of fluorescent dyes.

Thiazole orange, which is one type of cyanine dye, is known as a fluorescent dye whose fluorescence intensity increases through an interaction with DNA or RNA. There are examples in which a fluorescent probe was intended to be produced with thiazole orange being bonded to DNA by a covalent bond. However, it also emits strong fluorescence through an interaction with a single-stranded DNA containing a purine base (Non-Patent Document 5). Accordingly, the increase in fluorescence intensity obtained when a double helix is formed is small, and therefore it cannot be considered as being successful (Non-Patent Documents 6 and 7).

Non-Patent Document 1: Tyagi, S., Kramer, F. R. (1996) Nat. Biotechnol. 14, 303-308.
Non-Patent Document 2: Nazarenko, I. A., Bhatnagar, S. K., Hohman, R. J. (1997) Nucleic Acids Res. 25, 2516-2521.
Non-Patent Document 3: Gelmini, S., Orlando, C., Sestini, R., Vona, G., Pinzani, P., Ruocco, L., Pazzagli, M. (1997) Clin. Chem. 43, 752-758.
Non-Patent Document 4: Whitcombe, D., Theaker, J., Guy, S. P., Brown, T.,
Little, S. (1999) Nat. Biotechnol. 17, 804-807.
Non-Patent Document 5: Biopolymers 1998, 46, 39-51.
Non-Patent Document 6: Analytica Chimica Acta 2002, 470, 57-70.
Non-Patent Document 7: Chemistry—A European Journal 2006, 12, 2270-2281.

DISCLOSURE OF INVENTION

Hence, the present invention is intended to provide, for example, a labeling substance that allows the double helix structure of a nucleic acid to be detected effectively.

In order to solve the foregoing problems, the present invention provides a compound having a structure derived from mononucleoside or mononucleotide, with the structure being represented by the following formula (1), (1b), or (1c), a tautomer or stereoisomer thereof, or a salt thereof.

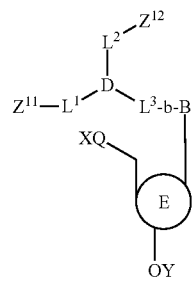

(1)

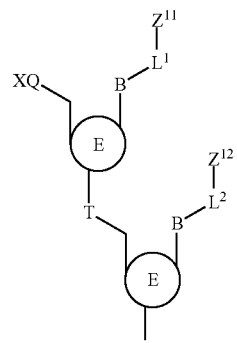

(1b)

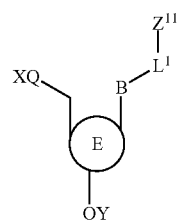

(1c)

In the formulae (1), (1b), and (1c),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each a hydrogen atom, a protecting group, or an atomic group that exhibits fluorescence, and may be identical to or different from each other, Q is:
O, when E is an atomic group described in item (i), or
NH, when E is an atomic group described in item (ii), X is:
a hydrogen atom, a protecting group of a hydroxy group that can be deprotected with acid, a phosphate group (a monophosphate group), a diphosphate group, or a triphosphate group, when E is an atomic group described in item (i) or
a hydrogen atom or a protecting group of an amino group, when E is an atomic group described in item (ii), Y is:
a hydrogen atom, a protecting group of a hydroxy group, or a phosphoramidite group, when E is an atomic group described in item (i), or
a hydrogen atom or a protecting group, when E is an atomic group described in item (ii), $L^1$, $L^2$, and $L^3$ are each a linker (a linking atom or an atomic group), the main chain length (the number of main chain atoms) is arbitrary. They each may or may not contain each of C, N, O, S, P, and Si in the main chain, they each may or may not contain each of a single bond, a double bond, a triple bond, an amide bond, an ester bond, a disulfide bond, an imino group, an ether bond, a thioether bond, and a thioester bond in the main chain. $L^1$, $L^2$, and $L^3$ may be identical to or different from one another, D is CR, N, P, P=O, B, or SiR, and R is a hydrogen atom, an alkyl group, or an arbitrary substituent, b is a single bond, a double bond, or a triple bond, or in the formula (1), $L^1$ and $L^2$ are each the aforementioned linker, $L^3$, D, and b may not be present, and $L^1$ and $L^2$ may be bonded directly to B, in the formula (1b), T is a phosphoric acid linkage ($PO_4^-$) in which at least one oxygen atom (O) may be substituted with a sulfur atom (S), when E is an atomic group described in item (i), or NH, when E is an atomic group described in item (ii).

Furthermore, a nucleic acid of the present invention is a nucleic acid including at least one of structures represented by the following formulae (16), (16b), (17), (17b), (18), and (18b), a tautomer or stereoisomer thereof, or a salt thereof. Note here that, in the present specification, in chemical formulae (e.g., the following formulae (16), (16b), (17), (17b), (18), and (18b)), when a bond extends from the inside toward the outside of parentheses and the bond is marked with a star outside of the parentheses, the star means that some atom or atomic group binds to the bond.

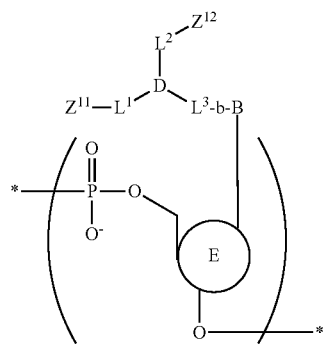

In the formulae (16), (16b), (17), (17b), (18), and (18b),

B, E, $Z^{11}$, $Z^{12}$, $L^1$, $L^2$, $L^3$, D, and b each have the same structure as that of the formula (1), (1b), or (1c), where in the formulae (16), (17), and (18), E is an atomic group described in item (i) in the formula (1), (1b), or (1c), and at least one O atom in a phosphoric acid linkage may be substituted with an S atom, in the formulae (16b), (17b), and (18b), E is an atomic group described in item (ii) in the formula (1), (1b), or (1c), and in the formulae (17) and (17b), the respective Bs may be identical to or different from each other, and the respective Es may be identical to or different from each other.

Furthermore, a labeling substance of the present invention is:

(i) a labeling substance that emits fluorescence, with two planar chemical structures contained in one molecule, which exist not in the same plane but with a certain angle formed therebetween, being located so as to be arranged in the same plane when the molecule undergoes intercalation into or groove binding to a nucleic acid, (ii) a labeling substance formed of at least two dye molecule groups that do not exhibit fluorescence emission due to the exciton effect obtained when at least two dye molecules aggregate in parallel to each other but exhibit fluorescence emission with the aggregation state being resolved when the molecules undergo intercalation into or groove binding to a nucleic acid, or (iii) a complex labeling substance having, as a characteristic chemical structure, a chemical structure of at least two dye molecules contained in one molecule, with the at least two dye molecules not exhibiting fluorescence emission due to the exciton effect obtained when they aggregate in parallel to each other but exhibiting fluorescence emission with the aggregation state being resolved when the molecules undergo intercalation into or groove binding to nucleic acid.

Furthermore, a method of detecting a nucleic acid of the present invention is:

(I) a method of detecting a nucleic acid, comprising the steps of: carrying out nucleic acid synthesis using, as a substrate, the labeling substance according to the present invention that is labeled mononucleotide or labeled oligonucleotide, thereby synthesizing a double-stranded nucleic acid to which the atomic group that exhibits fluorescence or the dye molecule structure is bonded by intercalation or groove binding;

measuring fluorescence intensity before and after the step of synthesizing the double-stranded nucleic acid; and detecting the nucleic acid synthesis by comparing the fluorescence intensities to each other that are obtained before and after the step of synthesizing the double-stranded nucleic acid, (II) a method of detecting a nucleic acid, comprising the steps of: carrying out nucleic acid synthesis by hybridizing, as a first nucleic acid, the labeling substance according to the present invention that is a single-stranded nucleic acid to a second nucleic acid having a sequence complementary to the first nucleic acid or a sequence analogous to the complementary sequence, thereby synthesizing a double-stranded nucleic acid to which the atomic group that exhibits fluorescence or the dye molecule structure is bonded by intercalation or groove binding;

measuring fluorescence intensity before and after the step of synthesizing the double-stranded nucleic acid; and detecting the hybridization between the first nucleic acid and the second nucleic acid by comparing the fluorescence intensities to each other that are obtained before and after the step of synthesizing the double-stranded nucleic acid; or (III) a method of detecting a nucleic acid, which detects formation of a triple-stranded nucleic acid or a nucleic acid analog by using a third nucleic acid that has a sequence of the aforementioned first nucleic acid or the second nucleic acid, a sequence complementary to the sequence of the first nucleic acid or the second nucleic acid, or a sequence analogous to the complementary sequence, and is labeled or not labeled with the labeling substance according to the present invention or a complex labeling substance.

Still further, a kit of the present invention includes: a nucleic acid synthesis unit, a labeling substance, and a fluorescence intensity measurement unit, wherein the labeling substance is the aforementioned labeling substance of the present invention.

By having the aforementioned structure, the compound and nucleic acid of the present invention can be used, for example, as a labeling substance that allows the double helix structure of a nucleic acid to be detected effectively. More specifically, the compound or nucleic acid with a structure represented by the formula (1), (1b), (1c), (16), (16b), (17), (17b), (18), or (18b) where $Z^{11}$ and $Z^{12}$ each are an atomic group that exhibits fluorescence, for example, is suitable as the labeling substance of the present invention. Furthermore, the compound or nucleic acid wherein $Z^{11}$ and $Z^{12}$ are each a hydrogen atom or a protecting group can be used as a raw material for synthesizing the labeling substance or a synthetic intermediate thereof. It is to be noted, however, use of the compound and nucleic acid of the present invention is not limited thereto, and they can be used for any applications.

DESCRIPTION OF THE INVENTION

Figure 1:
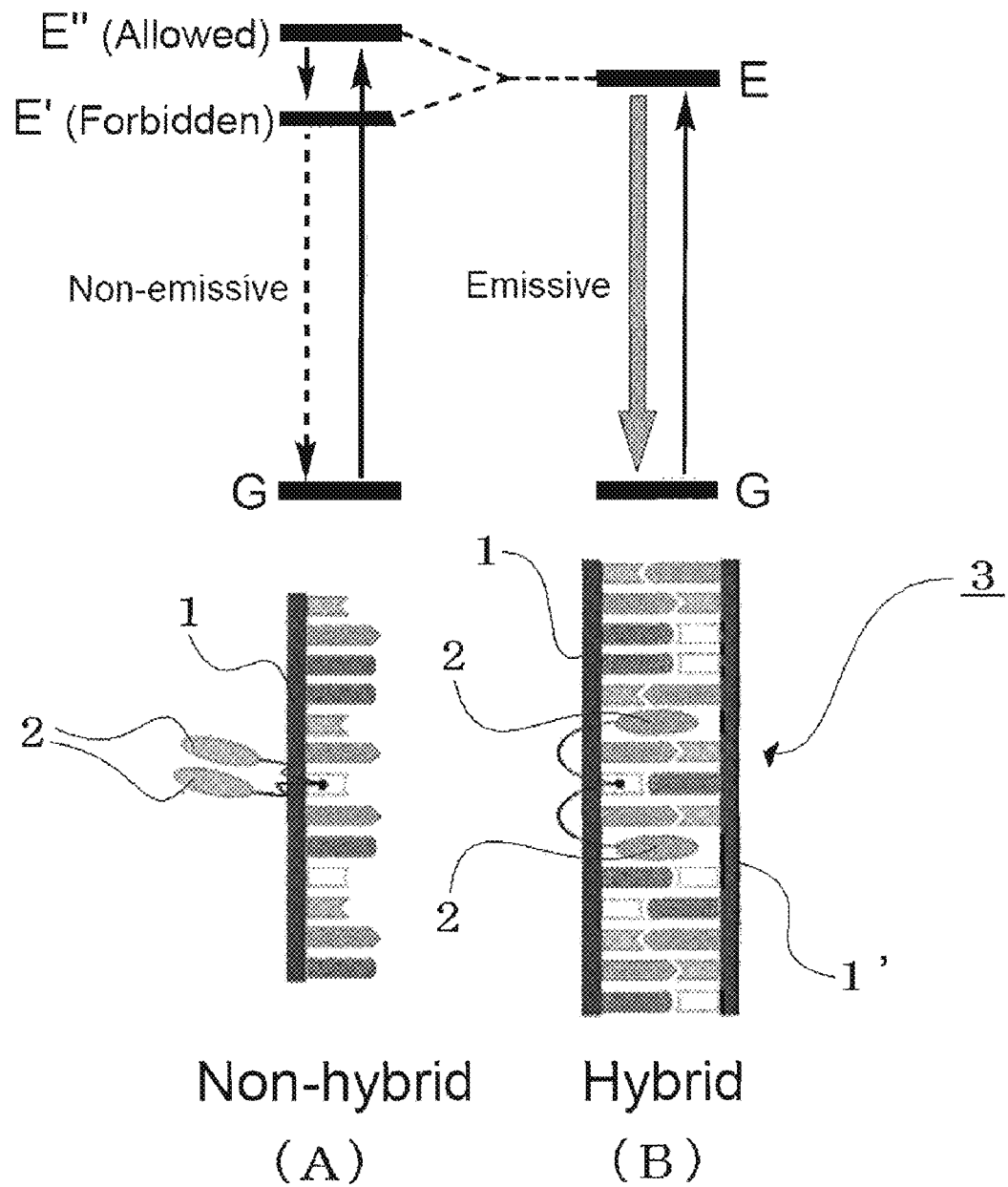
FIG. 1 is a diagram that schematically shows the principle of the present invention.

Next, embodiments of the present invention are described in further detail.

[Compound, Nucleic Acid, and Labeling Substance of the Present Invention]

The compound and nucleic acid of the present invention are not particularly limited, except that they are represented by the chemical formulae shown above. As described above, the use thereof also is not particularly limited, and they can be used, for example, as the aforementioned labeling substance of the present invention or as a raw material for synthesizing the labeling substance or a synthetic intermediate thereof. The compound, nucleic acid, and labeling substance of the present invention are more specifically as described in the following, for example.

In the compound of the present invention, it is preferable that E in the formulae (1), (1b), and (1c) be an atomic group having a main chain structure of, for example, DNA, modified DNA, RNA, modified RNA, LNA, or PNA (peptide nucleic acid).

Furthermore, in the formulae (1) and (1c), preferably, the atomic group represented by:

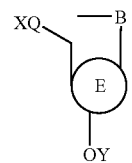

is an atomic group represented by any one of the following formulae (2) to (4),

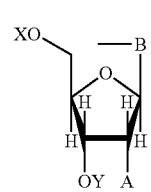

(2)

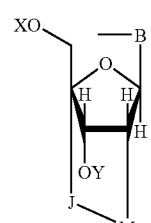

(3)

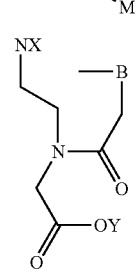

(4)

and in the formula (1b), an atomic group represented by:

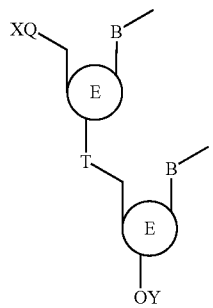

is an atomic group represented by any one of the following formulae (2b) to (4b).

(2b)
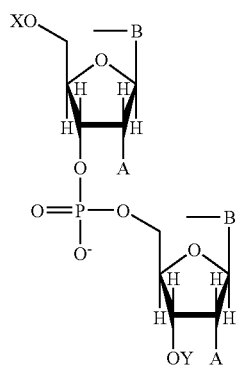

(3b)
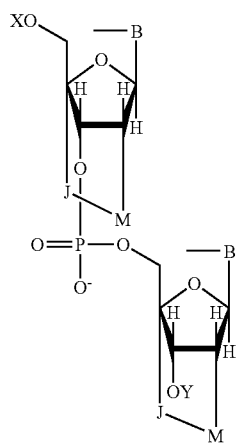

(4b)
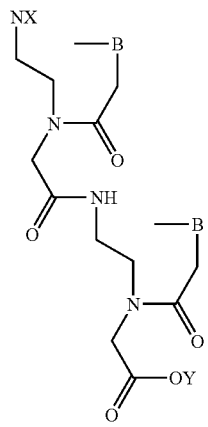

In the formulae (2) to (4) and (2b) to (4b),

A is a hydrogen atom, a hydroxy group, an alkyl group, or an electron-withdrawing group, M and J are each $CH_2$, NH, O, or S and may be identical to or different from each other, B, X, and Y are identical to those, respectively, in the formula (1), (1b), or (1c), and in the formulae (2), (3), (2b), and (3b), at least one O atom contained in a phosphoric acid linkage may be substituted with an S atom.

E is preferably an atomic group having a main chain structure of, for example, DNA, modified DNA, RNA, or modified RNA from the viewpoint of, for example, easy synthesis. However, E may be an atomic group having a main chain structure of LNA or PNA (peptide nucleic acid).

In the formulae (2) and (2b), it is preferable that, for example, the alkyl group be a methoxy group and the electron-withdrawing group be halogen.

In the formula (1), (1b), or (1c), it is preferable that each main chain length (the number of main chain atoms) of $L^1$, $L^2$, and $L^3$ be an integer of 2 or more. The upper limit of each main chain length (the number of main chain atoms) of $L^1$, $L^2$, and $L^3$ is not particularly limited and is, for example, 100 or less, more preferably 30 or less, and particularly preferably 10 or less.

Preferably, the compound of the present invention is a compound represented by the following formula (5), (6), (6b), or (6c), a tautomer or stereoisomer thereof, or a salt thereof.

(5)
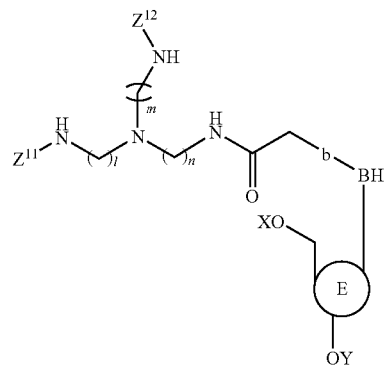

(6)
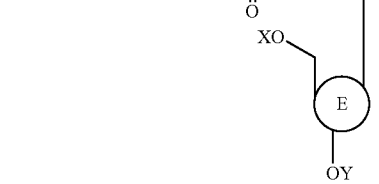

(6b)
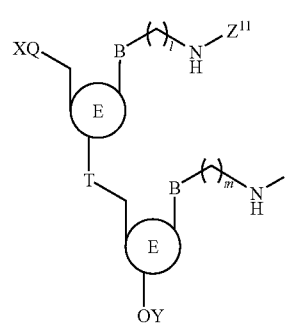

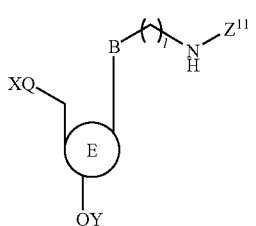

(6c)

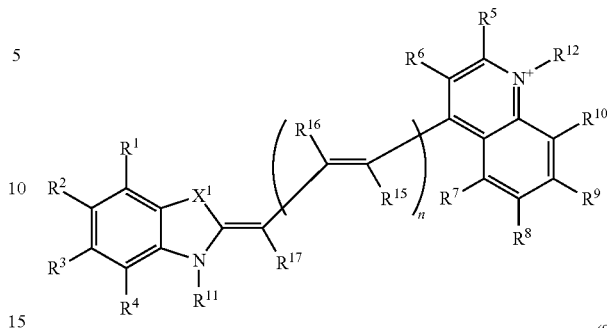

(7)

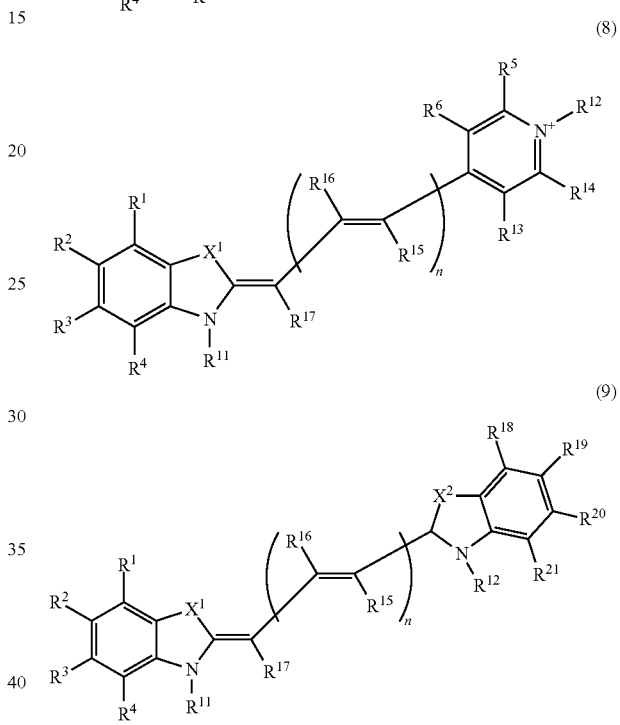

In the formulae (5), (6), (6b) and (6c), l, m, and n are arbitrary and may be identical to or different from one another, and B, E, $Z^{11}$, $Z^{12}$, X, Y, and T are identical to those in the formulae (1) and (1b), respectively.

In the formulae (5), (6), (6b), and (6c), l, m, and n each are preferably an integer of 2 or more. The upper limits of l, m, and n are not particularly limited and are, for example 100 or less, more preferably 30 or less, and particularly preferably 10 or less.

In the compound of the present invention, it is preferable that $Z^{11}$ and $Z^{12}$ each be an atomic group that exhibits an exciton effect. This allows fluorescence to be increased greatly when, for example, a double helix structure is formed, and thereby the double helix structure can be detected further effectively. However, in the compound of the present invention, it is possible to detect the double helix structure effectively even when $Z^{11}$ and $Z^{12}$ each are not an atomic group that exhibits an exciton effect or even when only one atomic group (dye) that exhibits fluorescence is introduced into one molecule.

Preferably, $Z^{11}$ and $Z^{12}$ each are, for example, an atomic group having fluorescence as described above. The atomic group having fluorescence is not particularly limited. More preferably, $Z^{11}$ and $Z^{12}$ are, for example, each independently a group derived from thiazole orange, oxazole yellow, cyanine, hemicyanine, another cyanine dye, methyl red, azo dye, or a derivative thereof. Furthermore, a group derived from another known dye also can be used suitably. Many fluorescent dyes that change the fluorescence intensity by binding to nucleic acid such as DNA have been reported. In a typical example, it has been known that ethidium bromide exhibits strong fluorescence by intercalating into a double helix structure of DNA, and it is used frequently for DNA detection. Furthermore, fluorescent dyes whose fluorescence intensity can be controlled according to the microscopic polarity, such as pyrenecarboxyamide and prodan, also are known. The thiazole orange is a fluorescent dye with a benzothiazole ring and quinoline being linked to each other with a methine group. It usually exhibits weak fluorescence but gives strong fluorescence emission by intercalating into DNA having a double helix structure. Other examples include dyes such as fluorescein and Cy3.

Further preferably, $Z^{11}$ and $Z^{12}$ are, for example, each independently an atomic group represented by any one of the following formulae (7) to (9).

In the formulae (7) to (9), $X^1$ and $X^2$ are each S or O and may be identical to or different from each other, n is 0 or a positive integer, $R^1$ to $R^{10}$ and $R^{13}$ to $R^{21}$ are each independently a hydrogen atom, a halogen atom, a lower alkyl group, a lower alkoxy group, a nitro group, or an amino group, one of $R^{11}$ and $R^{12}$ is a linking group that binds to $L^1$ or $L^2$ in the formula (1), (1b), or (1c) or NH in the formula (5), (6), (6b), or (6c), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$, and $R^1$ to $R^{21}$ in $Z^{11}$ and X, $X^2$, and $R^1$ to $R^{21}$ in $Z^{12}$ may be identical to or different from each other, respectively.

In the formulae (7) to (9), it is further preferable that in $R^1$ to $R^{21}$, the lower alkyl group be a linear or branched alkyl group with a carbon number of 1 to 6, and the lower alkoxy group be a linear or branched alkoxy group with a carbon number of 1 to 6.

In the formulae (7) to (9), it is further preferable that in $R^{11}$ and $R^{12}$, the linking group be a polymethylene carbonyl group with a carbon number of at least 2 and bind to $L^1$ or $L^2$ in the formula (1), (1b), or (1c) or NH in the formula (5), (6), (6b), or (6c), by the carbonyl group moiety thereof. The upper limit of the carbon number of the polymethylene carbonyl group is not particularly limited and is, for example, 100 or lower, preferably 50 or lower, more preferably 30 or lower, and particularly preferably 10 or lower.

When $Z^{11}$ and $Z^{12}$ each are represented by any one of the formulae (7) to (9), it is more preferable that they be, for example, each independently a group represented by formula (19) or (20).

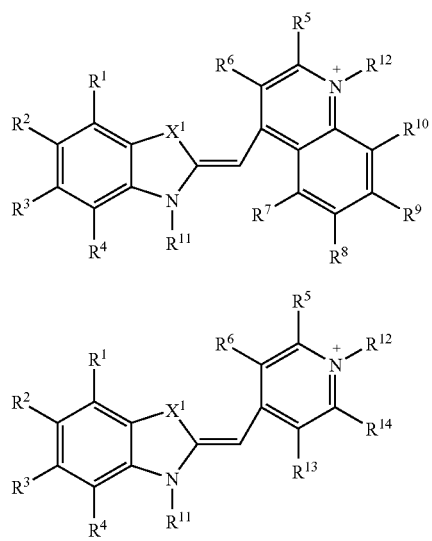

(19)

(20)

In the formulae (19) and (20), $X^1$ denotes —S— or —O—. $R^1$ to $R^{10}$, $R^{13}$ and $R^{14}$ indicates each independently a hydrogen atom, a halogen atom, a lower alkyl group, a lower alkoxy group, a nitro group, or an amino group. One of $R^{11}$ and $R^{12}$ is a linking group that binds to $L^1$ or $L^2$ in the formula (1), (1b), or (1c) or NH in the formula (5), (6), (6b), or (6c), and the other is a hydrogen atom or a lower alkyl group.

The compound of the present invention may be, for example, a compound having a structure represented by the following formula (10), a tautomer or stereoisomer thereof, or a salt thereof.

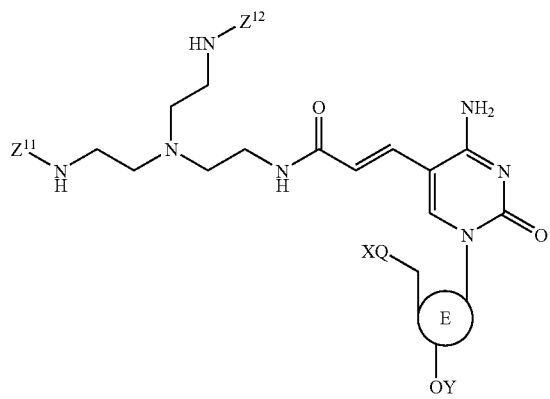

(10)

In the formula (10),

E, $Z^{11}$, $Z^{12}$, Q, X, and Y are identical to those in the formula (1), respectively.

In the formulae (1), (1b), and (1c), B may have a natural nucleobase skeleton but may have an artificial nucleobase skeleton as described above.

For example, B is preferably a structure represented by Py, Py der., Pu, or Pu der., where the Py is an atomic group having a covalent bond to E in the 1-position and a covalent bond to a linker moiety in the 5-position in the six-membered ring represented by the following formula (11), the "Py der." is an atomic group in which at least one of the atoms of the six-membered ring of the Py has been substituted with an N, C, S, or O atom, and the N, C, S, or O atom may have an electric charge, a hydrogen atom, or a substituent suitably, the Pu is an atomic group having a covalent bond to E in the 9-position and a covalent bond to a linker moiety in the 8-position in the condensed ring represented by the following formula (12), and the Pu der. is an atomic group in which at least one of all the atoms of the five-membered ring of the Pu has been substituted with an N, C, S, or O atom, and the N, C, S, or O atom may have an electric charge, a hydrogen atom, or a substituent suitably.

(11)

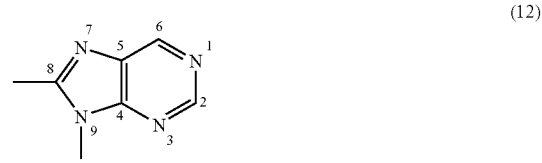

(12)

The compound of the present invention may be, for example, a compound represented by the following formula (13) or (14), a tautomer or stereoisomer thereof, or a salt thereof.

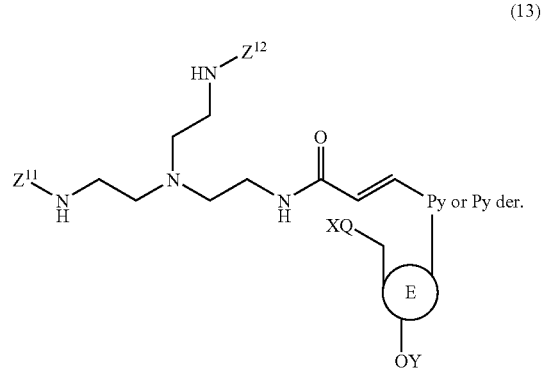

(13)

(14)

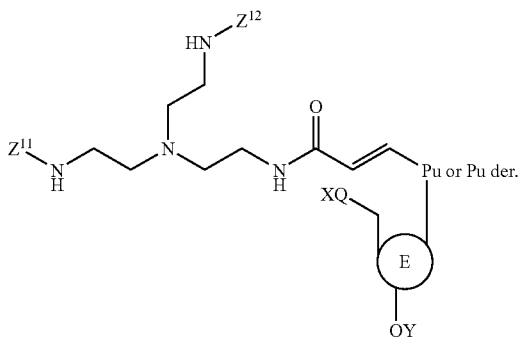

(22)

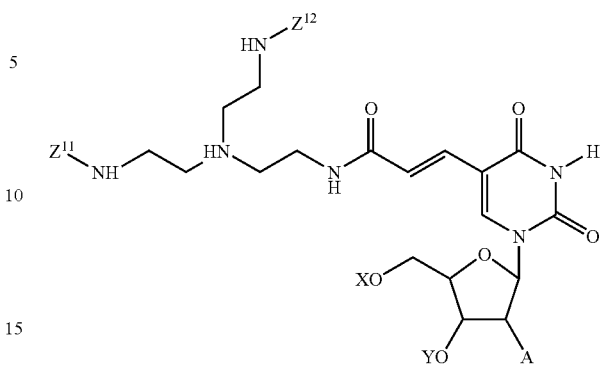

In the formulae (13) and (14), E, $Z^{11}$, $Z^{12}$, Q, X, and Y are identical to those in the formula (1), respectively, and Py, Py der., Pu, and Pu der. are as defined above.

When the compound of the present invention has a phosphoramidite group, it is preferable that the phosphoramidite group be represented by, for example, the following formula (15):

$$-P(OR^{22})N(R^{23})(R^{24})$$ (15)

where $R^{22}$ is a protecting group of a phosphate group, and $R^{23}$ and $R^{24}$ are each an alkyl group or an aryl group.

Further preferably, in the formula (15), $R^{15}$ is a cyanoethyl group, and in $R^{16}$ and $R^{17}$, the alkyl group is an isopropyl group and the aryl group is a phenyl group.

In the compound of the present invention, for example, the compound represented by the formula (1) may be a compound represented by the following formula (21).

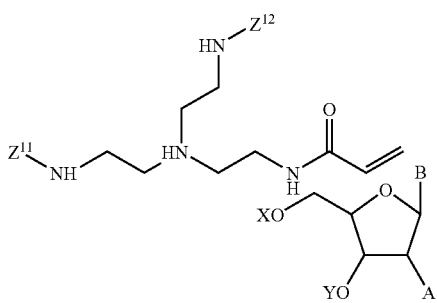

(21)

In the formula (21), A denotes a hydrogen atom or a hydroxy group. Preferably, A is a hydrogen atom. B denotes a residue of adenine, guanine, cytosine, thymine, or uracil. For example, adenine and guanine have been bonded to a double bond in the 8-position, and cytosine, thymine, or uracil have been bonded to a double bond in the 5-position. $Z^{11}$ and $Z^{12}$ each indicates independently an atomic group that exhibits fluorescence, a hydrogen atom, or a protecting group of an amino group, and are particularly preferably a residue of an oxazole yellow derivative or a thiazole orange derivative. X denotes a hydrogen atom, a protecting group of a hydroxy group that can be deprotected with acid, a monophosphate group, a diphosphate group, or a triphosphate group. Y is a hydrogen atom, a protecting group of a hydroxy group, or a phosphoramidite group.

It is further preferable that the compound represented by the formula (21) be represented by the following formula (22).

In the formula (22), A denotes a hydrogen atom or a hydroxy group. $Z^{11}$ and $Z^{12}$ are each independently an atomic group that exhibits fluorescence, a hydrogen atom, or a protecting group of an amino group, and particularly preferably a residue of an oxazole yellow derivative or a thiazole orange derivative. X denotes a hydrogen atom, a protecting group of a hydroxy group that can be deprotected with acid, a monophosphate group, a diphosphate group, or a triphosphate group. Y is a hydrogen atom, a protecting group of a hydroxy group, or a phosphoramidite group.

In the compound of the formula (21) or (22), when $Z^{11}$ and $Z^{12}$ are each a hydrogen atom or a protecting group of an amino group, two amino groups (or protected amino groups) are contained in one molecule, and therefore two labeled molecules can be introduced into one molecule using the amino groups. For example, when labeled nucleic acid is produced, with, for example, a fluorescent substance or a chemiluminescent substance being bound thereto, the nucleic acid detection sensitivity can be improved. Furthermore, as in the case where $Z^{11}$ and $Z^{12}$ are each an atomic group that exhibits fluorescence, labeling a nucleic acid with a specific fluorescent substance makes it possible to detect it easily.

Furthermore, in the compound of the formula (21) or (22), a compound in which $Z^{11}$ and $Z^{12}$ are each an atomic group that exhibits fluorescence is nucleotide modified with two fluorescence molecules, for example, a thiazole orange derivative or an oxazole yellow derivative. A probe formed of a single-stranded nucleic acid containing such a compound emits very weak fluorescence, when the probe is used by itself, due to quenching caused by exciton coupling, but emits strong fluorescence by hybridizing with DNA or RNA. That is, for example, the fluorescence of the thiazole orange derivative or the oxazole yellow derivative is suppressed strongly by the distorted structure thereof, but when the thiazole orange derivative or oxazole yellow derivative binds to DNA, the structural distortion is cancelled and fixed and thereby strong fluorescence is emitted. The fluorescence can be detected by, for example, excitation performed using an Ar laser with a wavelength of 488 nm or 514 nm, but the detection method is not limited thereto.

The compound of the present invention represented by the formula (1), (1b), or (1c) can be used for synthesizing a nucleic acid (polynucleotide), for example. That is, the compound of the present invention can be used as a labeling substance for nucleic acid (nucleic acid labeling reagent). For example, by using the compound of the present invention represented by the formula (1), (1b), or (1c) as a nucleotide substrate and carrying out a nucleic acid synthesis reaction using a single-stranded nucleic acid as a template, or by synthesizing a single-stranded nucleic acid chemically (for example, a chemical synthesis method such as a phosphoramidite method that is carried out using an automated nucleic acid synthesizer) using a compound represented by the formula (1), (1b), or (1c), a nucleic acid containing at least one molecule of the compound of the present invention in one molecule can be produced. In this case, the atomic groups $Z^{11}$ and $Z^{12}$ may be each an atomic group that exhibits fluorescence but also may be a hydrogen atom or a protecting group.

As described above, the nucleic acid of the present invention has a structure containing at least one structure represented by the following formula (16), (18b), (17), (17b), (18), or (18b). A tautomer or stereoisomer of the compound or a salt of the compound, the tautomer, or the stereoisomer also is encompassed by the nucleic acid of the present invention.

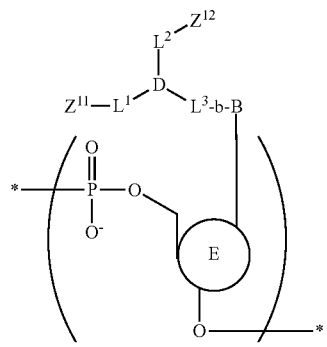

(16)

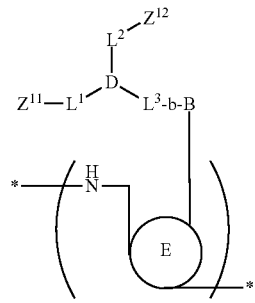

(16b)

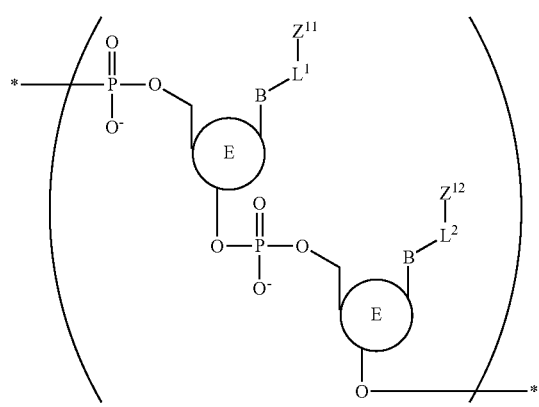

(17)

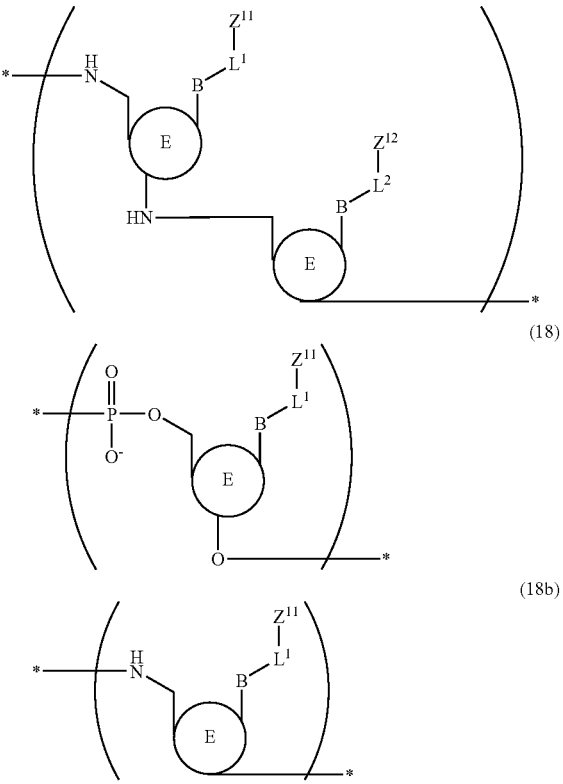

In the formulae (16), (16b), (17), (17b), (18) and (18b),
B, E, $Z^{11}$, $Z^{12}$, $L^1$, $L^2$, $L^3$, D, and b each have the structure shown in the formula (1), (1b), or (1c), where in the formulae (16), (17), and (18), E is the atomic group described in item (i) in the formula (1), (1b), or (1c), and at least one O atom in a phosphoric acid linkage may be substituted with an S atom, in the formulae (16b), (17b), and (18b), E is the atomic group described in item (ii) in the formula (1), (1b), or (1c), and in the formulae (17) and (17b), the respective Bs may be identical to or different from each other, and the respective Es may be identical to or different from each other.

In the formulae (16), (17), (16b), (17b), (18), and (18b), $Z^{11}$ and $Z^{12}$ are each an atomic group that exhibits fluorescence, and may be identical to or different from each other.

The basic skeleton of the nucleic acid of the present invention is not particularly limited. It may be, for example, any one of DNA, modified DNA, RNA, modified RNA, LNA, and PNA (peptide nucleic acid), or another structure. Furthermore, the number of bases contained in the nucleic acid of the present invention is not particularly limited. It is, for example, approximately 10 bp to 10 kb, preferably approximately 10 bp to 1 kb. When the nucleic acid of the present invention is an oligonucleotide, the length thereof is not particularly limited, and is, for instance, approximately 10 to 100 bp, more preferably 10 to 50 bp, and still more preferably 10 to 30 bp.

The number of compounds represented by the formula (1), (1b), or (1c) that are contained in the nucleic acid of the present invention is not particularly limited. It is, for example, approximately 1 to 100, and preferably approximately 1 to 20.

The compound or nucleic acid of the present invention may have, for example, a structure represented by any one of the following formulae (23) to (25). In this case, it can be used suitably as a fluorescence probe with a dye introduced therein. However, the compound of the present invention preferably used as a fluorescence probe is not limited thereto.

(23)

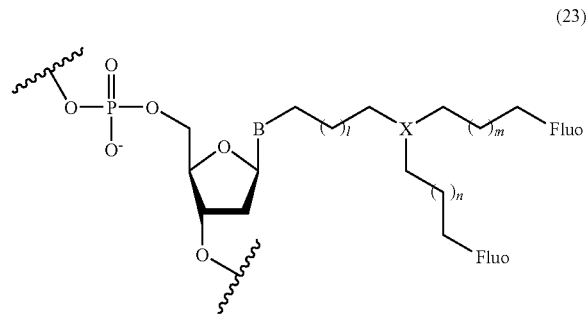

In the formula (23), two dyes (Fluo) are linked to a base B. The site at which the base B binds to a linker is not particularly limited. For example, the base B is linked to a linker in one position selected from the 4-position, the 5-position, and the 6-position of pyrimidine and the 2-position, the 3-position, the 6-position, the 7-position, and the 8-position of purine. The linker has one base linkage site, branches into at least two along the path, and is linked to dyes at the ends thereof. The method to be employed for linking it to a base or a dye is not only a bond formed by, for example, a metal-catalyzed reaction, a ring formation condensation reaction, or a Michael addition reaction to a double bond or a triple bond but also, for example, an amide bond, an ester bond, a disulfide bond, or a bond formed by, for instance, an imine formation reaction. With respect to the linker, the lengths (l, m, and n) are arbitrary, and it may contain a single bond, a double bond, a triple bond, an amide bond, an ester bond, a disulfide bond, amine, imine, an ether bond, a thioether bond, or a thioester bond. Furthermore, it is preferable that the linker not prevent the exciton effect from being caused by dimerization. The branch (X) is each atom of carbon, silicon, nitrogen, phosphorus, and boron, and protonation (for example, $NH^+$) or oxidation (for instance, $P=O$) may occur. Preferably, the dye to be used is one that exhibits an exciton effect by dimerization. The site at which the dye is linked to a linker is any portion thereof. The formula (23) shows deoxyribonucleotide, which is a partial structure of DNA, but instead of that, the nucleic acid skeleton may be ribonucleotide (RNA) as well as sugar-modified nucleic acid such as 2'O-methyl RNA or 2'-fluoro DNA, phosphoric acid modified nucleic acid such as phosphorothioate nucleic acid, or functional nucleic acid such as PNA or LNA (BNA).

(24)

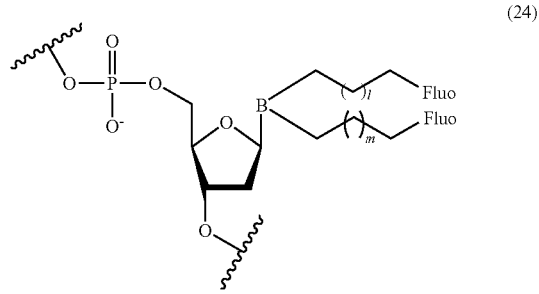

In the formula (24), two dyes (Fluo) are linked to base B. The sites by which the base B binds to linkers are not particularly limited. For example, the base B is linked to linkers in two positions selected from the 4-position, the 5-position, and the 6-position of pyrimidine and the 2-position, the 3-position, the 6-position, the 7-position, and the 8-position of purine. The two linkers each have one base linkage site and are linked to a dye at the other end thereof. The method to be employed for linking them to a base or dye is not only a bond formed by, for example, a metal-catalyzed reaction, a ring formation condensation reaction, or a Michael addition reaction to a double bond or a triple bond but also, for example, an amide bond, an ester bond, a disulfide bond, or a bond formed by, for instance, an imine formation reaction. With respect to the linkers, the lengths (l and m) are arbitrary, and they may contain a single bond, a double bond, a triple bond, an amide bond, an ester bond, a disulfide bond, amine, imine, an ether bond, a thioether bond, or a thioester bond. Furthermore, it is preferable that the linkers not prevent the exciton effect from being caused by dimerization. Preferably, the dye to be used is one that exhibits an exciton effect by dimerization. The site at which the dye is linked to a linker is any portion thereof. The formula (24) shows deoxyribonucleotide, which is a partial structure of DNA, but instead of that, the nucleic acid skeleton may be ribonucleotide (RNA) as well as sugar-modified nucleic acid such as 2'O-methyl RNA or 2'-fluoro DNA, phosphoric acid modified nucleic acid such as phosphorothioate nucleic acid, or functional nucleic acid such as PNA or LNA (BNA).

(25)

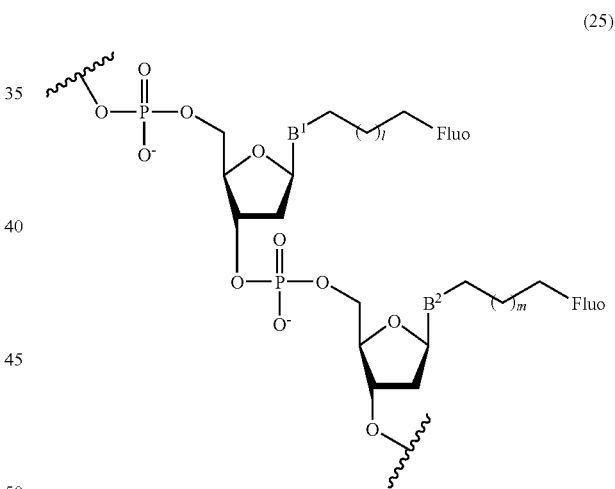

In the formula (25), the bases ($B^1$ and $B^2$) of contiguous nucleotides each are linked to one dye (Fluo). The site at which each base binds to a linker is not particularly limited. For example, each base is linked to a linker at one position selected from the 4-position, the 5-position, and the 6-position of pyrimidine and the 2-position, the 3-position, the 6-position, the 7-position, and the 8-position of purine. The two linkers each have one base linkage site and are linked to a dye at the other end thereof. The method to be employed for linking them to bases or dyes is not only a bond formed by, for example, a metal-catalyzed reaction, a ring formation condensation reaction, or a Michael addition reaction to a double bond or a triple bond but also, for example, an amide bond, an ester bond, a disulfide bond, or a bond formed by, for instance, an imine formation reaction. With respect to the linkers, the lengths (l and m) are arbitrary, and they may contain a single bond, a double bond, a triple bond, an amide bond, an ester bond, a disulfide bond, amine, imine, an ether bond, a thioether bond, or a thioester bond. Furthermore, it is preferable that the linkers not prevent the exciton effect from being caused by dimerization. Preferably, the dye to be used is one that exhibits an exciton effect by dimerization. The site at which the dye is linked to a linker is any portion thereof. The formula (25) shows deoxyribonucleotide, which is a partial structure of DNA, but instead of that, the nucleic acid skeleton may be ribonucleotide (RNA) as well as sugar-modified nucleic acid such as 2'O-methyl RNA or 2'-fluoro DNA, phosphoric acid modified nucleic acid such as phosphorothioate nucleic acid, or functional nucleic acid such as PNA or LNA (BNA).

When the compound or nucleic acid of the present invention has an isomer such as a tautomer or a stereoisomer (ex. a geometric isomer, a conformer, or an optical isomer), any isomer can be used for the present invention. The salt of the compound or nucleic acid of the present invention may be an acid addition salt but may be a base addition salt. Furthermore, the acid that forms the acid addition salt may be an inorganic acid or an organic acid, and the base that forms the base addition salt may be an inorganic base or an organic base. The inorganic acid is not particularly limited. Examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited. Examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited. Examples thereof include ammonium hydroxide, alkali metal hydroxide, alkaline earth metal hydroxide, carbonate, and hydrogen carbonate. More specific examples include sodium hydroxide, potassium hydroxide, potassium carbonate, sodium carbonate, sodium bicarbonate, potassium hydrogencarbonate, calcium hydroxide, and calcium carbonate. The organic base also is not limited. Examples thereof include ethanolamine, triethylamine, and tris(hydroxymethyl)aminomethane. The method of producing salts thereof also is not particularly limited. They can be produced by a method in which, for example, the acids or bases as described above are added suitably to the electron donor/receptor binding molecule by a known method. Furthermore, when, for example, the substituent has an isomer, any isomer can be used. For instance, in the case of a "naphthyl group", it may be a 1-naphthyl group or a 2-naphthyl group.

Furthermore, in the present invention, the alkyl group is not particularly limited. Examples thereof include a methyl group, an ethyl group, an n-propyl group, an isopropyl group, an n-butyl group, an isobutyl group, a sec-butyl group, and a tert-butyl group, as well as groups (for example, an alkylamino group and an alkoxy group) containing alkyl groups in their structures. Moreover, the perfluoroalkyl group is not particularly limited. Examples thereof include perfluoroalkyl groups derived from a methyl group, an ethyl group, an n-propyl group, an isopropyl group, an n-butyl group, an isobutyl group, a sec-butyl group, and a tert-butyl group, as well as groups containing perfluoroalkyl groups in their structures (for example, a perfluoroalkylsulfonyl group and a perfluoroacyl group). In the present invention, the acyl group is not particularly limited. Examples thereof include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group, as well as groups containing acyl groups in their structures (for example, an acyloxy group and an alkanoyloxy group). In the present invention, carbonyl carbon is included in the carbon number of the acyl group. For example, an alkanoyl group (an acyl group) with a carbon number of 1 indicates a formyl group. Furthermore, in the present invention, "halogen" denotes an arbitrary halogen element, and examples thereof include fluorine, chlorine, bromine, and iodine. In the present invention, the protecting group of an amino group is not particularly limited. Examples thereof include a trifluoroacetyl group, a formyl group, a C1-6alkyl-carbonyl group (for example, acetyl and ethylcarbonyl), a C1-6alkyl sulfonyl group, a tert-butyloxycarbonyl group (hereinafter also referred to as "Boc"), a benzyloxycarbonyl group, an allyloxycarbonyl group, a fluorenylmethyloxy carbonyl group, an arylcarbonyl group (for example, phenylcarbonyl and naphthylcarbonyl), an arylsulfonyl group (for example, phenylsulfonyl and naphthylsulfonyl), a C1-6 alkyloxycarbonyl group (for example, methoxycarbonyl and ethoxycarbonyl), a C7-10 aralkylcarbonyl group (for example, benzylcarbonyl), a methyl group, and an aralkyl group (for example, benzyl, diphenylmethyl, and trityl group). These groups may be substituted with, for example, one to three halogen atoms (for example, fluorine, chlorine, or bromine) or nitro groups. Specific examples thereof include a p-nitrobenzyloxycarbonyl group, a p-chlorobenzyloxycarbonyl group, a m-chlorobenzyloxycarbonyl group, and a p-methoxybenzyloxycarbonyl group. In the present invention, the protecting group of a hydroxy group (including one capable of being deprotected with acid) is not particularly limited. Examples thereof include a dimethoxytrityl group, a monomethoxytrityl group, and a pixyl group.

Particularly preferred examples of the compound or nucleic acid of the present invention include those described later in the section of Example, in particular, compounds (nucleic acids) 102 to 106, 110, 113, 114, 116 to 118, 120, 121, 122, 123, 124, ODN1, ODN2, ODN3, ODN4, ODN5, ODN6, ODN7, ODN8, ODN9, ODN10, ODN (anti4.5S), and ODN (antiB1), as well as geometric isomers, stereoisomers, and salts thereof. Especially, compounds 110, 113, 114, 116~118, 120, 121, 122, 123, 124, ODN1, ODN2, ODN3, ODN4, ODN5, ODN6, ODN7, ODN8, ODN9, ODN10, ODN (anti4.5S), and ODN (antiB1) are particularly good in, for example, nucleic acid detection sensitivity since thiazole orange and DNA are covalently bonded with a unique structure. Furthermore, compounds 110, 113, 117, 118, 120, 121, 122, 123, 124, ODN1, ODN2, ODN3, ODN4, ODN5, ODN9, ODN (anti4.5S) and ODN (antiB1) that contain two thiazole orange structures in one molecule can be used further effectively as a fluorescence probe of a single-stranded DNA that suppresses the fluorescence in a single-stranded state and has fluorescence intensity that is increased by forming a double helix with a complementary DNA or RNA.

Next, the labeling substance of the present invention is, as described above:

(i) a labeling substance that emits fluorescence, with two planar chemical structures contained in one molecule, which exist not in the same plane but with a certain angle formed therebetween, being located so as to be arranged in the same plane when the molecule undergoes intercalation into or groove binding to nucleic acid, (ii) a labeling substance formed of at least two dye molecule groups that do not exhibit fluorescence emission due to the exciton effect obtained when at least two dye molecules aggregate in parallel to each other but exhibit fluorescence emission with the aggregation state being resolved when the molecules undergo intercalation into or groove binding to nucleic acid, or (iii) a complex labeling substance having, as a characteristic chemical structure, a chemical structure of at least two dye molecules contained in one molecule, with the at least two dye molecules not exhibiting fluorescence emission due to the exciton effect obtained when they aggregate in parallel to each other but exhibiting fluorescence emission, with the aggregation state being resolved when the molecules undergo intercalation into or groove binding to nucleic acid.

In the case of item (ii) or (iii), it is preferable that the dye molecules each be the molecule described in item (i). Furthermore, in the case of item (iii), it is preferable that the complex labeling substance have a structure in which at least two dye molecules are bonded to a linker molecule bonded to a nucleic acid to be labeled, with an additional linker molecule being interposed therebetween so as to have a branched structure, or are bonded directly thereto with no additional linker molecule being interposed therebetween.

The labeling substance of the present invention is preferably a compound of the present invention, where the atomic groups $Z^{11}$ and $Z^{12}$ exhibit fluorescence, a tautomer or stereoisomer thereof, or a salt thereof, or a nucleic acid of the present invention, where the atomic groups $Z^{11}$ and $Z^{12}$ exhibit fluorescence, a tautomer or stereoisomer thereof, or a salt thereof. For example, in the compound or nucleic acid of the present invention, since $Z^{11}$ and $Z^{12}$ are atomic groups that exhibit the exciton effect, the fluorescence increases when a double helix structure is formed and thereby the double helix structure can be detected further effectively. However, in the compound or nucleic acid of the present invention, even when $Z^{11}$ and $Z^{12}$ are not atomic groups that exhibit the exciton effect or even when only one atomic group (dye) that exhibits fluorescence has been introduced into one molecule, it can be used as a labeling substance, for example, for nucleic acid, and the double helix structure also can be detected effectively. Examples of the form of the labeling substance according to the present invention include the form of a fluorescence probe of a single-stranded nucleic acid. However, it is not limited thereto and it may have any form such as labeled mononucleotide, labeled oligonucleotide, or double-stranded nucleic acid.

The labeling substance of the present invention is, for example, labeled mononucleotide, labeled oligonucleotide, labeled nucleic acid, or a labeled nucleic acid analog, wherein the labeling substance is a labeling substance labeled with any one of items (i) to (iii), a compound of the present invention, where $Z^{11}$ and $Z^{12}$ each are an atomic group that exhibits fluorescence, a tautomer or stereoisomer thereof, or a salt thereof, or a nucleic acid of the present invention, where $Z^{11}$ and $Z^{12}$ each are an atomic group that exhibits fluorescence, a tautomer or stereoisomer thereof, or a salt thereof.

A labeling substance of the present invention is, for example, labeled mononucleotide, labeled oligonucleotide, labeled nucleic acid, or a labeled nucleic acid analog, wherein the labeling substance is a labeling substance labeled with any one of items (i) to (iii), a compound of the present invention, where $Z^{11}$ and $Z^{12}$ each are an atomic group that exhibits fluorescence, a tautomer or stereoisomer thereof, or a salt thereof, or a nucleic acid of the present invention, where $Z^{11}$ and $Z^{12}$ each are an atomic group that exhibits fluorescence, a tautomer or stereoisomer thereof, or a salt thereof, with a linker molecule bonded to at least one base molecule or molecules forming the main chain that are contained in mononucleotide, oligonucleotide, nucleic acid, or a nucleic acid analog, or a labeling substance.

A labeling substance of the present invention is, for example, labeled mononucleotide, labeled oligonucleotide, labeled nucleic acid, or a labeled nucleic acid analog, wherein the labeling substance is a labeling substance labeled with any one of items (i) to (iii), a compound of the present invention, where $Z^{11}$ and $Z^{12}$ each are an atomic group that exhibits fluorescence, a tautomer or stereoisomer thereof, or a salt thereof, or a nucleic acid of the present invention, where $Z^{11}$ and $Z^{12}$ each are an atomic group that exhibits fluorescence, a tautomer or stereoisomer thereof, or a salt thereof, with a linker molecule bonded to a carbon atom in the 5-position of a pyrimidine nucleus or a carbon atom in the 8-position of a purine nucleus of at least one base molecule contained in mononucleotide, oligonucleotide, nucleic acid, or a nucleic acid analog.

[Method of Producing Compound and Nucleic Acid of the Present Invention]

The methods of producing the compound and nucleic acid of the present invention are not particularly limited, and known synthesis methods (production methods) can be used suitably. In the case of a compound represented by the formula (21), as an example, it may be produced by a production method including: a step of reacting tris(2-aminoethyl)amine with a compound represented by the following formula (26) after the carboxyl group of the compound is activated; a step of protecting an amino group: and a step of carrying out a reaction for protecting the hydroxy group present in the compound obtained above with a protecting group and a reaction for adding phosphoric acid or a phosphoramidite group to the hydroxy group present in the compound obtained above.

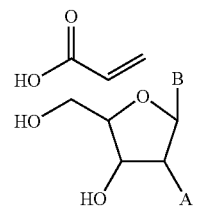

(26)

In the formula (26), A denotes a hydrogen atom or a hydroxy group and B denotes a residue of adenine, guanine, cytosine, thymine, or uracil.

For example, the following production method (synthesis method) can be used for the production of a compound and nucleic acid according to the present invention. That is, a method in which an active amino group contained in DNA and an activated carboxyl group in a labeling agent are reacted with each other in a buffer solution has been used widely as an easy DNA labeling method. This method can be used for the production of both the compound and the nucleic acid of the present invention, and can be used particularly for introduction of a linker or a dye. Examples of the method of introducing an amino group include a method using an amino modifier phosphoramidite available from GLEN RESEARCH.

The atomic groups $Z^{11}$ and $Z^{12}$ each can be converted, for example, from a protecting group to a hydrogen atom (i.e. a protecting group is removed), and further the hydrogen atom can be substituted with an atomic group (dye) having fluorescence. The method of removing the protecting group is not particularly limited, and a known method can be used suitably. The method of substituting with an atomic group (dye) having fluorescence also is not particularly limited. For example, a compound or nucleic acid of the present invention in which $Z^{11}$ and $Z^{12}$ are each a hydrogen atom may be reacted suitably with a fluorescence molecule (dye). For instance, it is preferable that at least one of $Z^{11}$ and $Z^{12}$ be an active amino group, since it tends to react with a fluorescence molecule (dye). More preferably, both of $Z^{11}$ and $Z^{12}$ are active amino groups. The fluorescence molecule (dye) also is not particularly limited and may be, for example, a compound represented by any one of the formulae (7) to (9) (where $R^{11}$ and $R^{12}$ are each a hydrogen atom or a lower alkyl group, or a carboxypolymethylene group). Furthermore, in the case of nucleic acid (polynucleotide, polynucleoside, oligonucleotide, or oligonucleoside), the step of removing a protecting group and the step of substituting with an atomic group (dye) having fluorescence may be carried out before polymerization (nucleic acid synthesis) or may be carried out after that. For example, from the viewpoint of preventing a dye portion from being damaged in the synthesis process, it is preferable that an atomic group (dye) having fluorescence be introduced after polymerization (nucleic acid synthesis).

As described above, the dye is not particularly limited and any dyes can be used. For example, it is preferably cyanine dye and particularly preferably thiazole orange. The cyanine dye has a chemical structure in which, for example, two heterocycles having hetero atoms are linked to each other with a methine linker. It is possible to synthesize fluorescent dyes with various excitation/emission wavelengths by, for example, changing the type of the heterocycles or the length of the methine linker, or introducing a substituent into the heterocycles. Furthermore, the introduction of a linker for introducing DNA also is relatively easy. Thiazole orange hardly emits fluorescence in water but emits strong fluorescence through an interaction with DNA or RNA. Conceivably, the interaction between dye molecules is prevented by an interaction with a nucleic acid and the rotation around the methine linker located between the two heterocycles of dye molecules is prevented, which leads to an increase in fluorescence intensity. The method of using a thiazole orange dye is well known. It can be used with reference to, for example, H. S. Rye, M. A. Quesada, K. Peck, R. A. Mathies and A. N. Glazer, High-sensitivity two-color detection of double-stranded DNA with a confocal fluorescence gel scanner using ethidium homodimer and thiazole orange, Nucleic Acids Res., 1991, 19, 327-33; and L. G. Lee, C. H. Chen and L. A. Chiu, Thiazole orange: a new dye for reticulocyte analysis, Cytometry, 1986, 7, 508-17.

As described above, the basic skeleton of the compound and nucleic acid of the present invention is not particularly limited. It may be, for example, any one of DNA, modified DNA, RNA, modified RNA, LNA, and PNA (peptide nucleic acid), or another structure. DNA, modified DNA, RNA, or modified RNA is preferable as the basic skeleton, since it makes synthesis easy and also makes, for instance, substitution with a dye (introduction of a dye molecule) easy. The method of introducing a dye molecule into LNA or PNA is not particularly limited and a known method can be used suitably. Specifically, for example, Analytical Biochemistry 2000, 281, 26-35. Svanvik, N., Westman, G., Wang, D., Kubista, M. (2000) Anal Biochem. 281, 26-35. Hrdlicka, P. J., Babu, B. R., Sorensen, M. D., Harrit, N., Wengel, J. (2005) J. Am. Chem. Soc. 127, 13293-13299 can be referred to.

A method of synthesizing nucleic acid having, as a basic skeleton, DNA, modified DNA, RNA, or modified RNA is well known. For example, it can be synthesized by a so-called phosphoramidite method. The phosphoramidite reagent to serve as a raw material thereof also can be synthesized easily by a known method. When the nucleic acid of the present invention is DNA, particularly short oligodeoxyribonucleotide, it can be synthesized easily with, for example, an automated DNA synthesizer. Furthermore, it also is possible to synthesize, for example, a long-chain nucleic acid (DNA) by, for instance, PCR. As described above, the position where DNA and a dye molecule are bonded to each other is not particularly limited, but, for example, the 5-position of thymidine is particularly preferable. Triphosphoric acid of a nucleotide derivative with various substituents being extended from the 5-position of thymidine is known to have relatively high efficiency of introduction carried out with DNA polymerase. Accordingly, a nucleic acid of the present invention can be synthesized easily, for example, not only when it is short oligodeoxyribonucleotide but also when it is a long-chain DNA.

Particularly, a fluorescence probe (labeling substance) of the present invention, which is a single-stranded DNA, with, for example, thiazole orange used therein have the following advantages, for example: (1) it can be prepared merely by providing a dye for DNA synthesized with an automated DNA synthesizer, in a buffer solution, and is synthetically easy, and (2) it also is possible to produce a long-chain fluorescence probe by reacting a dye with long-chain DNA prepared enzymatically. Furthermore, it can be excited with light having a relatively long wavelength around, for example, 500 nm.

[Method and kit for detecting nucleic acid]

The method for detecting nucleic acid according to the present invention is, as described above, (I) a method of detecting a nucleic acid, comprising the steps of: carrying out nucleic acid synthesis using, as a substrate, the labeling substance according to the present invention that is labeled mononucleotide or labeled oligonucleotide, thereby synthesizing a double-stranded nucleic acid to which the atomic group that exhibits fluorescence or the dye molecule structure is bonded by intercalation or groove binding;

measuring fluorescence intensity before and after the step of synthesizing the double-stranded nucleic acid; and detecting the nucleic acid synthesis by comparing the fluorescence intensities to each other that are obtained before and after the step of synthesizing the double-stranded nucleic acid, (II) a method of detecting a nucleic acid, comprising the steps of: carrying out nucleic acid synthesis by hybridizing, as a first nucleic acid, the labeling substance according to the present invention that is a single-stranded nucleic acid to a second nucleic acid having a sequence complementary to the first nucleic acid or a sequence analogous to the complementary sequence, thereby synthesizing a double-stranded nucleic acid to which the atomic group that exhibits fluorescence or the dye molecule structure is bonded by intercalation or groove binding;

measuring fluorescence intensity before and after the step of synthesizing the double-stranded nucleic acid; and detecting the hybridization between the first nucleic acid and the second nucleic acid by comparing the fluorescence intensities to each other that are obtained before and after the step of synthesizing the double-stranded nucleic acid; or (III) a method of detecting a nucleic acid, which detects formation of a triple-stranded nucleic acid or a nucleic acid analog by using a third nucleic acid that has a sequence of the aforementioned first nucleic acid or the second nucleic acid, a sequence complementary to the sequence of the first nucleic acid or the second nucleic acid, or a sequence analogous to the complementary sequence, and is labeled or not labeled with the labeling substance according to the present invention or a complex labeling substance.

It is preferable that: (a) at least two dye molecules are bonded to one base molecule in the first nucleic acid via one linker; (b) at least two dye molecules are bonded to one base molecule in the first nucleic acid via at least two linkers; or (c) at least two dye molecules bond to adjacent two base molecules in the first nucleic acid via at least one linker.

The nucleic acid synthesis preferably is carried out by, for example, an enzymatic method, but other methods also can be used. In the aforementioned methods for detecting the nucleic acid according to the present invention, it is preferable to detect a double-stranded or triple-stranded nucleic acid using the compound of the present invention, where $Z^{11}$ and $Z^{12}$ each are an atomic group that exhibits fluorescence, a tautomer or stereoisomer thereof, or a salt thereof, or a labeled nucleic acid having, in a part thereof, a structure of the nucleic acid of the present invention.

Next, a kit of the present invention includes, as described above: a nucleic acid synthesis unit; a labeling substance; and a fluorescence intensity measurement unit, wherein the labeling substance is the aforementioned labeling substance of the present invention. That is, since the labeling substance of the kit of the present invention is the labeling substance of the present invention, the kit can detect a nucleic acid with high sensitivity, for example. Except for that, there is no particular limitation on the kit of the present invention. For example, the nucleic acid synthesis unit is not particularly limited and can be, for example, a known automated nucleic acid synthesizer or the like. The fluorescence intensity measurement unit also is not particularly limited and can be, for example, a known fluorescence measuring device or the like.

The kit of the present invention preferably is used in the method of detecting a nucleic acid of the present invention. However, use thereof is not limited thereto, and it can be used for any applications. The kit of the present invention preferably is used as a kit for, for example, study, clinical use, or diagnosis.

Hereinafter, the nucleic acid detection method or kit of the present invention will be described more specifically. It is to be noted, however, the nucleic acid detection method and kit of the present invention are by no means limited to the following description.

The nucleic acid detection method of the present invention uses the labeling substance of the present invention as described above. In this case, the labeled substance of the present invention may have only one atomic group (dye) having fluorescence per molecule but has preferably at least two atomic groups (dye) having fluorescence per molecule. This allows, for example, the atomic groups (dye) having fluorescence to have an exciton effect. The exciton effect, for example, suppresses the fluorescence intensity in a single-stranded state and thereby allows a double helix structure to be detected further effectively. The "exciton effect" (exciton coupling) is an effect in which, for example, a plurality of dyes aggregate in parallel to form an H-aggregate and thereby hardly exhibit fluorescence emission. Conceivably, this effect is obtained as follows. That is, the excitation state of the dye is split into two energy levels by Davydov splitting, excitation to the higher energy level and then internal conversion into the lower energy level occur, and thereby the emission is thermally forbidden. However, these descriptions do not limit the present invention by any means. The possible occurrence of the exciton effect can be confirmed by the appearance of the absorption band of the dyes that have formed the H-aggregate in a shorter wavelength as compared to the absorption band of a single dye. Examples of the dyes that exhibit such an effect include thiazole orange and a derivative thereof, oxazole yellow and a derivative thereof, cyanine and a derivative thereof, hemicyanine and a derivative thereof, and methyl red and a derivative thereof as described above, as well as dye groups generally referred to as cyanine dyes and azo dyes.

These dyes tend to bind to a DNA-DNA double strand or DNA-RNA double strand that forms a double helix or a double strand formed of DNA or RNA and an artificial nucleic acid such as phosphothioate nucleic acid, PNA (peptide nucleic acid), or LNA (BNA), by intercalation. When a plurality of such dyes have been introduced into a probe, strong quenching occurs due to the exciton effect in a normal single-stranded state (i.e. in the state where the probe has not been hybridized yet), but an aggregate is broken down through hybridization with a target DNA or RNA and then the respective dyes intercalate into the double strand separately. In this case, no electronic interaction occurs between the dyes and therefore the exciton effect does not occur, which results in exhibition of strong fluorescence emission. The absorption band of the dyes in this stage is identical to that of a single dye, which indicates that no exciton effect occurs between the dyes. Furthermore, when dyes intercalate into a double strand, the structural torsion inherent to the dyes is cancelled, which results in further stronger fluorescence emission.

Accordingly, for example, a probe is designed in such a manner that a plurality of dyes allow the exciton effect to be obtained, so that it is possible to turn fluorescence on or off very clearly through hybridization thereof to a target sequence. The exciton effect does not occur through bonding of only one molecule of dye to a probe sequence. However, for the reasons that, for example, the intercalation of the dye caused by the double strand formation planarizes the structure of the dye, it also is possible that stronger fluorescence than that exhibited in the single-stranded state is exhibited. On the other hand, even in the case where at least two molecules of dyes are bonded, when the respective dyes are apart from each other by a distance that does not allow them to exhibit electronic correlation, the exciton effect does not occur. That is, in order to allow the exciton effect to be exhibited, at least two molecules of the dye have to be bonded to a molecule of a nucleic acid or compound of the present invention in such a manner that they are located at a distance that allows them to be close enough. In other words, when the compound or nucleic acid of the present invention is used as a fluorescence probe, it is preferable that at least two molecules of a dye be bonded to one nucleotide in the probe or one molecule of a dye be bonded to each of at least two contiguous nucleotides.

The nucleic acid detection method of the present invention can be illustrated conceptually with reference to FIG. 1. FIG. 1(A) (the left diagram indicated with "Non-hybrid") shows a probe quenched by the exciton effect, and FIG. 1(B) (the right diagram indicated with "Hybrid") shows a probe that forms a double strand to be subjected to intercalation and emits fluorescence. In FIG. 1, numeral 1 denotes a nucleic acid (fluorescence probe) of the present invention, numeral 2 indicates an atomic group (dye) that exhibits fluorescence, numeral 1' denotes a complementary strand to the nucleic acid (fluorescence probe) 1, and numeral 3 indicates a double-stranded nucleic acid formed of the probe 1 and the complementary strand 1'. In the upper part of FIG. 1, an electron transition diagram is shown. The term "Allowed" denotes allowable transition, while the term "Forbidden" denotes forbidden transition. The term "Emissive" denotes that fluorescence can be emitted, and the term "Non-emissive" denotes that theoretically, fluorescence cannot be emitted. That is, conceivably, in the single-stranded state (FIG. 1(A)), the dyes 2 in the ground state aggregate together to interact with each other according to the exciton coupling theory and the excitation state of the dye aggregate is divided into two energy levels, so that the emission is suppressed. Since the emission from a low energy level is prohibited theoretically, the singlet excitation state of the aggregate remains in a low emission state. On the other hand, conceivably, when the probe hybridizes to form a double strand (FIG. 1(B)), the dyes 2 undergo intercalation into or groove binding to double-stranded nucleic acid 3 and thereby the exciton coupling is dissolved, so that fluorescence is emitted. FIG. 1 is a schematic view that conceptually shows an example of a mechanism of detecting a nucleic acid according to the present invention. The present invention is not limited by FIG. 1 and the description thereof. In the exciton effect, the fluorescence emission can be controlled by regulating the distance between two dyes. When this system is attached to DNA for discriminating a sequence, sequence-selective fluorescence emission can be obtained. In the nucleic acid detection method or kit of the present invention, hybridization can be detected by, for example, irradiating a sample with visible light from the lower side thereof, and even visually it can be discriminated clearly. Furthermore, in the nucleic acid detection method or kit of the present invention, hybridization can be observed in a container such as a fluorescent cell, a microplate, a gel, a capillary, or a plastic tube. Moreover, in the nucleic acid detection method or kit of the present invention, for example, hybridization can be observed immediately after mixing with the target nucleic acid.

With the labeling substance and the nucleic acid detection method or kit according to the present invention, sequence-specific fluorescence detection of a nucleic acid becomes possible, for example, even in an environment where washing is difficult, such as in the case of real-time PCR or an intracellular environment. More specifically, they are applicable to the uses described in the following items (1) to (7), for example. It should be noted that, hereinafter, "the probe of the present invention" refers to a fluorescence probe that is one type of labeling substance of the present invention. As described above, the nucleic acid detection method and kit according to the present invention use the labeling substance of the present invention. The following items (1) to (7) are given merely for illustrative purpose, and the labeling substance and the nucleic acid detection method and kit according to the present invention are by no means limited to the descriptions in these items.

(1) The probe of the present invention can be used in a liquid phase homogeneous assay (using, for example, a 96-well microplate or capillary).

(2) The probe of the present invention can be used as a PCR probe. It can be used for detection of an amplification curve in a DNA amplification reaction (real-time PCR) or a low-cost method replaced with the TaqMan probe method. It can be used as a primer label or an internally labeled probe.

(3) The probe of the present invention can be used as a trapping probe or labeled probe in a DNA chip. This is a high-throughput system requiring no reagent, and the labeling process and washing process are not required. With this system, human errors can be avoided considerably. It makes it possible to carry out multiple simultaneous (high-throughput) analysis in glass or a solid-phase carrier material replaced therewith (a material to which many specimens can be attached, such as a substrate made of gold, ITO, or copper, diamond, or plastic).

(4) The probe of the present invention can be fixed to a bead, fiber, or hydrogel. It allows a gene to be detected under a semiliquid/semisolid environment. While it has a measurement environment like a liquid, it can be carried like a solid.

(5) The probe of the present invention can be used as a probe for blotting (for example, Southern blot, Northern blot, or dot blot). With the use thereof, only a target gene segment is allowed to emit light and thereby to be detected. According to the method of the present invention, washing is not required after the hybridization operation.

(6) The probe of the present invention can be used as a probe for detection and tracing of intracellular nucleic acid. This allows spatiotemporal analysis of intracellular DNA/RNA to be carried out. A fluorescence microscope and a cell sorter can be used. This can be used for DNA labeling, tracing of transcription/splicing to RNA, and RNAi functional analysis, for example. In the method of the present invention, since washing is not required, it is suitable for tracing of a living cell function.

(7) The probe of the present invention can be used as a probe for fluorescence in situ hybridization (FISH). The method of the present invention allows, for example, a tissue to be dyed. In the method of the present invention, washing is not required, which reduces human error. That is, the probe of the present invention serves as a fluorescent dye that does not emit fluorescence when not recognizing a target biomolecule. Therefore the use thereof can establish bioimaging that does not require a cumbersome washing step. This leads to highly reliable, real-time fluorescence observation with less work.

The effects of the fluorescent probe (labeling substance) of the present invention can include, for example, the following advantages as compared to conventional single-stranded quenching fluorescent probe (for example, a molecular beacon). However, they are mere examples and do not limit the present invention.

(1) It is easy to synthesize when only one type of dye is used.
(2) It is easy to use as a PCR probe when the DNA probe (labeling substance) of the present invention has a free end.
(3) It is not necessary to form a special conformation such as a hairpin structure and therefore sequences that are not associated with sequence recognition, such as a stem sequence, are not required (neither useless sequences nor restrained sequences are contained).
(4) Fluorescent dyes can be introduced into a plurality of sites (desired sites) in the probe.
(5) When at least two dye structures are contained in one molecule, the positional relationship between the dyes is restrained and thereby the S/N ratio (the fluorescence intensity ratio before and after hybridization) is high.

The fluorescence intensity of the probe according to the present invention can be changed effectively by, for example, controlling the exciton interaction in the dye portions bonded thereto. In the present invention, an approach particularly utilizing the exciton interaction makes it possible to obtain sufficiently high quenching ability for serving as an on-off probe and, for example, as described above, a number of advantages that are clearly different as compared to conventional assays. The design of such on-off fluorescence nucleotide is very important for establishment of a bioimaging assay that does not require washing, for example. The photophysical properties that the probe utilizing the exciton effect exhibits are not only very characteristic but also suitable for designing a new fluorescence DNA probe for DNA sequencing (sequence determination), genotyping (genotype analysis), monitoring of DNA conformational transition, and gene expression observation.

Furthermore, with the probe (nucleic acid) of the present invention, when, for example, a target nucleic acid sequence is determined quantitatively, it can be detected immediately that phenomena such as amplification, degradation, and protein binding of the sequence concerned occurred and the amounts of those phenomena also can be determined quantitatively. The following description is directed to such detection and quantitative determination but indicates examples and does not limit the present invention. That is, first, the probe (nucleic acid) of the present invention hybridizes with the target nucleic acid sequence at a certain substance amount ratio and thereby a double strand is formed. The substance amount of the double strand thus formed is directly proportional to the substance amount of the target nucleic acid sequence. Accordingly, measurement of the fluorescence intensity of the double strand allows a target nucleic acid sequence to be detected and the substance amount thereof to be determined quantitatively. In this case, since the probe (nucleic acid) of the present invention is prevented from emitting fluorescence, it does not hinder the measurement of the fluorescence intensity of the double strand, and thus it can be measured correctly.

EXAMPLES

The present invention is described in further detail using the following examples. However, the present invention is not limited by the following examples. In the description below, "ODN" denotes oligodeoxyribonucleotide (DNA oligomer).

The reagents and solvents used herein are commercially available. N-hydroxysuccinimidyl ester of biotin used herein was one available from PIERCE. The silica gel for purifying a compound used herein was Wako gel C-200 (Wako Pure Chemical Industries, Ltd.). $^1$H, $^{13}$C, and $^{31}$P NMR spectra were measured with JNM-α400 (trade name) available from JEOL (JOEL Ltd.). The coupling constant (J value) is indicated in hertz (Hz). The chemical shift is indicated in ppm. Dimethylsulfoxide (δ=2.48 in $^1$HNMR, δ=39.5 in $^{13}$CNMR) and methanol (δ=3.30 in $^1$HNMR, δ=49.0 in $^{13}$CNMR) were used for internal standards. For $^{31}$PNMR measurement, $H_3PO_4$ (δ=0.00) was used as an external standard. The ESI mass spectrum was measured using Bruker Daltonics APEC-II (trade name) available from Bruker Daltonics. The automated DNA synthesizer used herein was 392 DNA/RNA synthesizer (trade name) available from Applied Biosystems. In the reversed-phase HPLC, separation was carried out using Gilson Chromatograph, Model 305 (trade name), an apparatus available from Gilson, Inc. and CHEMCOBOND 5-ODS-H preparative column (trade name; 10×150 mm) available from Chemco Scientific Co., Ltd. and detection was carried out with a UV detector, Model 118 (trade name) at a wavelength of 260 nm. The mass of DNA was measured with MALDI-TOF MS. The MALDI-TOF MS used herein was PerSeptive Voyager Elite (trade name) available from Applied Biosystems. The mass was measured at an accelerating voltage of 21 kV in a negative mode, 2',3',4'-trihydroxyacetophenone was used as a matrix, and T8 ([M.H]. 2370.61) and T17 ([M.H]. 5108.37) were used as internal standards. UV and fluorescence spectrum were measured using a Shimadzu UV-2550 (trade name) spectrophotometer and a RF-5300PC (trade name) fluorescence spectrophotometer available from Shimadzu Corporation, respectively. Fluorescence lifetime was measured with a compact high-performance lifetime spectrofluometer system, HORIBA JOBIN YVON FluoroCube (trade name) equipped with NanoLED-05A (trade name) available from HORIBA, Ltd. The melting point (Tm) of double-stranded nucleic acid was measured in a 50 mM sodium phosphate buffer solution (pH=7.0) containing 100 mM sodium chloride, with the final double strand concentration being 2.5 μM. The absorbance of the sample was measured at a wavelength of 260 nm, and was traced in the range of 10° C. to 90° C. while being heated at a rate of 0.5° C./min.

From the properties thus observed, the temperature at which a first change occurred was taken as the melting point Tm.

The absorption spectrum, fluorescence spectrum, and CD spectrum measurements were carried out at a strand concentration of 2.5 μM (single strand or double strand) in a 50 mM sodium phosphate buffer solution (pH=7.0) containing 100 mM sodium chloride using a measurement cell with an optical path length of 1 cm, unless otherwise described. The bandwidth of the excitation and fluorescence emission was 1.5 nm. The fluorescence quantum yield ($\Phi_F$) was calculated based on the quantum yield $\Phi_F$=0.95 of 9,10-diphenylanthracene in ethanol, using 9,10-diphenylanthracene as a control substance. The area of the emission spectrum was calculated by integration carried out using instrumentation software. The quantum yield ($\Phi_F$) was calculated by the following formula (1):

$$\Phi_{F(S)}/\Phi_{F(R)} = [A_{(S)}/A_{(R)}] \times [(Abs)_{(R)}/(Abs)_{(S)}] \times [n_{(S)}^2/n_{(R)}^2] \quad (1)$$

where $\Phi_{F(S)}$ is the fluorescence quantum yield of a sample, $\Phi_{F(R)}$ is the fluorescence quantum yield of a control substance (Reference), $A_{(S)}$ is the area of the fluorescence spectrum of the sample, $A_{(R)}$ is the area of the fluorescence spectrum of the control substance, $(Abs)_{(S)}$ is the optical density of the sample solution obtained at an excitation wavelength, $(Abs)_{(R)}$ is the optical density of the control substance solution obtained at an excitation wavelength, $n_{(S)}$ is the refractive index of the sample solution, $n_{(R)}$ is the refractive index of the control substance solution, and calculation was carried out with $n_{(S)}$=1.333 and $n_{(R)}$=1.383.

Examples 1 to 3

According to the following Scheme 1, compounds 102 and 103 including two active amino groups protected with trifluoroacetyl groups, respectively, were synthesized (produced), and further phosphoramidite 104 was synthesized.

Scheme 1 - Reaction reagent and reaction conditions:

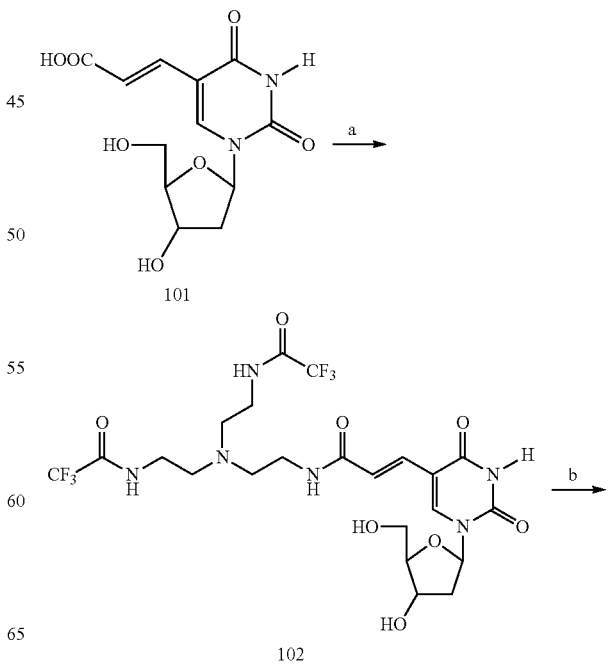

-continued

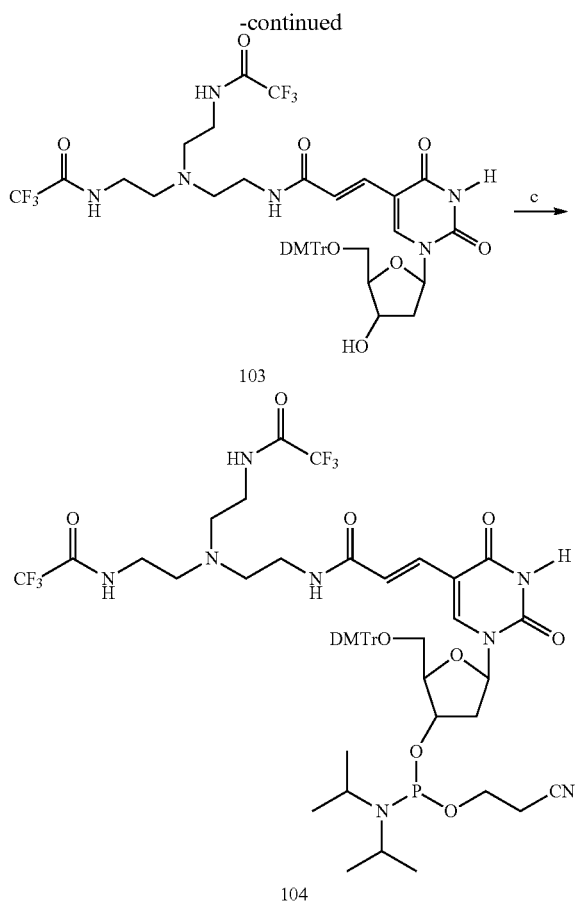

(a) (i) N-hydroxysuccinimide, EDC/DMF, (ii) tris(2-aminoethyl)-amine/CH₃CN, (iii) CF₃COOEt, Et₃N;
(b) DMTrCl/pyridine;
(c) 2-cyanoethyl-N,N,N',N'-tetraisopropyl phosphoramidite, 1H-tetrazole/CH₃CN.

Scheme 1 is described below in further detail.

Example 1

Synthesis of 2-[2-[N,N-bis(2-trifluoroacetamidoethyl)]-aminoethyl]carbamoyl-(E)-vinyl)-2'-deoxyuridine (Compound 102)

The starting material, (E)-5-(2-carboxyvinyl)-2'-deoxyuridine (Compound 101), was synthesized according to Tetrahedron 1987, 43, 20, 4601-4607. That is, first, 71 mL of 1,4-dioxane was added to 430 mg of palladium acetate (II) (FW 224.51) and 1.05 g of triphenylphosphine (FW 262.29), and further 7.1 mL of triethylamine (FW 101.19, d=0.726) was added thereto. This was heated and stirred at 70° C. After the reaction solution changed from reddish brown to blackish brown, 14.2 g of 2'-deoxy-5-iodouridine (FW 354.10) and 7.0 mL of methyl acrylate (FW 86.09, d=0.956) that were suspended in 1,4-dioxane were added thereto. This was heat-refluxed at 125° C. for one hour. Thereafter, it was filtered while it was still hot, the residue was washed with methanol, and then the filtrate was recovered. After the solvent was evaporated from the filtrate under reduced pressure, the product thus obtained was purified with a silica gel column (5-10% methanol/dichloromethane). The solvent of the collected fraction was evaporated under reduced pressure, and the residual white solid was dried under reduced pressure. About 100 mL of ultrapure water was added to the dried solid, and 3.21 g of sodium hydroxide (FW 40.00) was added thereto. This was stirred at 25° C. throughout the night. Thereafter, concentrated hydrochloric acid was added thereto to acidize the solution. The precipitate thus produced was filtered, washed with ultrapure water, and then dried under reduced pressure. Thus, 8.10 g (with a yield of 68%) of target compound (Compound 101) was obtained as white powder. The white powder was confirmed to be the target compound 101 since the ¹HNMR measured value agreed with the reference value. The ¹³CNMR measured value is described below.

(E)-5-(2-carboxy vinyl)-2'-deoxyuridine (Compound 101):

¹³CNMR (DMSO-d6): δ168.1, 161.8, 149.3, 143.5, 137.5, 117.8, 108.4, 87.6, 84.8, 69.7, 60.8, 40.1.

Next, 1.20 g of (E)-5-(2-carboxy vinyl)-2'-deoxyuridine 101 (with a molecular weight of 298.25), 925 mg of N-hydroxysuccinimide (with a molecular weight of 115.09), and 1.54 g of 1-ethyl-3-(3-dimethylaminopropyl)carbodiimide (with a molecular weight of 191.70) were placed in a recovery flask containing a stirring bar, and 20 mL of DMF was added thereto, which then was stirred at 25° C. for 16 hours. About 1 mL of acetic acid was added thereto and 300 mL of methylene chloride and 100 mL of ultrapure water were added thereto, which was then stirred vigorously. The aqueous layer was removed and further 100 mL of ultrapure water was added, which then was washed twice in the same manner. The precipitate thus produced was filtered, washed with methylene chloride, and then dried under reduced pressure. The solvent was evaporated from the filtrate, methylene chloride was added to the precipitate thus produced, and the precipitate was then recovered in the same manner as described above. The precipitates thus recovered were collected and then suspended in 80 mL of acetonitrile. This was stirred vigorously. Then 3.0 mL of tris(2-aminoethyl)amine (with a molecular weight of 146.23, d=0.976) was added all at once, which further was stirred at 25° C. for 10 minutes. Thereafter, 4.8 mL of ethyl trifluoroacetate (with a molecular weight of 142.08, d=1.194) was added and further 5.6 mL of triethylamine (with a molecular weight of 101.19, d=0.726) was added thereto, which was stirred at 25° C. for three hours. The solvent was evaporated and the product thus obtained was purified with a silica gel column (5-10% MeOH/CH₂Cl₂). The solvent was evaporated, the product thus obtained was dissolved in a small amount of acetone, and ether then was added thereto. As a result, white precipitate was produced. This was filtered and then washed with ether. Thereafter, this was dried under reduced pressure. Thus 884 mg (33.5%) of target substance (Compound 102) was obtained.

Figure 2:
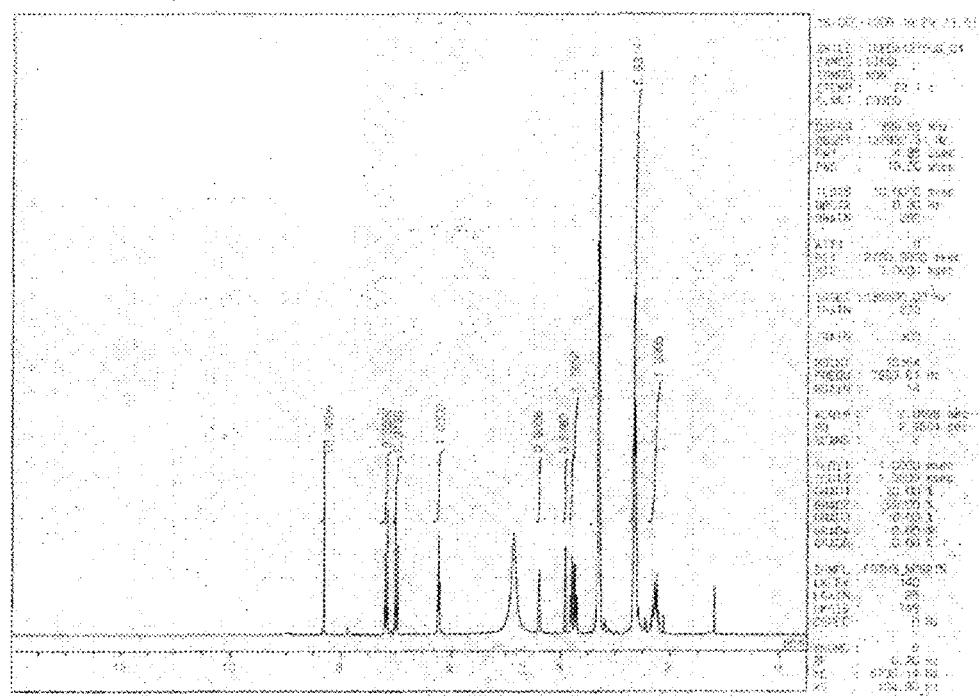
FIG. 2 shows $^{1}H$ and $^{13}C$ NMR spectra obtained from a compound of an example.
Figure 2:
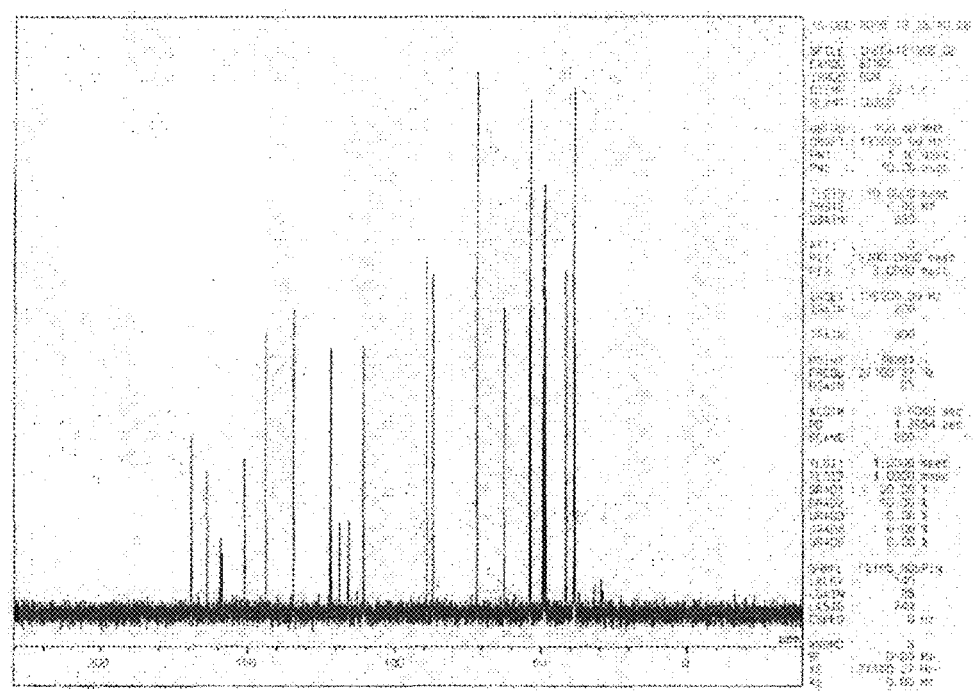

The same synthesis as described above was carried out except for slight changes in the amounts of, for example, raw materials and solvents to be used, the reaction time, and the steps to be taken. As a result, the yield was improved up to 37%. That is, 597 mg (2.0 mmol) of (E)-5-(2-carboxy vinyl)-2'-deoxyuridine 101 (with a molecular weight of 298.25), 460 mg (4.0 mmol) of N-hydroxysuccinimide (with a molecular weight of 115.09), and 767 mg (4.0 mmol) of 1-ethyl-3-(3-dimethylaminopropyl)carbodiimide hydrochloride (with a molecular weight of 191.70) were placed in a recovery flask containing a stirring bar. Thereafter, 5.0 mL of DMF was added thereto, which was stirred at 25° C. for three hours. About 0.5 mL of acetic acid was added and 100 mL of methylene chloride and 100 mL of ultrapure water were added thereto, which was stirred vigorously. The precipitate thus produced was filtered, washed with water, and then dried under reduced pressure throughout the night. The resultant white residue was suspended in 50 mL of acetonitrile, which was stirred vigorously. Then, 3.0 mL (20 mmol) of tris(2- aminoethyl)amine (with a molecular weight of 146.23, d=0.976) was added thereto all at once, which further was stirred at 25° C. for 10 minutes. Thereafter, 4.8 mL of ethyl trifluoroacetate (with a molecular weight of 142.08, d=1.194) was added and further 5.6 mL (40 mmol) of triethylamine (with a molecular weight of 101.19, d=0.726) was added thereto, which was then stirred at 25° C. for 16 hours. The solvent was evaporated and the product thus obtained was purified with a silica gel column (5-10% MeOH/CH$_2$Cl$_2$). The solvent was evaporated, the product thus obtained was dissolved in a small amount of acetone, and ether was then added thereto. As a result, white precipitate was produced. This was filtered and then washed with ether. Thereafter, this was dried under reduced pressure. Thus 453 mg (37%) of target substance (Compound 102) was obtained as white powder. The instrumental analytical values of Compound 102 are indicated below. Further, a $^1$HNMR spectrum diagram is shown in FIG. 2.

2-[2-[N,N-bis(2-trifluoroacetamidoethyl)]-aminoethyl]carbamoyl-(E)-vinyl)-2'-deoxyuridine (Compound 102)

$^1$HNMR (CD$_3$OD): δ8.35 (s, 1H), 7.22 (d, J=15.6 Hz, 1H), 7.04 (d, J=15.6 Hz, 1H), 6.26 (t, J=6.6 Hz, 1H), 4.44-4.41 (m, 1H), 3.96-3.94 (m, 1H), 3.84 (dd, J=12.2, 2.9 Hz, 1H), 3.76 (dd, J=12.2, 3.4 Hz, 1H), 3.37-3.30 (m, 6H), 2.72-2.66 (m, 6H), 2.38-2.23 (m, 2H). $^{13}$CNMR (CD$_3$OD): δ169.3, 163.7, 159.1 (q, J=36.4 Hz), 151.2, 143.8, 134.3, 122.0, 117.5 (q, J=286 Hz), 110.9, 89.1, 87.0, 71.9, 62.5, 54.4, 53.9, 41.7, 38.9, 38.7. HRMS (ESI) calcd for C$_{22}$H$_{29}$F$_6$N$_6$O$_8$ ([M+H]$^+$) 619.1951, found 619.1943.

Example 2

Synthesis of 5'-O-DMTr-(2-[2-[N,N-bis(2-trifluoroacetamidoethyl)]-aminoethyl]carbamoyl-(E)-vinyl)-2'-deoxyuridine (Compound 103)

Figure 3:
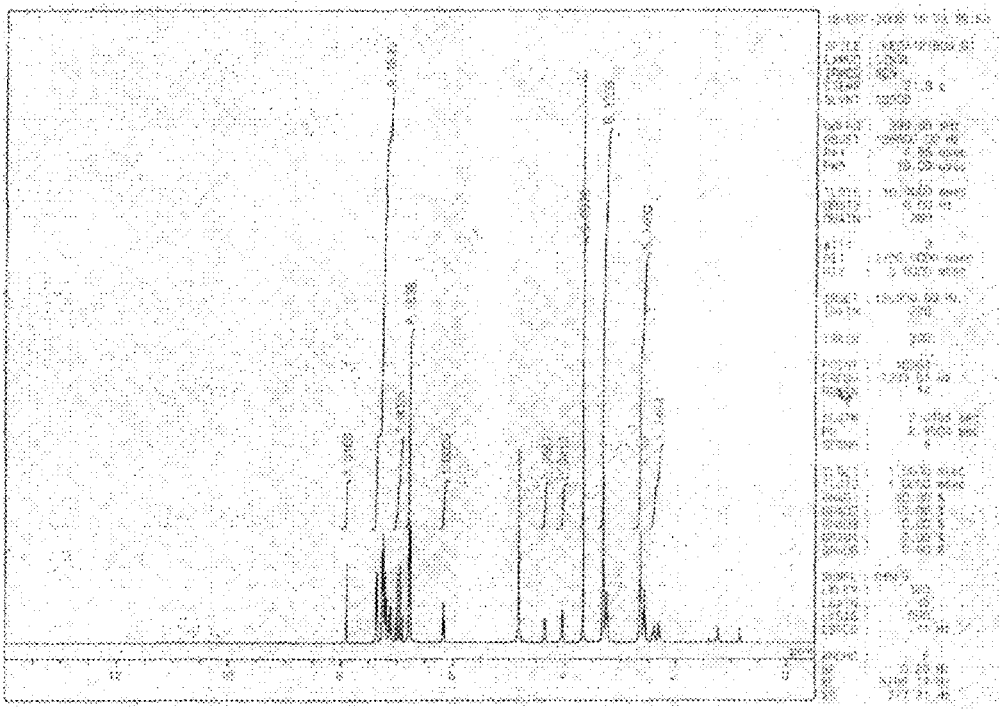
FIG. 3 shows $^{1}H$ and $^{13}C$ NMR spectra obtained from another compound of an example.
Figure 3:
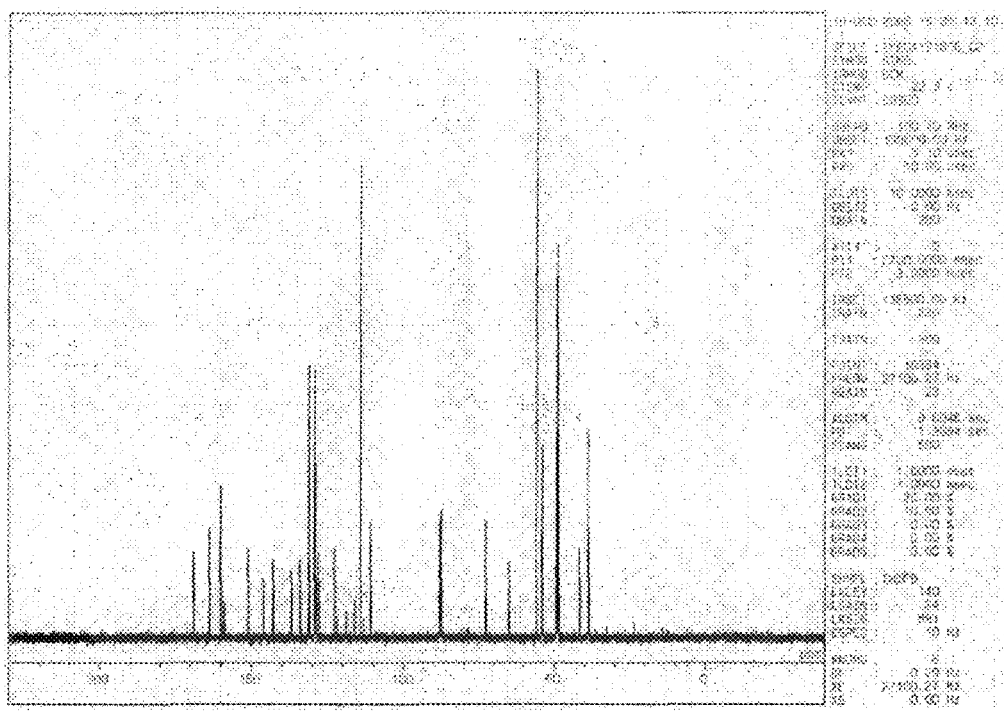

5'-hydroxy group of Compound 102 was protected with a DMTr group. Thus Compound 103 was obtained. That is, first, 618 mg of Compound 102 (with a molecular weight of 618.48) and 373 mg of 4,4'-dimethoxytritylchloride (with a molecular weight of 338.83) were placed in a recovery flask containing a stirring bar. Then 10 mL of pyridine was added thereto, which was stirred at 25° C. for 16 hours. A small amount of water was added thereto, the solvent was evaporated, and the product thus obtained was purified with a silica gel column (2-4% MeOH, 1% Et$_3$N/CH$_2$Cl$_2$). The solvent of the fraction containing the target Compound 103 was evaporated. Thus 735.2 mg (79.8%) of target substance (Compound 103) was obtained. The instrumental analytical values of Compound 103 are indicated below. Further, a $^1$HNMR spectrum diagram is shown in FIG. 3.

5'-O-DMTr-(2-[2-[N,N-bis(2-trifluoroacetamidoethyl)]-aminoethyl]carbamoyl-(E)-vinyl)-2'-deoxyuridine (Compound 103):

$^1$HNMR (CD$_3$OD): δ7.91 (s, 1H), 7.39-7.11 (m, 9H), 7.02 (d, J=15.6 Hz, 1H), 6.93 (d, J=15.6 Hz, 1H), 6.80-6.78 (m, 4H), 6.17 (t, J=6.6 Hz, 1H), 4.38-4.35 (m, 1H), 4.06-4.04 (m, 1H), 3.68 (s, 6H), 3.32-3.22 (m, 8H), 2.66-2.55 (m, 6H), 2.40 (ddd, J=13.7, 5.9, 2.9 Hz, 1H), 2.33-2.26 (m, 1H). $^{13}$CNMR (CD$_3$OD): δ168.9, 163.7, 160.1, 159.1 (q, J=36.9 Hz), 151.0, 146.1, 143.0, 137.0, 136.9, 134.1, 131.24, 131.16, 129.2, 128.9, 128.0, 122.5, 117.5 (q, J=286.7 Hz), 114.2, 110.9, 88.1, 87.9, 87.6, 72.6, 65.0, 55.7, 54.2, 53.9, 41.7, 38.9, 38.6. HRMS (ESI) calcd for C$_{43}$H$_{47}$F$_6$N$_6$O$_{10}$ ([M+H]$^+$) 921.3258. found 921.3265.

Example 3

Synthesis of 5'-O-DMTr-(2-[2-[N,N-bis(2-trifluoroacetamidoethyl)]-aminoethyl]carbamoyl-(E)-vinyl)-2'-deoxyuridine, 3'-[(2-cyanoethyl)-(N,N-diisopropyl)]-phosphoramidite (Compound 104)

First, 188 mg (0.20 mmol) of Compound 103 (with a molecular weight of 920.85) was allowed to form an azeotrope with CH$_3$CN, and 28.6 mg (0.40 mmol) of 1H-tetrazole (with a molecular weight of 70.05) was added thereto. This was vacuum-dried with a vacuum pump overnight. Then, 5.1 mL of CH$_3$CN was added thereto and thereby the reagent was dissolved therein, which then was stirred. Thereafter, 194 μL (0.60 mmol) of 2-cyanoethylN,N,N',N'-tetraisopropylphosphoramidite (with a molecular weight of 301.41, d=0.949) then was added thereto all at once, which was stirred at 25° C. for two hours. After that, a mixture of 50 mL of ethyl acetate and 50 mL of saturated sodium bicarbonate water was added thereto, and liquid separation was carried out. After the organic layer thus obtained was washed with saturated saline, it was dried with magnesium sulfate. The magnesium sulfate was removed by filtration, and the solvent was then evaporated. The crude product obtained by this liquid separation was allowed to form an azeotrope with CH$_3$CN. Thereafter, assuming that the product (Compound 104) was obtained with a yield of 100%, 0.1 M of CH$_3$CN solution was prepared and was used for DNA synthesis. The fact that Compound 104 had been obtained was confirmed from $^{31}$PNMR (CDCl$_3$) and HRMS (ESI) of the crude product. The values thereof are indicated below.

Compound 104:

$^{31}$PNMR (CDCl$_3$) δ 149.686, 149.430; HRMS (ESI) calcd for C$_{52}$H$_{64}$F$_6$N$_8$O$_{11}$P ([M+H]$^+$) 1121.4336. found 1121.4342.

Example 4

DNA Oligomer Synthesis

Scheme 2

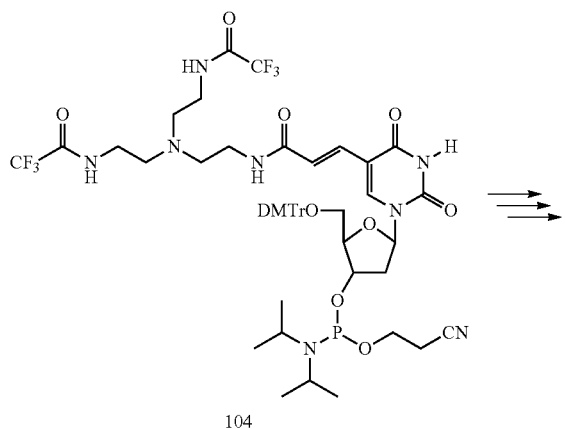

104

-continued

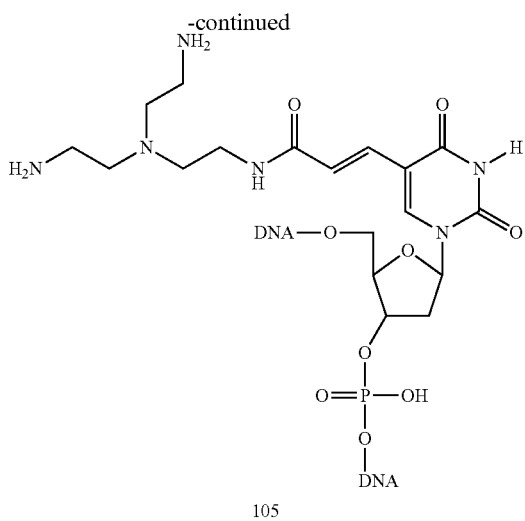

105

Figure 4:
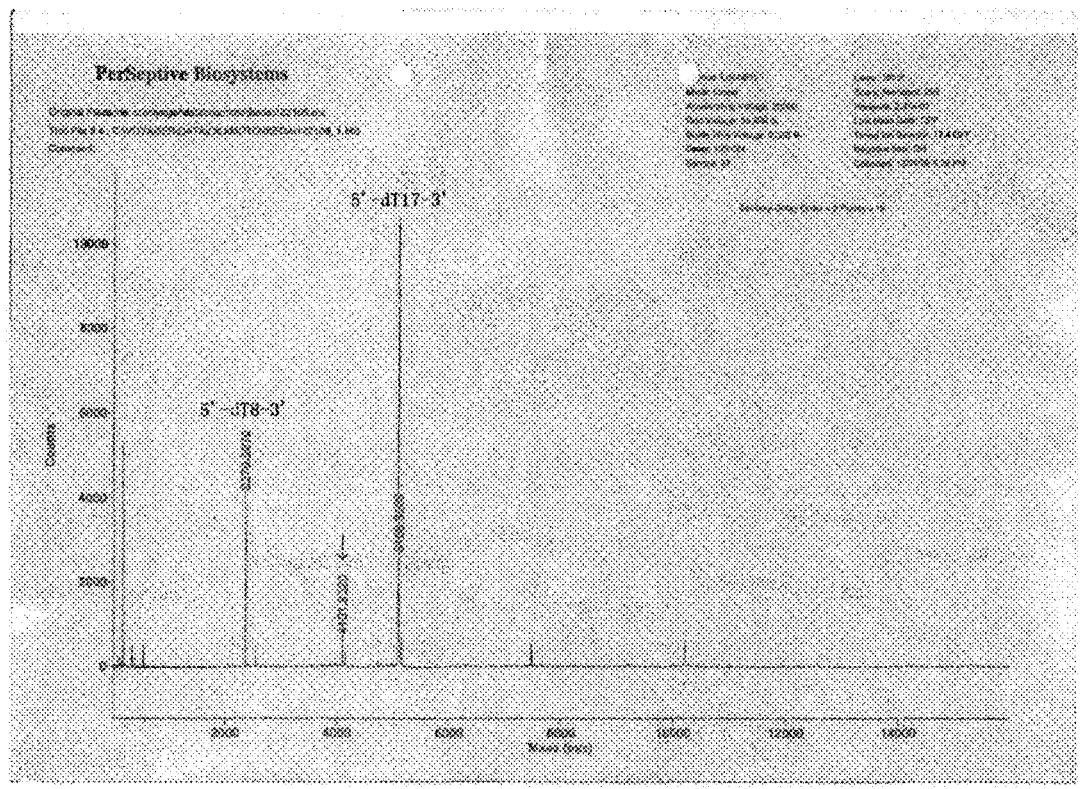
FIG. 4 shows a MALDI-TOF mass spectrum of purified DNA oligomer 5'-d(CGCAATXTAACGC)-3'; the arrow shows the mass peak (4101.9) derived from the purified product, and the calculated value of $[M-H]^{-}$ is 4101.8 based on a calculated value of molecular weight of 4102.8 ($C_{134}H_{176}N_{52}O_{76}P_{12}$) and therefore matches therewith.

The synthesis of oligodeoxyribonucleotide with an automated DNA synthesizer using Compound 104 was carried out by a conventional phosphoramidite method (DMTr OFF) on a 1 μmol scale. Thus DNA oligomer with a sequence of 5'-d(CGCAATXTAACGC)-3' (13-mer, the structure of X is the same as that of Chemical Formula 105) (SEQ ID NO. 1) was synthesized. Deprotection was carried out with concentrated ammonia water (28 mass %) at 55° C. for 16 hours. Ammonia was volatilized with a speed vac, and the product thus obtained was passed through a 0.45-μm filter. Thereafter, DNA oligomer cut out therefrom was analyzed by reversed-phase HPLC, and the peak that had appeared after about 10.5 minutes was purified (CHEMCOBOND 5-ODS-H (trade name); 10×150 mm, 3 mL/min, 5-30% $CH_3CN$/50 mM TEAA buffer pH 7 (20 minutes), detected at 260 nm). The molecular weight of the product thus purified was measured with a MALDI TOF mass spectrometer in its negative mode. As a result, it was confirmed that the product had the molecular weight (4102.8, which was a value calculated in terms of $C_{134}H_{176}N_{52}O_{76}P_{12}$) expected from the aforementioned sequence of 5'-d(CGCAATXTAACGC)-3' (13-mer, the structure of X is as shown in Chemical Formula 105) ([M−H]$^-$ measured value: 4101.9, calculated value: 4101.8). FIG. 4 shows the spectrum obtained with the MALDI TOF mass spectrometer.

Further, 5'-d(CGCAATXTAACGC)-3' (13-mer, the structure of X is as shown in Chemical Formula 105) was synthesized in the same manner as described above except that the deprotection was carried out with the concentrated ammonia water at 55° C. for 4 hours and further at 25° C. for 16 hours, the concentration of the TEAA (triethylamine acetate) buffer (pH 7) was 0.1 M in the reversed-phase HPLC, and the development time was at least 30 minutes in the reversed-phase HPLC. Moreover, a DNA (containing nucleotide represented by Chemical Formula 105) that was used as a raw material for each ODN indicated in Table 1 was synthesized in the same manner.

In order to determine the concentration of each DNA thus synthesized, each purified DNA was digested completely at 25° C. over 16 hours using calf intestinal alkaline phosphatase (50 U/mL), snake venom phosphodiesterase (0.15 U/mL), and P1 nuclease (50 U/mL). The digested liquids thus obtained were analyzed by HPLC with a CHEMCOBOND 5-ODS-H (trade name) column (4.6×150 mm). In this analysis, 0.1 M TEAA (pH 7.0) was used as a developer and the flow rate was 1.0 mL/min. The concentration of the DNA synthesized as described above was determined as compared to the peak area of the standard solution containing dA, dC, dG, and dT, the concentration of each of which was 0.1 mM. Furthermore, the DNA synthesized as described above also was identified with a MALDI TOF mass spectrum. The mass spectrometry values thereof are indicated below, where [105] denotes that the nucleotide represented by Chemical Formula 105 is inserted in that site.

CGCAAT[105]TAACGC, calcd for $C_{134}H_{177}N_{52}O_{76}P_{12}$ ([M+H]$^+$) 4103.8. found 4107.0;

TTTTTT[105]TTTTTT, calcd for $C_{138}H_{187}N_{30}O_{90}P_{12}$ ([M+H]$^+$) 4077.8. found 4076.9;

TGAAGGGCTT[105]TGAACTCTG, calcd for $C_{205}H_{265}N_{77}O_{122}P_{19}$ ([M+H]$^+$) 6348.2. found 6348.7;

GCCTCCT[105]CAGCAAATCC[105]ACCGGCGTG, calcd for $C_{285}H_{376}N_{108}O_{169}P_{27}$ ([M+H]$^+$) 8855.0. found 8854.8;

CCTCCCAAG[105]GCTGGGAT[105]AAAGGCGTG, calcd for $C_{289}H_{376}N_{116}O_{168}P_{27}$ ([M+H]$^+$) 8999.1. found 9002.2.

Example 5

Biotin Modification of DNA Oligomer Containing Nucleotide Having Two Amino Groups Scheme 3

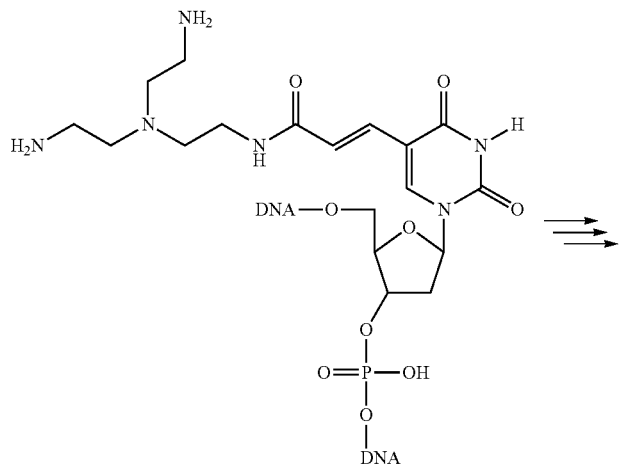

105

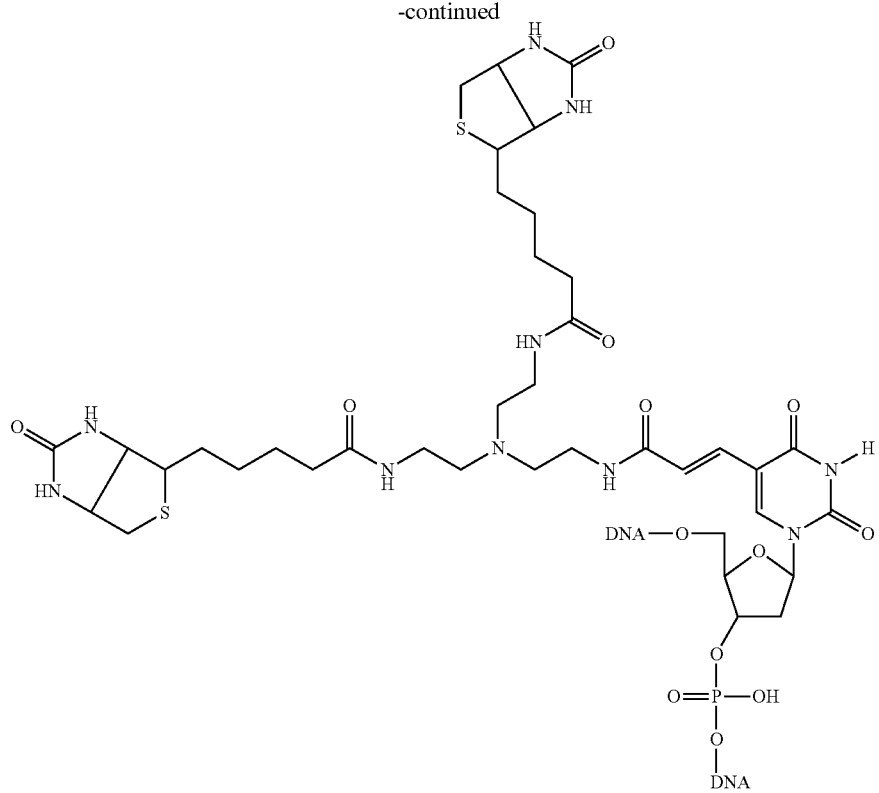

106

Figure 5:
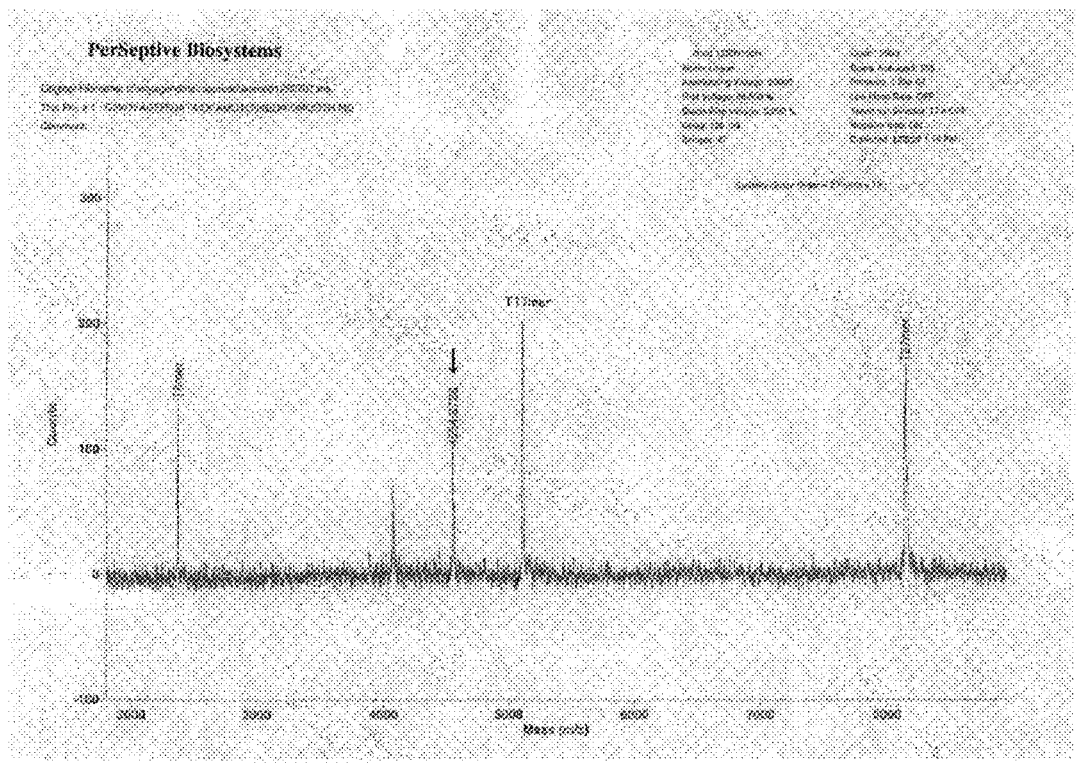
FIG. 5 shows a MALDI-TOF mass spectrum of a reaction product of DNA oligomer 5'-d(CGCAATXTAACGC)-3' and a biotin derivative; the arrow shows the mass peak (4554.3) derived from the purified product, and the calculated value of $[M-H]^{-}$ is 4554.4 based on a calculated value of molecular weight of 4555.4 ($C_{134}H_{176}N_{52}O_{76}P_{12}$) and therefore matches therewith.

The synthesized DNA oligomer 5'-d(CGCAATX-TAACGC)-3' (Compound 105, where Compound 4 was used as X) was allowed to react with N-hydroxysuccinimidyl ester of biotin and thereby two amino groups were labeled with two 2 biotins (Scheme 3 shown above). That is, first, 30 μL of 5'-d(CGCAATXTAACGC)-3' (Compound 105, with a strand concentration of 320 μM), 10 μL of $Na_2CO_3/NaHCO_3$ buffer (1 M, pH 9.0), and 60 μl, of $H_2O$ were mixed together. Then 100 μL of biotin N-hydroxysuccinimidyl ester DMF solution (20 mM) was added thereto, which was then mixed well. This was allowed to stand still at 25° C. for 16 hours. Thereafter, 800 μL of $H_2O$ was added thereto, which was passed through a 0.45-μm filter. The peak that appeared in reversed-phase HPLC after about 14 minutes was purified (CHEMCOBOND 5-ODS-H 10×150 mm, 3 mL/min, 5-30% $CH_3CN$/50 mM TEAA buffer (20 minutes), detected at 260 nm). The product obtained by this HPLC purification was measured with the MALDI TOF mass spectrometer in its negative mode. As a result, the peak was observed at 4554.3. This peak value agreed with the calculated value of $[M-H]^-$, 4554.4, determined from the molecular weight of 4555.4 (a value calculated in terms of $C_{154}H_{204}N_{56}O_{80}P_{12}S_2$) of the target product 6 in which two biotin molecules reacted with two amino groups. FIG. 5 shows the spectrum obtained with the MALDI TOF mass spectrometer.

Using this compound 6 (in a single-stranded state), double-stranded DNA and RNA were synthesized, and the fluorescence intensity obtained in the single-stranded state was compared to that obtained in the double-stranded state. As a result, it was confirmed that the fluorescence emission of the DNA fluorescence probe (Compound 6) was suppressed in the single-stranded state, while strong fluorescence emission was obtained when it formed a double helix together with a complementary nucleic acid.

In Examples 6 to 13 described below, thiazole orange derivatives having carboxymethylene linkers represented by the following Chemical Formulae b and c were synthesized. They were activated as N-hydroxysuccinic ester and were allowed to react with DNA oligomer (oligonucleotide) having active amino groups. Thus various oligonucleotides (fluorescence DNA probes) having fluorescence were prepared. That is, various oligonucleotides (fluorescence DNA probes) were produced that were different from one another in length of the methylene linker extended from a dye and in the linker containing the amino group extended from the 5-position of thymidine. As a result, in any of the various fluorescence DNA probes, it was possible to suppress the fluorescence emission of the single-stranded DNA fluorescence probe and to obtain strong fluorescence emission when it formed a double helix together with a complementary nucleic acid. In the following Chemical Formulae b and c, n denotes the linker length (the number of linking atoms).

a

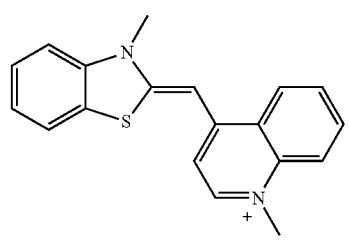

41
-continued
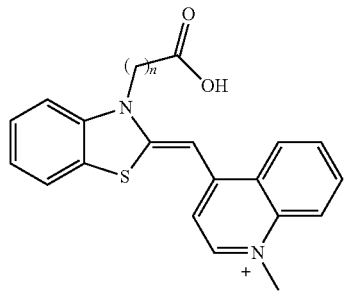
42
-continued
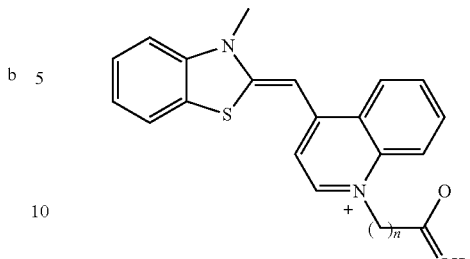
Example 6
Synthesis of Compound Having, in One Molecule, Structures Derived from Thiazole Orange in Two Places
Scheme 4
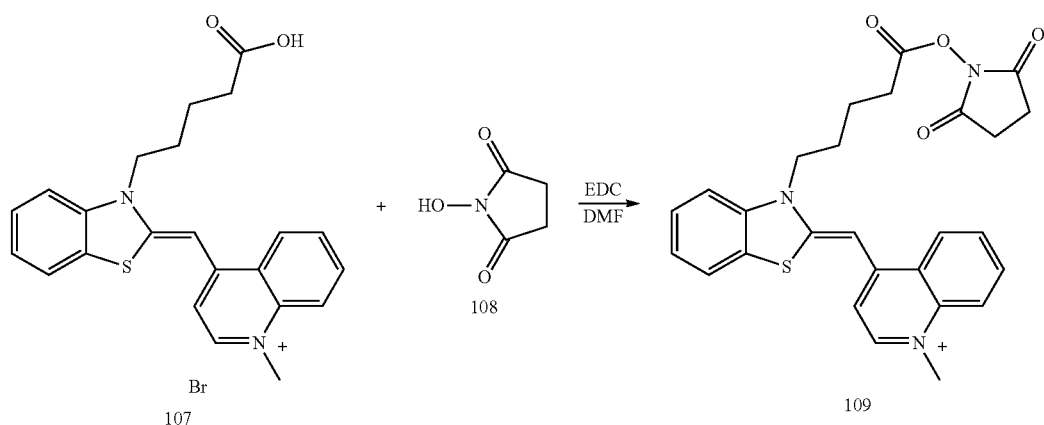
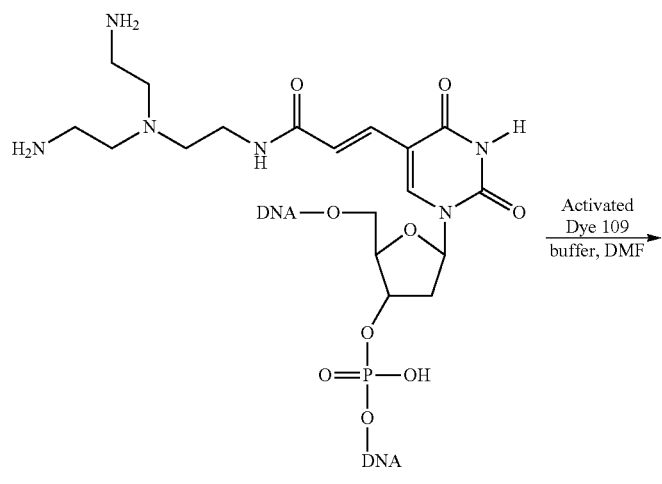

-continued
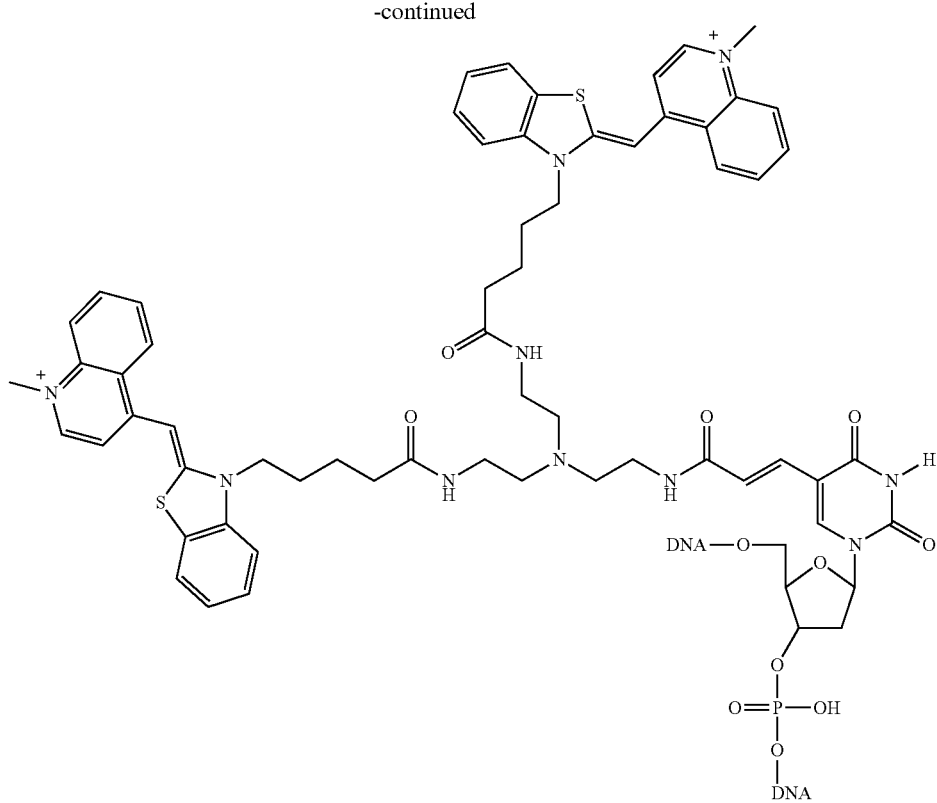
110
As shown in Scheme 4, DNA oligomer (oligonucleotide) 110 was synthesized that has, in one molecule, structures derived from thiazole orange in two places. A more specific description follows.
The thiazole orange derivative 107 was synthesized as indicated below in Scheme 5 with reference to Organic Letters 2000, 6, 517-519.
Scheme 5
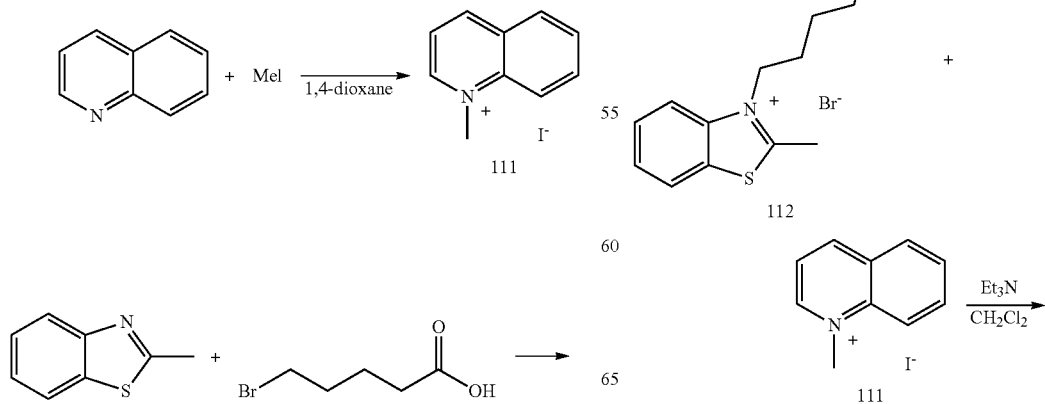
-continued
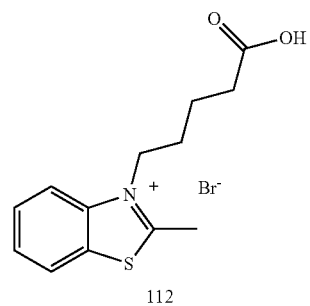

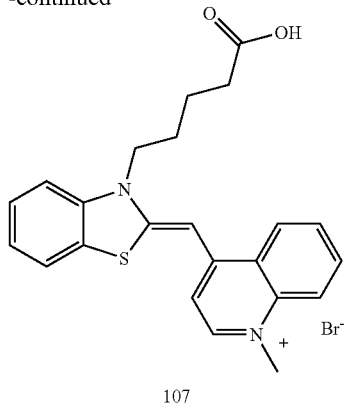

107

(1) Synthesis of N-methylquinolinium iodide (Compound III)

N-methylquinolinium iodide (Compound III) was synthesized according to the description in the aforementioned reference. Specifically, 2.4 mL of quinoline and 4 mL of methyl iodide were added to 42 mL of anhydrous dioxane, which was stirred at 150° C. for one hour. Thereafter, it was filtered and thereby a precipitate was collected and then washed with ether and petroleum ether. This was dried and thus N-methylquinolinium iodide (Compound III) was obtained.

(2) Synthesis of 3-(4-carboxybutyl)-2-methylbenzothiazolium bromide (Compound 112)

First, 8 mL of 2-methylbenzothiazole (FW 149.21, d=1.173) and 9.4 g of 5-bromovaleric acid (5-bromopentanoic acid) (FW 181.03) were stirred at 110° C. for 16 hours. The crude product was cooled to room temperature and a solid thus produced was suspended in 20 mL of methanol and further 40 mL of ether was added thereto. The precipitate thus produced was filtered and then washed with dioxane until the odor of 2-methylbenzothiazole was removed. This further was washed with ether and then dried under reduced pressure. Thus 9.8 g of white powder was obtained. Thereafter, $^1$HNMR of this white powder was measured. As a result, it was found to be a mixture of 3-(4-carboxybutyl)-2-methylbenzothiazolium bromide (Compound 112), which was the target substance whose 2-position had been alkylated, and 3-(4-carboxybutyl)-benzothiazolium bromide whose 2-position had not been alkylated. The peak ratio of proton was non-alkylated: alkylated=10:3. This crude product was used for the next reaction without further being treated.

(3) Synthesis of 1-methyl-4-[{3-(4-carboxybutyl)-2 (3H)-benzothiazolylidene}methyl]quinolinium bromide (Compound 107)

First, 2.18 g of crude product containing 3-(4-carboxybutyl)-2-methylbenzothiazolium bromide (Compound 112) obtained in (2) above and 700 mg of N-methylquinolinium iodide (Compound III) (FW 271.10) were stirred in 10 mL of methylene chloride at 25° C. for two hours in the presence of 3.6 mL of triethylamine (FW 101.19, d=0.726). Thereafter, 50 mL of ether was added thereto and a precipitate produced thereby was filtered, washed with ether, and then dried under reduced pressure. The precipitate was suspended in 50 mL of ultrapure water, which was filtered, washed with ultrapure water, and then dried under reduced pressure. Further, the precipitate was dispersed in 50 mL of acetonitrile, which was filtered, washed with acetonitrile, and then dried under reduced pressure. Thus 307.5 mg of red powder was obtained (with a yield of 25.3%). This red powder was confirmed to be the target substance (Compound 107) through a comparison in $^1$HNMR spectrum with the reference value.

Moreover, it also was possible to synthesize 3-(4-carboxybutyl)-2-methylbenzothiazolium bromide (Compound 112) and 1-methyl-4-[{3-(4-carboxybutyl)-2(3H)-benzothiazolylidene}methyl]quinolinium bromide (Compound 107) as follows. That is, first, 11.7 mL (92 mmol) of 2-methylbenzothiazole (FW 149.21, d=1.173) and 13.7 g (76 mmol) of 5-bromovaleric acid (5-bromopentanoic acid) (FW 181.03) were stirred at 150° C. for one hour. The crude product was cooled to room temperature and the solid thus produced was suspended in 50 mL of methanol. Further, 200 mL of ether was added thereto. The precipitate thus produced was filtered, washed with ether, and then dried under reduced pressure. Thus 19.2 g of light purple powder was obtained. This powder was a mixture of a target compound 112 (3-(4-carboxybutyl)-2-methylbenzothiazolium bromide) and 2-methylbenzothiazolium bromide. This mixture was subjected to $^1$HNMR (in DMSO-d6) measurement, and the yield of the target compound 112 was calculated to be 9.82 g (14 mmol, 32%) from the peak area ratio between the peak at 8.5 ppm (derived from the target compound 112) and the peak at 8.0 ppm (derived from 2-methylbenzothiazolium bromide). This mixture (crude product) was used for the next reaction without being purified. In the same manner as described above except that the 5-bromovaleric acid (5-bromopentanoic acid) was replaced with 4-bromobutyric acid (4-bromobutanoic acid), 3-(4-carboxypropyl)-2-methylbenzothiazolium bromide with a linker (a polymethylene chain linked to a carboxyl group) having a carbon number n of 3 was synthesized, which was obtained with a yield of 4%. Furthermore, in the same manner as described above except that 5-bromovaleric acid (5-bromopentanoic acid) was replaced with 6-bromohexanoic acid, 3-(4-carboxypentyl)-2-methylbenzothiazolium bromide with a linker (a polymethylene chain linked to a carboxyl group) having a carbon number n of 5 was synthesized, which was obtained with a yield of 35%. Moreover, in the same manner as described above except that 5-bromovaleric acid (5-bromopentanoic acid) was replaced with 7-bromoheptanoic acid, 3-(4-carboxypropyl)-2-methylbenzothiazolium bromide with a linker (a polymethylene chain linked to a carboxyl group) having a carbon number n of 6 was synthesized, which was obtained with a yield of 22%.

Figure 6:
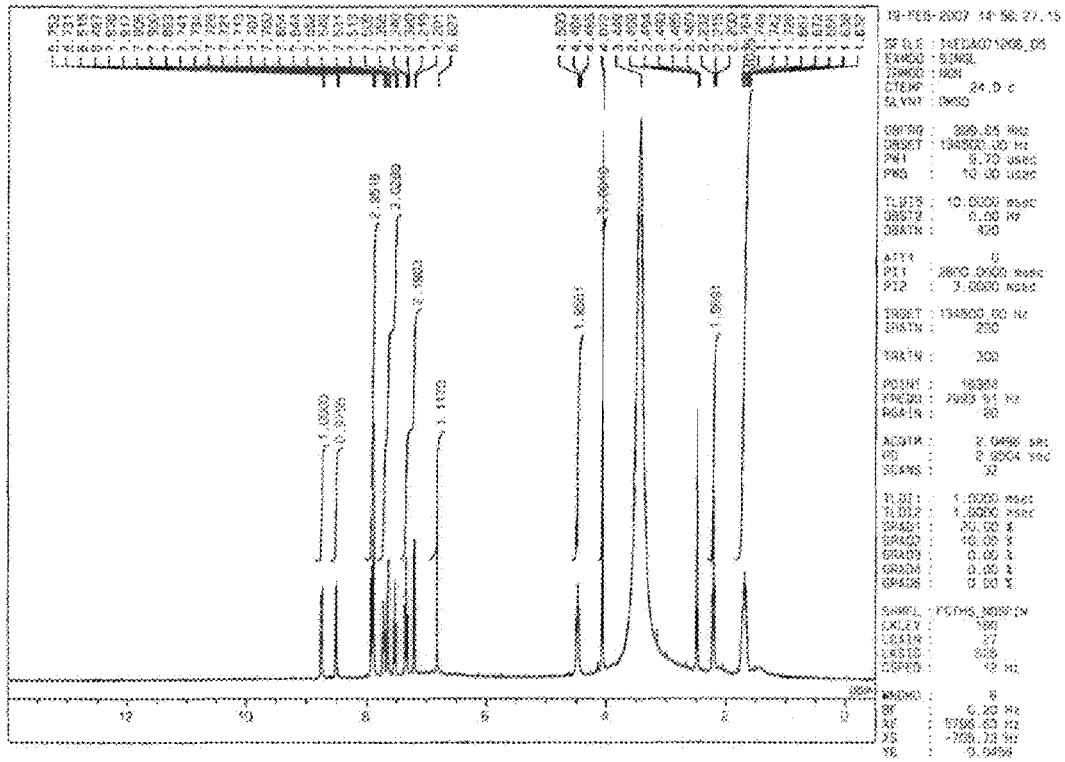
FIG. 6 shows a $^{1}HNMR$ spectrum (DMSO-d6) of a compound (DNA labeled with a dye) of an example.

Next, 1.36 g (5.0 mmol) of N-methylquinolinium iodide (Compound III) (FW 271.10), 7.0 mL (50 mmol) of triethylamine (FW 101.19, d=0.726), and 100 mL of methylene chloride were added to 3.24 g of mixture (crude product) containing Compound 112 (3-(4-carboxybutyl)-2-methylbenzothiazolium bromide) and 2-methylbenzothiazolium bromide. As a result, a transparent solution was obtained. This solution was stirred at 25° C. for 16 hours. Thereafter, the solvent was evaporated under reduced pressure. Acetone (200 mL) then was added to the residue and the precipitate obtained thereby was filtered, which then was washed with acetone. The residue thus obtained was dried under reduced pressure, and the red residue obtained after drying was washed with distilled water (50 mL). This further was filtered, which was washed with distilled water and then dried under reduced pressure. Thus a target substance (Compound 107) was obtained as red powder (654 mg, 1.39 mmol, 28%). This red powder was confirmed to be the target substance (Compound 107) through a comparison in $^1$HNMR spectrum with the reference value. Peak values from $^1$HNMR and $^{13}$CNMR (DMSO-d6) and the measured values of HRMS (ESI) are indicated below. Furthermore, FIG. 6 shows the $^1$HNMR spectrum (DMSO-d6) of Compound 107.

Compound 107: $^1$HNMR (DMSO-d6): δ 8.74 (d, J=8.3 Hz, 1H), 8.51 (d, J=7.3 Hz, 1H), 7.94-7.89 (m, 3H), 7.74-7.70 (m, 1H), 7.65 (d, J=8.3 Hz, 1H), 7.55-7.51 (m, 1H), 7.36-7.32 (m, 1H), 7.21 (d, J=7.3 Hz, 1H), 6.83 (s, 1H), 4.47 (t, J=7.1 Hz, 2H), 4.07 (s, 3H), 2.22 (t, J=6.6 Hz, 1H), 1.77-1.63 (m, 4H); $^{13}$CNMR (DMSO-d6, 60° C.) δ 174.6, 158.8, 148.4, 144.5, 139.5, 137.6, 132.7, 127.9, 126.8, 125.5, 124.1, 123.7, 123.6, 122.4, 117.5, 112.6, 107.6, 87.4, 45.6, 42.0, 35.5, 26.2, 22.3; HRMS (ESI) calcd for $C_{23}H_{23}N_2O_2S$ ([M.Br]$^+$) 391.1480. found 391.1475.

4-((3-(3-carboxypropyl)benzo[d]thiazole-2(3H)-ylidene)methyl)-1-methylquinoliniumbromide with a linker (a polymethylene chain linked to a carboxyl group) having a carbon number n of 3 was synthesized from the mixture of 3-(4-carboxypropyl)-2-methylbenzothiazolium bromide and 2-methylbenzothiazolium bromide by the same method as that used for Compound 107, which was obtained with a yield of 43%. The instrumental analytical values are indicated below.

4-((3-(3-carboxypropyl)benzo[d]thiazole-2(3H)-ylidene)methyl)-1-methylquinoliniumbromide $^1$HNMR (DMSO-d6) δ 8.85 (d, J=8.3 Hz, 1H), 8.59 (d, J=7.3 Hz, 1H), 8.02, 7.93 (m, 3H), 7.78, 7.70 (m, 2H), 7.61, 7.57 (m, 1H), 7.42, 7.38 (m, 1H), 7.31 (d, J=6.8 Hz, 1H), 7.04 (s, 1H), 4.47 (t, J=8.1 Hz, 2H), 4.13 (s, 3H), 2.52, 2.48 (m, 2H), 1.99, 1.92 (m, 2H); $^{13}$CNMR (DMSO-d6, 60° C.) δ 174.3, 158.9, 148.6, 144.5, 139.5, 137.7, 132.7, 127.9, 126.7, 125.6, 124.1, 124.0, 123.7, 122.5, 117.5, 112.5, 107.6, 87.7, 45.6, 42.0, 31.6, 22.4; HRMS (ESI) calcd for $C_{22}H_{21}N_2O_2S$ ([M.Br]$^+$) 377.1324. found 377.1316.

Furthermore, 4-((3-(3-carboxypentyl)benzo[d]thiazole-2(3H)-ylidene) methyl)-1-methylquinoliniumbromide with a linker (a polymethylene chain linked to a carboxyl group) having a carbon number n of 5 was synthesized from the mixture of 3-(4-carboxypentyl)-2-methylbenzothiazolium bromide and 2-methylbenzothiazolium bromide by the same method as that used for Compound 107, which was obtained with a yield of 26%. The instrumental analytical values are indicated below.

4-((3-(3-carboxypentyl)benzo[d]thiazole-2(3H)-ylidene)methyl)-1-methylquinoliniumbromide $^1$HNMR (DMSO-d6) δ 8.70 (d, J=8.3 Hz, 1H), 8.61 (d, J=6.8 Hz, 1H), 8.05, 8.00 (m, 3H), 7.80, 7.73 (m, 2H), 7.60, 7.56 (m, 1H), 7.41, 7.35 (m, 2H), 6.89 (s, 1H), 4.59 (t, J=7.3 Hz, 2H), 4.16 (s, 3H), 2.19 (t, J=7.3 Hz, 1H), 1.82, 1.75 (m, 2H), 1.62, 1.43 (m, 4H); $^{13}$CNMR (DMSO-d6, 60° C.) δ 174.5, 159.0, 148.6, 144.7, 139.7, 137.8, 132.9, 127.9, 126.9, 125.2, 124.2, 123.8, 123.6, 122.6, 117.8, 112.6, 107.7, 87.4, 45.6, 42.1, 36.0, 26.3, 25.9, 24.9; HRMS (ESI) calcd for $C_{24}H_{25}N_2O_2S$ ([M.Br]$^+$) 405.1637. found 405.1632.

Furthermore, 4-((3-(3-carboxyhexyl)benzo[d]thiazole-2(3H)-ylidene) methyl)-1-methylquinoliniumbromide with a linker (a polymethylene chain linked to a carboxyl group) having a carbon number n of 6 was synthesized from the mixture of 3-(4-carboxyhexyl)-2-methylbenzothiazolium bromide and 2-methylbenzothiazolium bromide by the same method as that used for Compound 107, which was obtained with a yield of 22%. The instrumental analytical values are indicated below.

4-((3-(3-carboxyhexyl)benzo[d]thiazole-2(3H)-ylidene)methyl)-1-methylquinoliniumbromide;

$^1$HNMR (DMSO-d6) δ 8.72 (d, J=8.3 Hz, 1H), 8.62 (d, J=6.8 Hz, 1H), 8.07, 8.01 (m, 3H), 7.81, 7.75 (m, 2H), 7.62, 7.58 (m, 1H), 7.42, 7.38 (m, 2H), 6.92 (s, 1H), 4.61 (t, J=7.3 Hz, 2H), 4.17 (s, 3H), 2.18 (t, J=7.3 Hz, 1H), 1.82, 1.75 (m, 2H), 1.51, 1.32 (m, 6H); $^{13}$CNMR (DMSO-d6, 60° C.) δ 174.0, 159.1, 148.6, 144.7, 139.8, 137.8, 132.9, 127.9, 126.8, 125.0, 124.2, 123.8, 123.6, 122.6, 118.0, 112.7, 107.8, 87.4, 45.5, 42.1, 33.4, 27.9, 26.4, 25.5, 24.1; HRMS (ESI) calcd for $C_{25}H_{27}N_2O_2S$ ([M.Br]$^+$) 419.1793. found 419.1788.

(4) Synthesis of N-hydroxysuccinimidyl ester 109

9.4 mg (20 μmol) of 1-methyl-4-[{3-(4-carboxybutyl)-2(3H)-benzothiazolylidene}methyl]quinolinium bromide (Compound 107) (FW 471.41), 4.6 mg (40 μmol) of N-hydroxysuccinimide (Compound 108) (FW 115.09), and 7.6 mg (40 μmol) of EDC (1-ethyl-3-(3-dimethylaminopropyl) carbodiimide hydrochloride) (FW 191.70) were stirred in 1 mL of DMF at 25° C. for 16 hours. Thus N-hydroxysuccinimidyl ester (Compound 109) was obtained, in which the carboxy group of a dye (Compound 107) had been activated. This reaction product was not purified and the reaction solution (20 mM of a dye) was used for the reaction with oligomeric DNA (oligonucleotide) 105 without further being treated.

Furthermore, 4-((3-(4-(succinimidyloxy)-4-oxobutyl)benzo[d]thiazole-2(3H)-ylidene)methyl)-1-methylquinolinium bromide with a linker (a polymethylene chain) having a carbon number n of 3 was synthesized by the same method as that used for Compound 109 except for a compound with a linker (a polymethylene chain) having a different carbon number was used instead of Compound 107 as a raw material. Moreover, 4-((3-(4-(succinimidyloxy)-4-oxohexyl)benzo[d]thiazole-2(3H)-ylidene)methyl)-1-methylquinolinium bromide with a linker (a polymethylene chain) having a carbon number n of 5 and 4-((3-(4-(succinimidyloxy)-4-oxoheptyl)benzo[d]thiazole-2(3H)-ylidene)methyl)-1-methylquinolinium bromide with a linker (a polymethylene chain) having a carbon number n of 6 were synthesized in the same manner.

Figure 7:
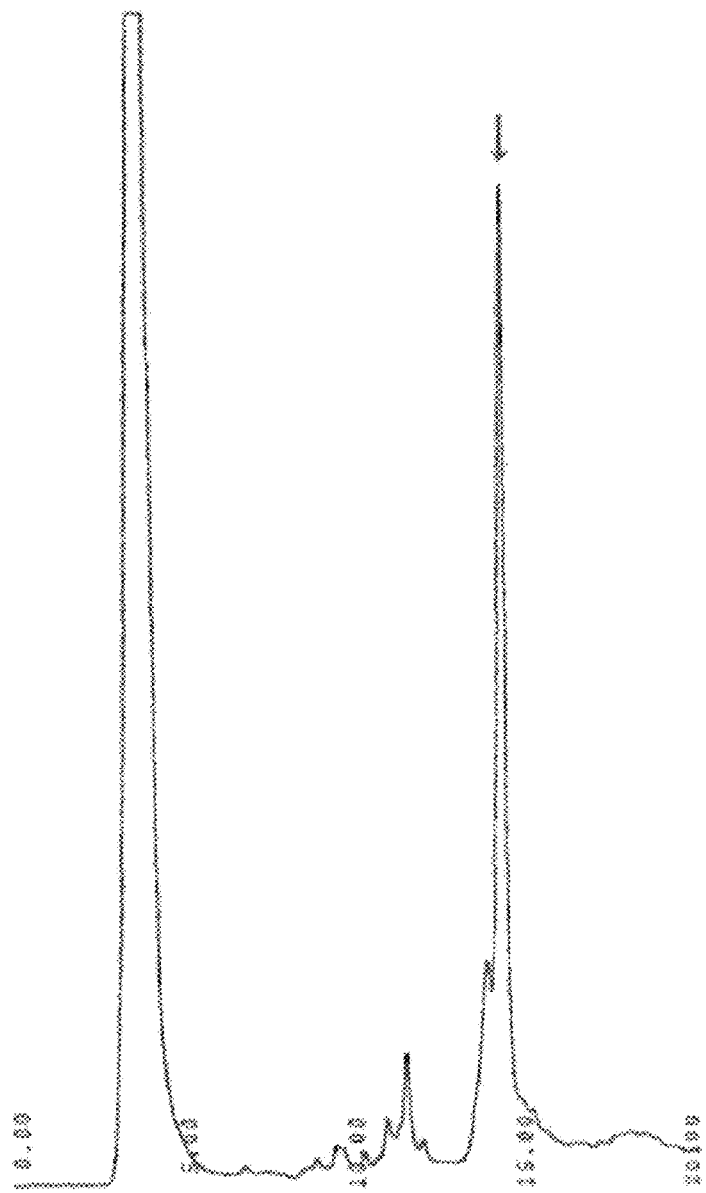
FIG. 7 shows a chart of reversed-phase HPLC of the compound (DNA labeled with a dye) shown in FIG. 6.
Figure 8:
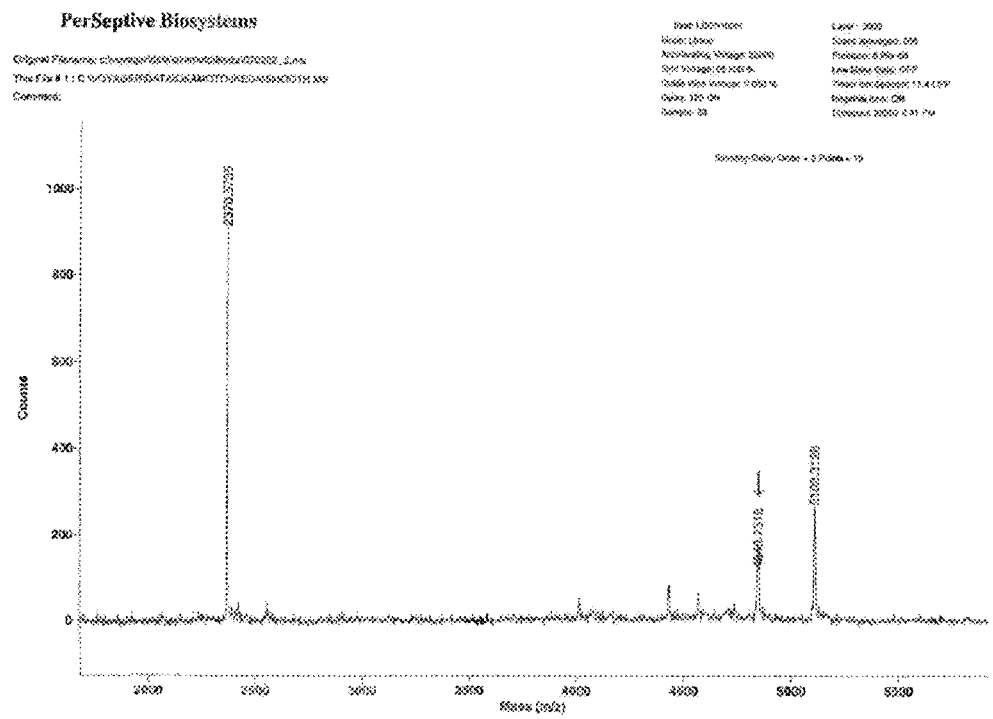
FIG. 8 shows a MALDI-TOF mass spectrum of the compound (DNA labeled with a dye) shown in FIG. 6.

(5) Synthesis of DNA Oligomer (Oligonucleotide) 110) modified with 2 Molecules of Thiazole Orange A DNA oligomer (oligonucleotide) 105 having two active amino groups was synthesized by a conventional method with an automated DNA synthesizer in the same manner as in Example 4. The sequence of Compound 105 used herein was the same as that used in Example 4, specifically, 5'-d(CGCAATXTAACGC)-3' (X was Compound 104). Next, this DNA oligomer (oligonucleotide) 105 was reacted with N-hydroxysuccinimidyl ester (Compound 109) and thereby DNA oligomer (oligonucleotide) 110 was synthesized having, in one molecule, structures derived from thiazole orange in two places. That is, first, 30 μL of 5'-d(CGCAATXTAACGC)-3' (Compound 105, with a strand concentration of 320 μM), 10 μL of $Na_2CO_3/NaHCO_3$ buffer (1 M, pH 9.0), and 60 μL of $H_2O$ were mixed together. Thereafter, 100 μL of DMF solution (20 mM) of N-hydroxysuccinimidyl ester (Compound 109) was added thereto and mixed well. This was allowed to stand still at 25° C. for 16 hours. Thereafter, 800 μL of $H_2O$ was added thereto, which then was passed through a 0.45-μm filter. The peak that appeared after about 14.5 minutes in reversed-phase HPLC was purified (CHEMCOBOND 5-ODS-H 10×150 mm, 3 mL/min, 5-30% $CH_3CN$/50 mM TEAA buffer (20 minutes), detected at 260 nm). FIG. 7 shows the chart of the reversed-phase HPLC. The fraction indicated with the peak marked with an arrow was fractionated and purified. The product thus obtained by HPLC purification was measured with a MALDI TOF mass spectrometer in its negative mode. As a result, a peak was observed at 4848.8, and it was confirmed to be DNA oligomer (oligonucleotide) 110. FIG. 8 shows the MALDI TOF MASS spectrum of the DNA oligomer (oligonucleotide) 110. In FIG. 8, the arrow indicates the mass peak (4848.8) derived from the purified product. This peak value agreed with a calculated value of 4848.8 of $[M^{2+}-3H^+]^-$ in which three protons were removed from a molecule $M(C_{180}H_{220}N_{56}O_{78}P_{12}S_2)$ of DNA oligomer (oligonucleotide) 110 having two positive charges. The peaks located on the left and right sides thereof are derived from T8-mer and T18-mer of DNA that were added as standard substances.

Example 7

Use of DNA Oligomer (Oligonucleotide) 110 as Fluorescence Probe

Figure 9:
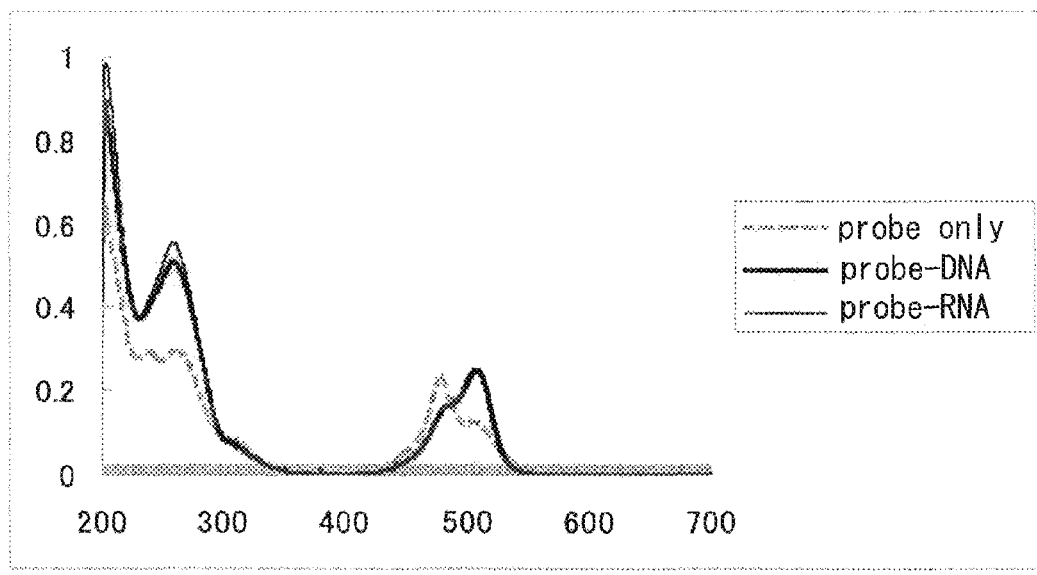
FIG. 9 shows UV spectra of three samples of a fluorescent probe according to an example that were in a single strand state, a DNA-DNA double helix state, and a DNA-RNA double helix state, respectively.

DNA oligomer (oligonucleotide) 110 (DNA with two molecules of dye) purified in Example 6 was desalted and lyophilized. Thereafter, an aqueous solution thereof was prepared, and the concentration thereof was determined according to UV absorption (X was approximated by V. Thereafter, UV measurement was carried out with respect to the fluorescence probe (DNA oligomer 110) under conditions including a strand concentration of 2.5 µM, 50 mM phosphoric acid buffer (pH 7.0), and 100 mM NaCl, with the fluorescence probe being in a single strand state, a DNA-DNA double helix state, and a DNA-RNA double helix state. FIG. 9 shows spectra of those three samples. In FIG. 9, the dotted line shows the spectrum obtained when the fluorescence probe was in the single strand state, the thick line shows the spectrum obtained when the fluorescence probe was in the DNA-DNA double helix state, and the thin line shows the spectrum obtained when the fluorescence probe was in the DNA-RNA double helix state. As shown in FIG. 9, the maximum wavelength of UV absorption around 500 nm moved when the double helices were formed. In FIG. 9 and every other UV absorption spectrum, the horizontal axis indicates the wavelength (nm) and the vertical axis indicates the absorbance.

Figure 10:
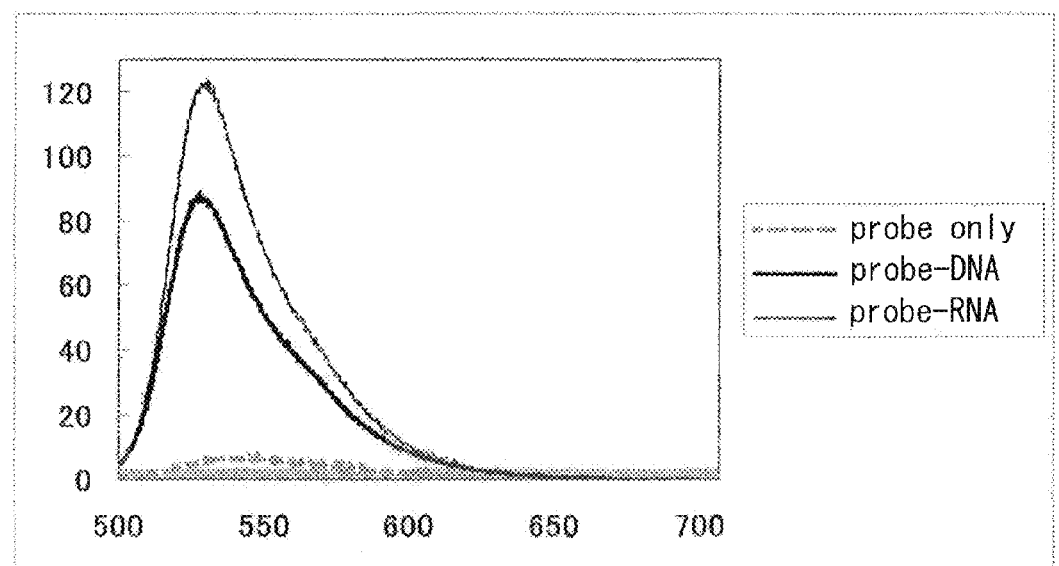
FIG. 10 shows fluorescence spectra of the three samples of the fluorescent probe shown in FIG. 9 that were in a single strand state, a DNA-DNA double helix state, and a DNA-RNA double helix state, respectively, which were obtained using excitation light with a wavelength of 488 nm.

Next, the fluorescence probe was excited with excitation light (bandwidth: 1.5 nm) with a wavelength of 488 nm under the same conditions including a strand concentration of 2.5 µM, 50 mM phosphoric acid buffer (pH 7.0), and 100 mM NaCl. Thereafter, fluorescence measurement was carried out. FIG. 10 shows spectra of three samples of the fluorescence probe in a single strand state (dotted line), a DNA-DNA double helix state (thick line), and a DNA-RNA double helix state (thin line), respectively. As shown in FIG. 10, when compared with the fluorescence intensity of the single-stranded fluorescence probe obtained at 530 nm, the fluorescence intensity increased 15 times in the case of the DNA-DNA double helix and 22 times in the case of the DNA-RNA double helix. In FIG. 10 and every other fluorescence emission spectrum, and in excitation spectra, the horizontal axis indicates the wavelength (nm) and the vertical axis indicates the emission intensity.

Figure 11:
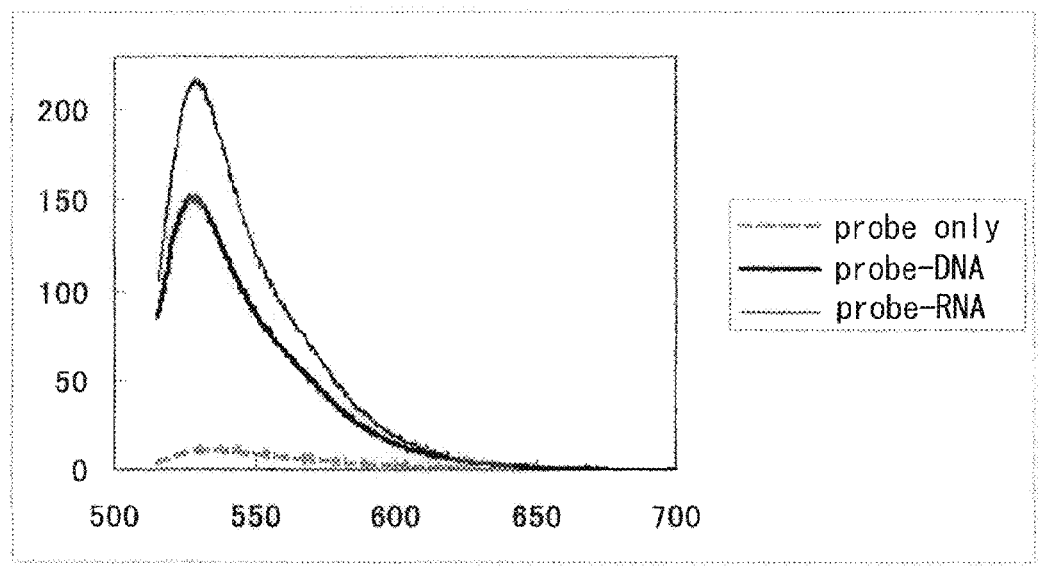
FIG. 11 shows fluorescence spectra of the three samples of the fluorescent probe shown in FIG. 9 that were in a single strand state, a DNA-DNA double helix state, and a DNA-RNA double helix state, respectively, which were obtained using excitation light with a wavelength of 510 nm.

Furthermore, the same results were obtained when excitation light with a wavelength of 510 nm was used instead of the excitation light with a wavelength of 488 nm. FIG. 11 shows the spectra thereof.

Example 8

Synthesis of Compounds with Linkers Having Lengths Changed Variously and Use Thereof as Fluorescence Probe Compounds (DNA oligomers) represented by Chemical Formula 113 shown below were synthesized with the linker lengths n being changed variously. The compounds were synthesized in the same manner as in Examples 1 to 4 and 6 except that the compounds were prepared, in each of which the carbon number (chain length) of 5-bromovaleric acid (5-bromopentanoic acid) used as a raw material was changed according to the linker length. In this example, the sequence of Compound 113 was 5'-d(CGCAATXTAACGC)-3' (X was the site where a dye was introduced). Furthermore, each compound was used as a fluorescence probe in the same manner as in Example 7, and the performance thereof was evaluated through fluorescence measurement. As a result, it was proved that when the probe hybridizes with a target nucleic acid, the fluorescence increased approximately 10 times or more than that of a single-stranded probe, as long as the linker has a length in the range indicated below. Moreover, the double strand formed of the probe and target nucleic acid exhibited higher thermal stability than that of a double strand with a native sequence.

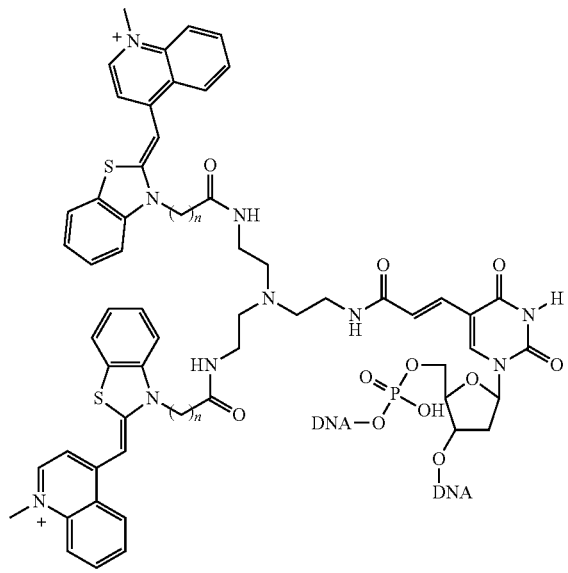

113

TABLE 1

|  |  | $\lambda_{max}$ (nm) of UV and absorption coefficient | $\lambda_{max}$ (nm) of fluorescence | Quantum yield $\Phi_F$ | Fluorescence intensity ratio $I_{ds}/I_{ss}$ between double strand and single strand | Tm (° C.) |
|---|---|---|---|---|---|---|
| n = 3 | Probe Single strand | 480(117000) 510(93800) | 537 | 0.0193 | — | None |
|  | Probe-DNA Double strand | 505(145000) | 529 | 0.137 | 7.1 | 66 |
|  | Probe-RNA Double strand | 506(139000) | 529 | 0.161 | 8.3 | 54 |

TABLE 1-continued

| | | $\lambda_{max}$ (nm) of UV and absorption coefficient | $\lambda_{max}$ (nm) of fluorescence | Quantum yield $\Phi_F$ | Fluorescence intensity ratio $I_{ds}/I_{ss}$ between double strand and single strand | Tm (° C.) |
|---|---|---|---|---|---|---|
| n = 4 | Probe Single strand | 479(156000) 509(104000) | 537 | 0.0105 | — | None |
| | Probe-DNA Double strand | 509(179000) | 529 | 0.110 | 10.5 | 65 |
| | Probe-RNA Double strand | 509(171000) | 529 | 0.116 | 11.0 | 52 |
| n = 5 | Probe Single strand | 480(139000) 510(107000) | 538 | 0.0131 | — | None |
| | Probe-DNA Double strand | 508(172000) | 529 | 0.123 | 9.4 | 67 |
| | Probe-RNA Double strand | 508(162000) | 529 | 0.126 | 9.6 | 51 |
| n = 6 | Probe Single strand | 479(139000) 509(93300) | 536 | 0.0122 | — | None |
| | Probe-DNA Double strand | 509(164000) | 528 | 0.122 | 10.0 | 65 |
| | Probe-RNA Double strand | 511(162000) | 530 | 0.129 | 10.6 | 52 |

```
5'-d(CGCAATTTAACGC)-3'/5'-d(GCGTTAAATTGCG)-3'
Tm(° C.) 58

5'-d(CGCAATTTAACGC)-3'/5'-r(GCGUUAAAUUGCG)-3'
Tm(° C.) 46
```

Measurement conditions: 2.5 μM probe (Compound 113), 50 mM phosphoric acid buffer (pH 7.0), 100 mM NaCl, 2.5 μM complementary strand The maximum wavelength of fluorescence was the value obtained when excitation was carried out with a light having a wavelength of 488 nm (1.5 nm width). The quantum yield was calculated with 9,10-diphenylanthracene being used as a reference substance.

Figure 12:
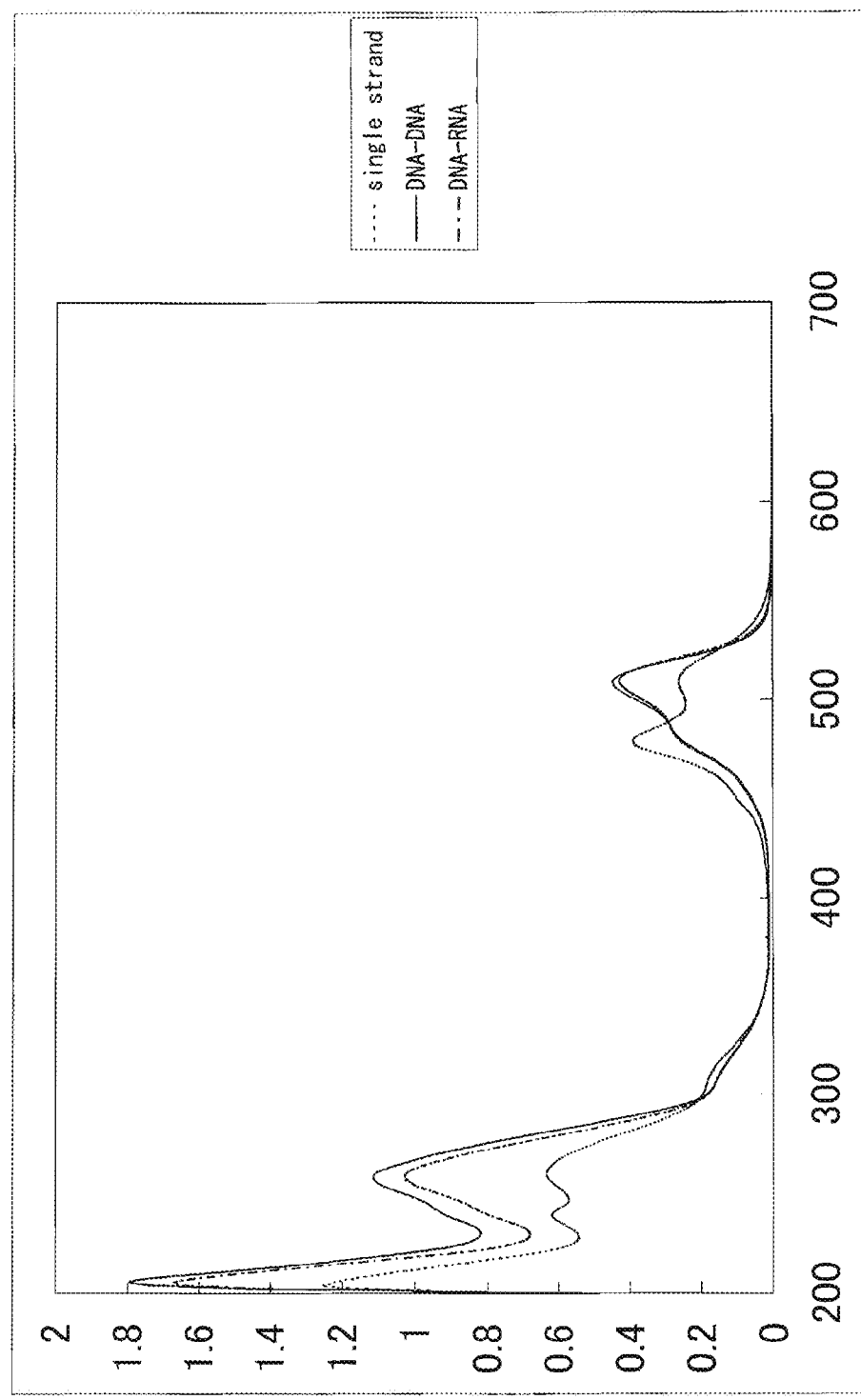
FIG. 12 shows UV spectra of three samples of a fluorescent probe according to another example that were in a single strand state, a DNA-DNA double helix state, and a DNA-RNA double helix state, respectively.

FIG. 12 shows absorption spectra obtained with the linker length n being 4 in Example 8. The dotted line shows the spectrum of the single strand, the solid line shows the spectrum of the DNA-DNA strand, and the chain line shows the spectrum of the DNA-RNA strand. When attention is drawn to absorption that occurred at 400 to 600 nm, the absorption band obtained in the single-stranded state appeared on the shorter wavelength side as compared to the absorption band obtained after hybridization. This clearly indicates the formation of an H-aggregate of dye dimer in the single-stranded state.

Figure 13:
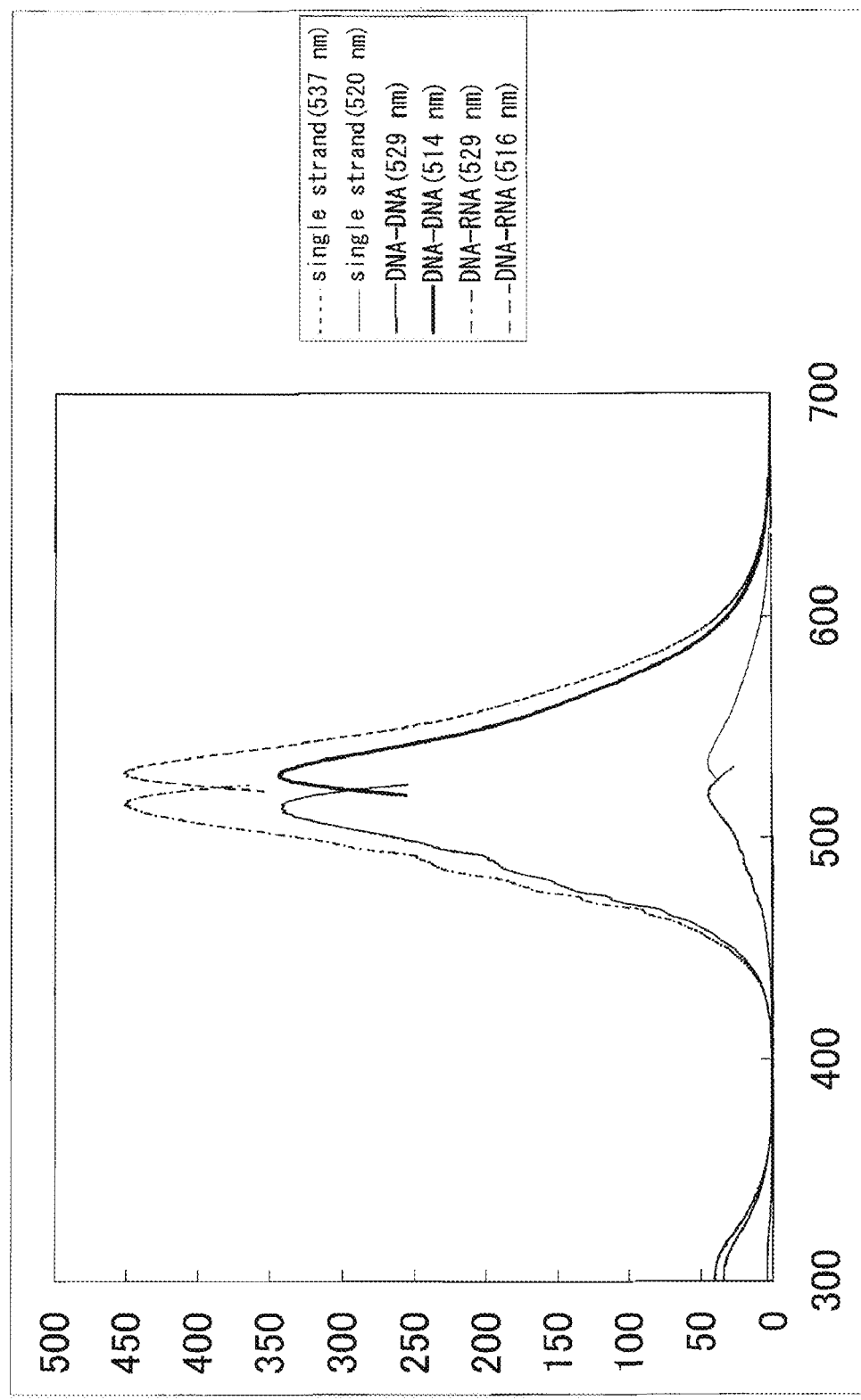
FIG. 13 shows fluorescence spectra of the three samples of the fluorescent probe shown in FIG. 12 that were in a single strand state, a DNA-DNA double helix state, and a DNA-RNA double helix state, respectively.

FIG. 13 shows both the fluorescence emission spectra and excitation spectra obtained with a linker length n being 4 in Example 8. In FIG. 13, the curves located on the left side (the shorter wavelength side) indicate the excitation spectra while the curves located on the right side (the longer wavelength side) indicate the fluorescence emission spectra. In FIG. 13, the wavelength of reference fluorescence emission ($\lambda_{max}$ of fluorescence) with respect to the excitation spectra and the excitation wavelength with respect to the fluorescence emission spectra are indicated in parentheses in the explanatory note. In both the excitation spectra and the fluorescence emission spectra, the single strand exhibited the lowest emission intensity, the DNA-DNA strand exhibited the emission intensity higher than that of the single strand, and the DNA-RNA strand exhibited the highest emission intensity. From the excitation spectra, it was proved that the absorption associated with fluorescence emission was only that in the absorption band on the longer wavelength side shown in FIG. 12 and the absorption on the shorter wavelength side was not associated with fluorescence emission. That is, it clearly indicates that the fluorescence emission was suppressed by the exciton effect. Accordingly, fluorescence emission was strong after hybridization, while it was very weak in the single-stranded state. This allows the states before and after hybridization to be differentiated clearly from each other.

Example 9

Compounds (DNA oligomers) represented by Chemical Formula 114 below, each of which contained, in one molecule, one dye structure alone, were synthesized with the linker lengths n being changed variously. The compounds were synthesized in the same manner as in Example 1 to 4 and 6 except that the compounds were prepared, in each of which the carbon number (chain length) of 5-bromovaleric acid (5-bromopentanoic acid) used as a raw material was changed according to the linker length, and bis(2-aminoethyl)methylamine was used instead of tris(2-aminoethyl)amine used in synthesizing Compound 102. Compounds with n being 3, 4, 5, and 6, were synthesized in the same manner.

114

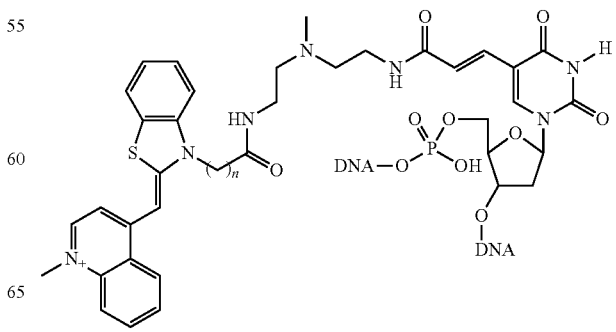

More specifically, the synthesis was carried out according to the following scheme. The following scheme shows the case where n=4, but the synthesis was carried out in the same manner even when n was another numerical value.
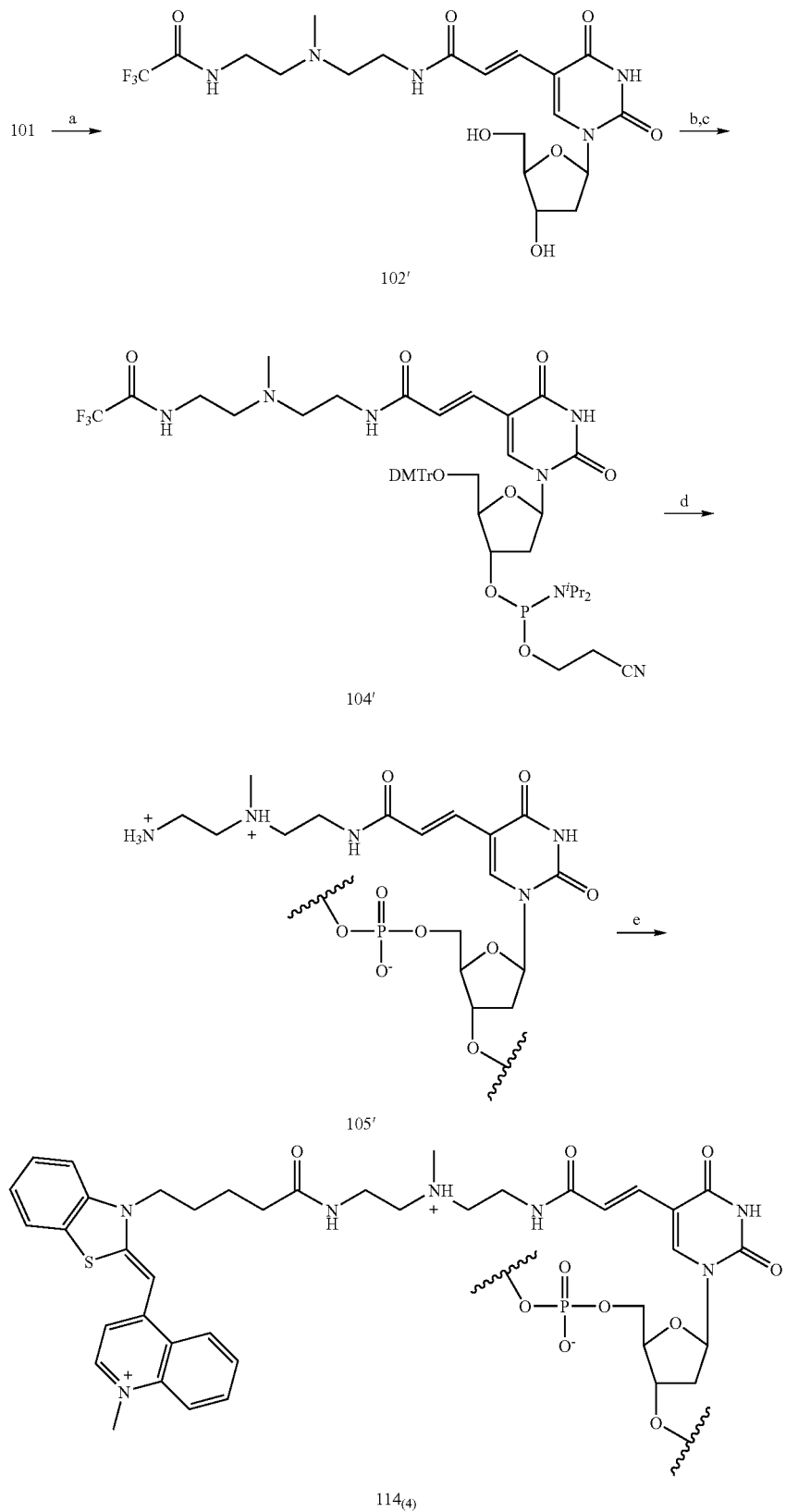

Synthesis of (E)-5-(3-(2-(N-Methyl-N-(2-(2,2,2-trifluoroacetamido) ethyl)amino)ethylamino)-3-oxo-prop-1-enyl)-2'-deoxyuridine (102')

First, 1.19 g (4.0 mmol) of (E)-5-(2-carboxyvinyl)-2'-deoxyuridine 101 (with a molecular weight of 298.25), 921 mg (8.0 mmol) of N-hydroxysuccinimide (with a molecular weight of 115.09), and 1.53 g (8.0 mmol) of 1-ethyl-3-(3-dimethylaminopropyl)carbodiimide (with a molecular weight of 191.70) were placed in a recovery flask containing a stirring bar. Thereafter, 1.0 mL of DMF was added thereto, which was stirred at 25° C. for eight hours. Approximately 1 mL of acetic acid was added thereto, and 250 mL of methylene chloride and 250 mL of ultrapure water further were added thereto, which then was stirred vigorously. The precipitate produced thereby was filtered, washed with water, and dried under reduced pressure throughout the night. The white residue thus obtained was suspended in 100 mL of acetonitrile, which was stirred vigorously. Subsequently, 2.34 g (20 mmol) of N-methyl-2,2'-diaminodiethylamine (with a molecular weight of 146.23, d=0.976) was added thereto all at once, which further was stirred at 25° C. for 10 minutes. Thereafter, 4.8 mL (40 mmol) of ethyl trifluoroacetate (with a molecular weight of 142.08, d=1.194), 5.6 mL (40 mmol) of triethylamine (with a molecular weight of 101.19, d=0.726), and 50 mL of ethanol were added thereto, which was stirred at 25° C. for 16 hours. From the mixture thus obtained, the solvent was evaporated under reduced pressure, which was then purified in a silica gel column (10-20% MeOH/$CH_2Cl_2$). From the fraction containing the target substance, the solvent was evaporated under reduced pressure. The product produced thereby was dissolved in a small amount of acetone, and ether then was added thereto. As a result, white precipitate was produced. This was filtered, washed with ether, and then dried under reduced pressure. Thus 750 mg (76%) of target substance (Compound 102') was obtained as white powder. The instrumental analytical values are indicated below.

Compound 102':
$^1$HNMR ($CD_3OD$) δ 8.29 (s, 1H), 7.17 (d, J=15.6 Hz, 1H), 6.97 (d, J=15.6 Hz, 1H), 6.21 (t, J=6.3 Hz, 1H), 4.40, 4.36 (m, 1H), 3.92, 3.90 (m, 1H), 3.80 (dd, J=11.7, 2.9 Hz, 1H), 3.72 (dd, J=11.7, 3.4 Hz, 1H), 3.37, 3.25 (m, 5H), 2.60, 2.53 (m, 5H), 2.33, 2.19 (m, 5H); $^{13}$CNMR ($CD_3OD$) δ 169.2, 158.7 (q, J=36.4 Hz), 151.2, 143.7, 143.6, 134.1, 122.2, 117.5 (q, J=286.2 Hz), 111.0, 89.2, 87.0, 72.1, 62.6, 57.4, 56.7, 42.4, 41.8, 38.5, 38.3; HRMS (ESI) calcd for $C_{19}H_{27}F_3N_5O_7$ ([M+H]$^+$) 494.1863. found 494.1854.

Synthesis of (E)-5-(3-(2-(N-Methyl-N-(2-(2,2,2-trifluoroacetamido) ethyl)amino)ethylamino)-3-oxo-prop-1-enyl)-5'O-(4,4'-dimethoxytrityl)-2'-deoxyuridine 3'O-(2-cyanoethyl)-N,N-diisopropylphosphoramidite (Compound 104')

First, 296 mg (0.60 mmol) of Compound 102' (with a molecular weight of 494.19) and 224 mg (0.66 mmol) of 4,4'-dimethoxytritylchloride (with a molecular weight of 338.83) were placed in a recovery flask containing a stirring bar. Thereafter, 4 mL of pyridine was added thereto, which was stirred at 25° C. for two hours. Subsequently, 1 mL of water was added thereto, and the solvent was then evaporated under reduced pressure. The product obtained thereby was purified in a silica gel column (1.5% MeOH and 1% $Et_3N$/$CH_2Cl_2$). A fraction containing tritylide (an intermediate of Compound 104') of the target compound 102' was concentrated, and a saturated sodium bicarbonate aqueous solution was added to the residue. The mixture was extracted with ethyl acetate, washed with saturated saline, and dried under reduced pressure. Thus white foamy tritylide (366 mg, 77%) was obtained.

$^1$HNMR ($CD_3OD$) δ 7.94 (s, 1H), 7.42, 7.17 (m, 9H), 7.01 (d, J=15.6 Hz, 1H), 6.95 (d, J=15.6 Hz, 1H), 6.86, 6.83 (m, 4H), 6.21 (t, J=6.3 Hz, 1H), 4.41, 4.38 (m, 1H), 4.09, 4.06 (m, 1H), 3.75 (s, 6H), 3.40, 3.30 (m, 6H), 2.59 (t, J=6.8 Hz, 2H), 2.53 (t, J=6.8 Hz, 2H), 2.46, 2.31 (m, 5H); $^{13}$CNMR ($CD_3OD$) δ 169.2, 158.7 (q, J=36.4 Hz), 151.2, 143.7, 143.6, 134.1, 122.2, 117.5 (q, J=286.2 Hz), 111.0, 89.2, 87.0, 72.1, 62.6, 57.4, 56.7, 42.4, 41.8, 38.5, 38.3; HRMS (ESI) calcd for $C_{40}H_{45}F_3N_5O_9$ ([M+H]$^+$) 796.3169. found 796.3166.

In a round-bottom flask were placed 159 mg (0.20 mmol) of tritylide (with a molecular weight of 920.85) of Compound 102' and 28.6 mg (0.40 mmol) of 1H-tetrazole (with a molecular weight of 70.05). This was vacuum-dried with a vacuum pump overnight. Then, 4.0 mL of $CH_3CN$ was added thereto and thereby the product thus dried was dissolved therein, which then was stirred. Thereafter, 191 μL (0.60 mmol) of 2-cyanoethyl N,N,N',N'-tetraisopropylphosphoramidite (with a molecular weight of 301.41, d=0.949) was added thereto all at once, which was stirred at 25° C. for two hours. After reaction completion was confirmed by TLC, saturated sodium bicarbonate water was added thereto, which was extracted with ethyl acetate. The organic layer obtained thereby was washed with saturated saline and then dried with magnesium sulfate. After the magnesium sulfate was removed by filtration, the solvent was evaporated under reduced pressure. Thus a crude product containing the target compound 104' was obtained. This composition was used for DNA synthesis without being purified or further treated. From $^{31}$PNMR ($CDCl_3$) and HRMS (ESI) of the crude product, it was confirmed that Compound 104' had been obtained. Those values are indicated below.

Compound 104';
$^{31}$PNMR ($CDCl_3$) δ 149.686, 149.393; HRMS (ESI) calcd for $C_{49}H_{61}F_3N_7O_{10}P$ ([M+H]$^+$) 996.4248. found 996.4243.

DNA 105' was synthesized in the same manner as in the case of Compound 105. The instrumental analytical values are indicated below.

DNA 105';
CGCAAT[105']TAACGC, calcd for $C_{133}H_{174}N_{51}O_{76}P_{12}$ ([M+H]$^+$) 4074.8. found 4072.0; CGCAAT[105'][105'] AACGC, calcd for $C_{140}H_{187}N_{54}O_{77}P_{12}$ ([M+H]$^+$) 4230.0. found 4228.9.

DNA 114 containing thiazole orange introduced therein was synthesized in the same manner as in the case of Compound 113. The instrumental analytical values are indicated below.

CGCAAT[114]$_{(4)}$TAACGC, calcd for $C_{156}H_{194}N_{53}O_{77}P_{12}S$(M$^+$) 4447.3. found 4445.6; CGCAAT [114]$_{(4)}$[114]$_{(4)}$AACGC, calcd for $C_{186}H_{228}N58O_{79}P_{12}S_2$ ([M.H]$^+$) 4976.0. found 4976.9.

Figure 14:
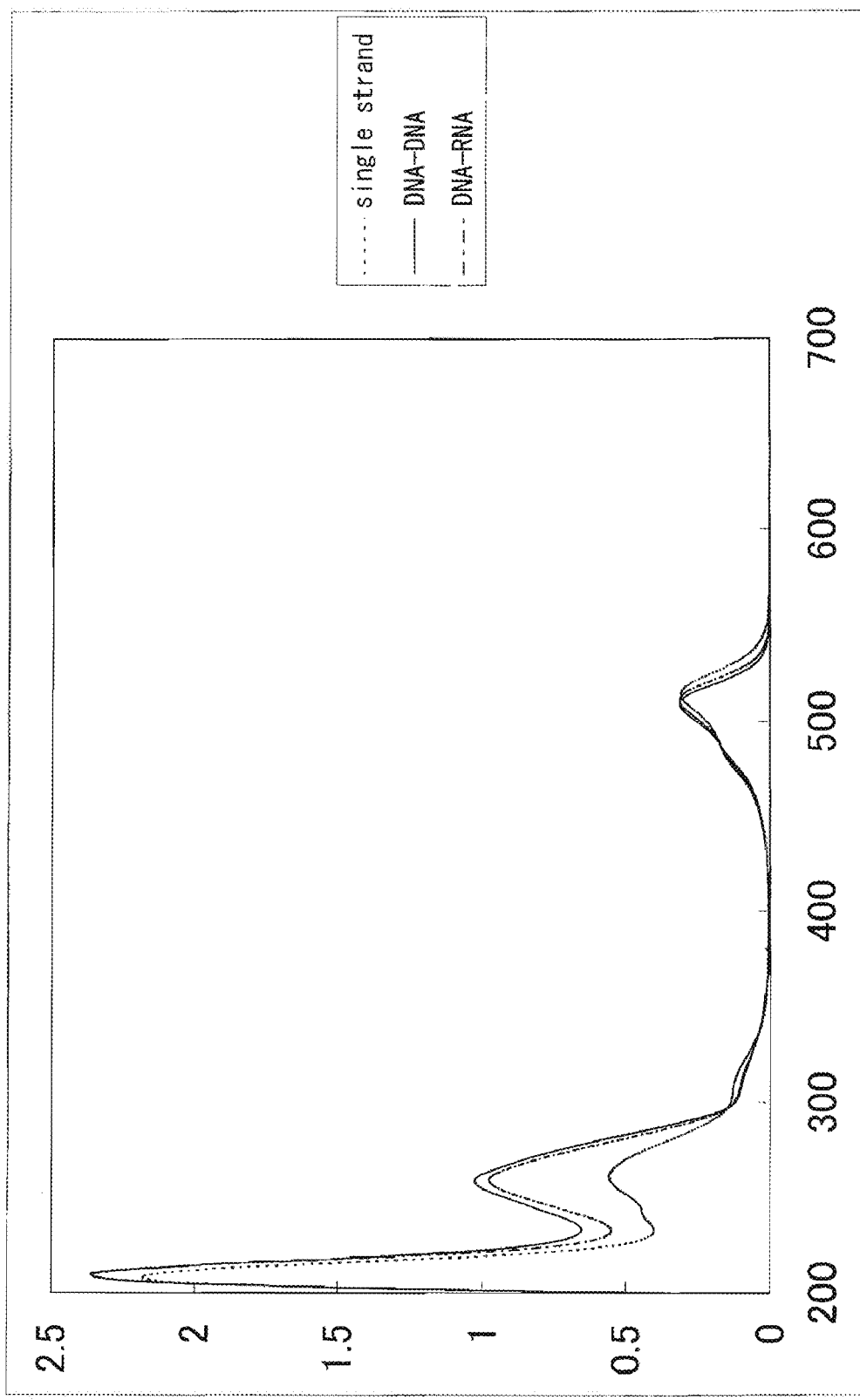
FIG. 14 shows UV spectra of three samples of a fluorescent probe according to still another example that were in a single strand state, a DNA-DNA double helix state, and a DNA-RNA double helix state, respectively.
Figure 15:
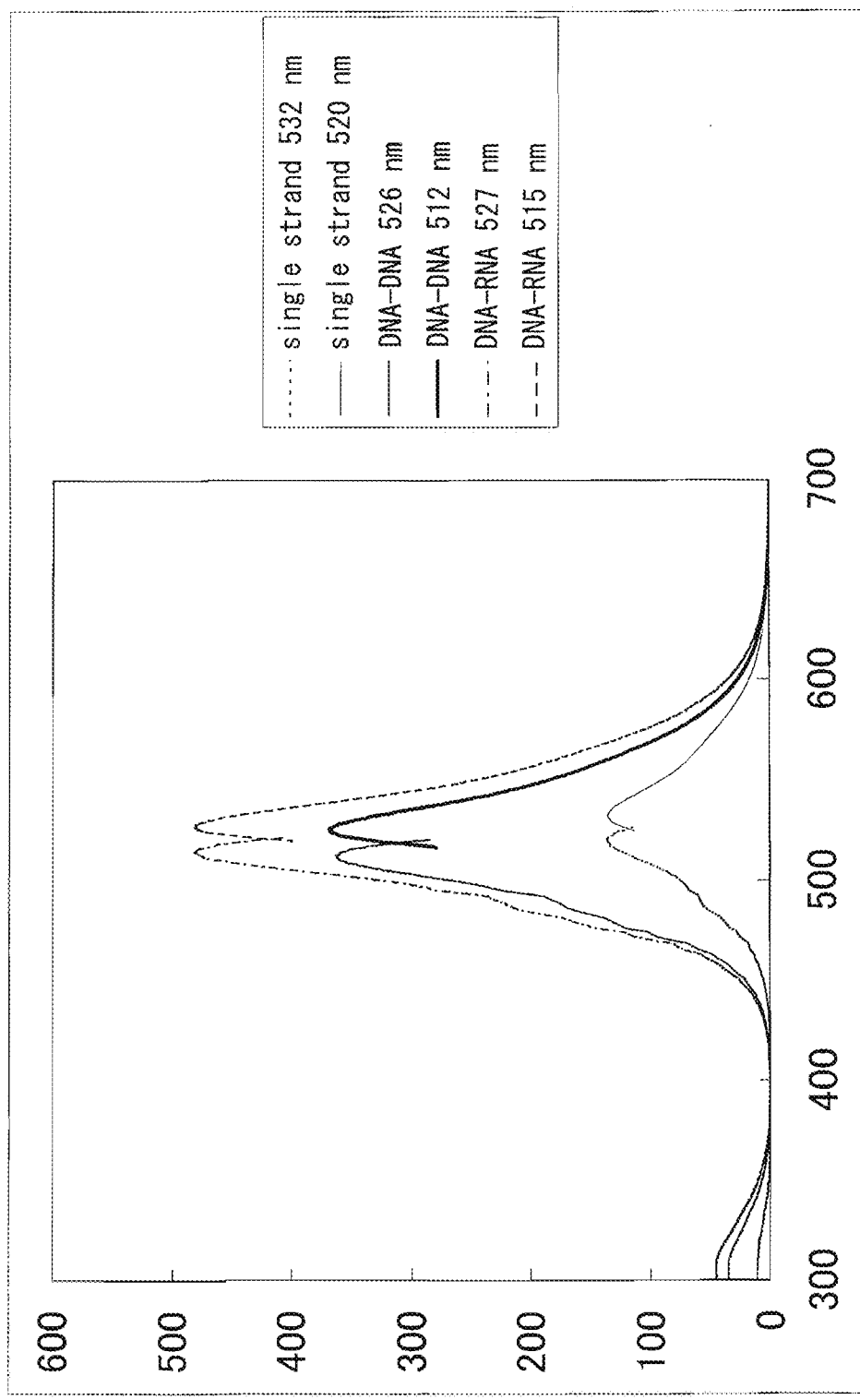
FIG. 15 shows fluorescence spectra of the three samples of the fluorescent probe shown in FIG. 14 that were in a single strand state, a DNA-DNA double helix state, and a DNA-RNA double helix state, respectively.

With respect to ODN (a probe containing only one dye) having a sequence of 5'-d(CGCAAT[114]$_{(n)}$TAACGC)-3' selected from the synthesized DNA oligomers (ODNs), fluorescence behavior was observed in the same manner as in Examples 7 and 8. The results are indicated in Table 2 below and FIGS. 14 and 15. FIG. 14 shows the absorption spectra (the dotted line shows the spectrum of the single strand, the solid line shows the spectrum of the DNA-DNA strand, and the chain line shows the spectrum of the DNA-RNA strand), and FIG. 15 shows the excitation spectra and emission spectra. In FIG. 15, the curves located on the left side (the shorter wavelength side) indicate the excitation spectra while the curves located on the right side (the longer wavelength side) indicate the fluorescence emission spectra. In FIG. 15, the wavelengths indicated in the explanatory note denote the wavelength of reference fluorescence emission ($\lambda_{max}$ of fluorescence) with respect to the excitation spectra and the excitation wavelength with respect to the fluorescence emission spectra, respectively. In both the excitation spectra and the fluorescence emission spectra, the single strand exhibited the lowest emission intensity, the DNA-DNA strand exhibited the emission intensity higher than that of the single strand, and the DNA-RNA strand exhibited the highest emission intensity. As shown in FIGS. 14 and 15, Compound 114 has, in one molecule, only one dye structure and therefore no H-aggregate is formed. Thus the exciton effect does not occur (no shift towards the shorter wavelength side is observed in the absorption spectrum). Accordingly, fluorescence quenching was weaker in the single-stranded state as compared to the compounds containing two dye structures, and the fluorescence intensity ratio $I_{ds}/I_{ss}$ between the double strand and the single strand is relatively low. However, since the intercalation of dye through formation of a double strand planarizes the dye structure, higher fluorescence intensity was obtained in the double-stranded state as compared to the single strand as indicated in Table 2 below. In the single strand, when the excitation wavelength was changed from 488 nm to $\lambda_{max}$ (one on the longer wavelength side if there are two $\lambda_{max}$) in the UV absorption spectrum, a quantum yield $\Phi_F$ of 0.120 was obtained as a measurement result. Furthermore, in the DNA-DNA double strand, when the excitation wavelength was changed from 488 nm to $\lambda_{max}$ (one on the longer wavelength side if there are two $\lambda_{max}$) in the UV absorption spectrum, a quantum yield $\Phi_F$ of 0.307 and a fluorescence intensity ratio $I_{ds}/I_{ss}$ between the double strand and the single strand of 3.4 were obtained as measurement results.

TABLE 2

| | | $\lambda_{max}$ (nm) of UV and absorption coefficient | $\lambda_{max}$ (nm) of fluorescence | Quantum yield | Ratio | Tm (° C.) |
|---|---|---|---|---|---|---|
| n = 4 | Single strand | 515(123000) | 532 | 0.0681 | — | None |
| | DNA-DNA Double strand | 509(125000) | 526 | 0.180 | 2.64 | 65 |
| | DNA-RNA Double strand | 511(125000) | 527 | 0.244 | 3.58 | 55 |

Measurement conditions: 2.5 µM probe, 50 mM phosphoric acid buffer (pH 7.0), 100 mM NaCl, 2.5 µM complementary strand The maximum wavelength of fluorescence is a value obtained when excitation was carried out with light having a wavelength of 488 nm (with a width of 1.5 nm).

The quantum yield was calculated with 9,10-diphenylanthracene being used as a reference substance.

Example 10

Compounds (DNA oligomers), each of which contains only one dye structure in one molecule, were synthesized in the same manner as in Example 9 except that a compound represented by Chemical Formula 115 was used as a dye instead of Compound 107. The synthesis was carried out with the linker length n being changed variously from 1 to 4. The sequence was 5'-d(CGCAATXTAACGC)-3' (X was the site where a dye was introduced) as in Compound 105.

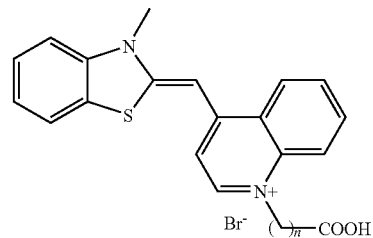

Compound 116 indicated below is obtained when n=2. Fluorescence intensity of Compound 116 was evaluated in the same manner as in Examples 7 to 9. As a result, in the case of the DNA-RNA double strand, the increase in fluorescence intensity was observed as compared to the case of the single strand.

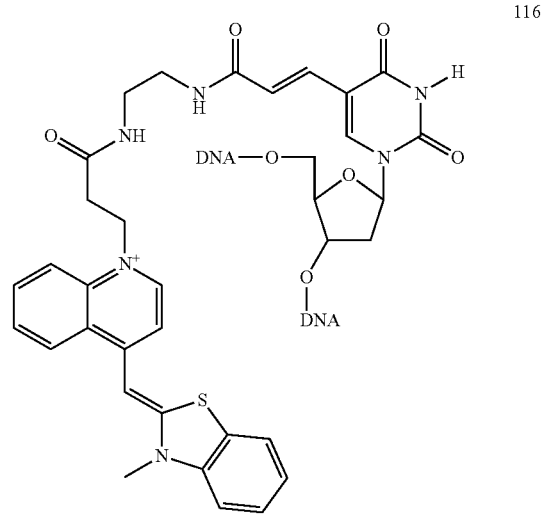

[Fluorescence Lifetime Measurement]

With respect to the DNA oligomers (oligonucleotides) of Example 8 (two dyes) and Example 9 (one dye), fluorescence lifetime was measured in the case of the single strand and in the case of the double-strand DNA, respectively. The DNA oligomer used as a measurement control contains, in the site X in the following sequence, a nucleotide containing a dye introduced therein.

```
5'-d(CGCAATXTAACGC)-3'    (SEQ ID NO. 1)

5'-d(GCGTTAAATTGCG)-3'    (SEQ ID NO. 2)
```

The results of the fluorescence lifetime measurement are indicated in Table 3 below. In Table 3, T is fluorescence lifetime (ns). CHISQ denotes a measurement error. T1 indicates the time elapsed from immediately after completion of excitation. T2 indicates the time further elapsed after time T1 has elapsed in the case of the probe containing two dyes of Example 8 while being the time elapsed from immediately after completion of excitation in the case of the probe containing one dye of Example 9. T3 indicates the time further elapsed after time T2 has elapsed. In Table 3, the numerical value expressed in "%" is the fluorescence decay rate (with the fluorescence intensity obtained immediately after completion of excitation being taken as 100%) during the passage of time T1, T2, or T3, and the sum total is 100% with respect to each probe (DNA oligomer). As indicated in Table 3, the probe containing two dyes (Example 8) undergoes a very short quenching process (the fluorescence decay rate obtained 0.0210 ns after excitation was 81.54%) in the single-stranded state, which indicates the presence of an exciton effect. This was not observed in other cases. The fluorescence quenching of this ODN labeled with two dyes, in the single-stranded state, plays an important role in sharp and hybridization-specific change in fluorescence intensity. Furthermore, as can be seen in Table 3, the fluorescence quenching properties agreed with quadratic or cubic function properties. With respect to the double strand with two dyes indicated in Table 3 below, measurement was carried out again under the same conditions (however, measurement of T1 was omitted). As a result, the fluorescence decay rate when T2=2.05 was 44%, the fluorescence decay rate when T3=4.38 was 56%, T was 3.33 (ns), and CHISQ was 1.09. Thus values that were very close to those indicated in Table 3 below were obtained. That is, it is indicated that the probe of this example has excellent reproducibility in this fluorescence lifetime measurement.

TABLE 3

|  | One dye Single strand | One dye Double strand | Two dyes Single strand | Two dyes Double strand |
|---|---|---|---|---|
| T1 | — | — | 0.0210 ns (81.54%) | 0.551 ns (2.73%) |
| T2 | 0.934 ns (39.19%) | 1.58 ns (24.63%) | 1.28 ns (8.99%) | 2.33 ns (50.30%) |
| T3 | 3.12 ns (60.81%) | 3.60 ns (75.37%) | 3.76 ns (9.48%) | 4.57 ns (46.97%) |
| T | 2.26 | 3.10 | 0.489 | 3.33 |
| CHISQ | 1.32 | 0.96 | 1.11 | 1.04 |

2.5 μM strand
50 mM phosphoric acid buffer (pH 7.0)
100 mM NaCl
Measured at 455 nm (prompt) and 600 nm (decay).

Example 11

A DNA oligomer represented by Chemical Formula 117 below was synthesized in the same manner as in Example 8 except that a compound represented by Chemical Formula 115' below was used as a dye instead of Compound 107. Compounds with n being 3, 4, 5, and 6, were synthesized in the same manner. Furthermore, it was used as a fluorescence probe in the same manner as in Example 8, and the performance thereof was evaluated by fluorescence measurement. The result is indicated in Table 4 below. As indicated in Table 4, Compound 117 is different in absorption band from the DNA oligomer (Compound 113) of Example 8, but similarly it exhibited a good exciton effect. This indicates that in the present invention, multicolor detection can be carried out using fluorescence probes with different absorption bands from each other.

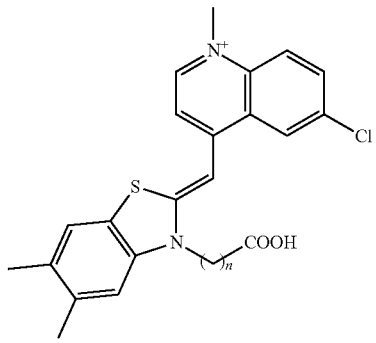

115'

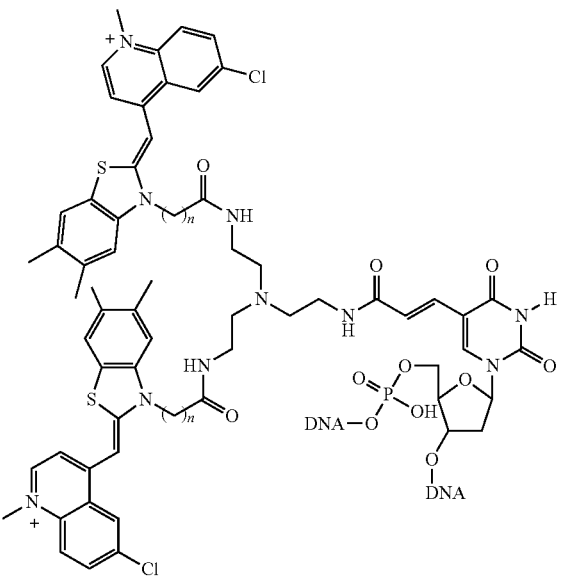

117

TABLE 4

|  |  | $\lambda_{max}$ (nm) of UV and absorption coefficient | $\lambda_{max}$ (nm) of fluorescence | Quantum yield | Ratio |
|---|---|---|---|---|---|
| n = 4 | Probe Single strand | 499(135000) 532(86000) | 553 | 0.00911 | — |
|  | Probe-DNA Double strand | 505(111000) 530(148000) | 550 | 0.0706 | 7.7 |

Example 12

A DNA oligomer (Compound 118) expressed by the sequence described below was synthesized. X is a nucleotide (represented by the formula described below, referred to as Chemical Formula 118) having the same dye structure as that of Example 9. As indicated in the sequence described below, this DNA oligomer contains two successive nucleotides sequenced, each of which contains a dye introduced therein. Introduction of the dye and synthesis of the DNA oligomer were carried out in the same manners as in the respective examples described above.

5'-d(TTTTTTXXTTTTT)-3'   (SEQ ID NO. 3)

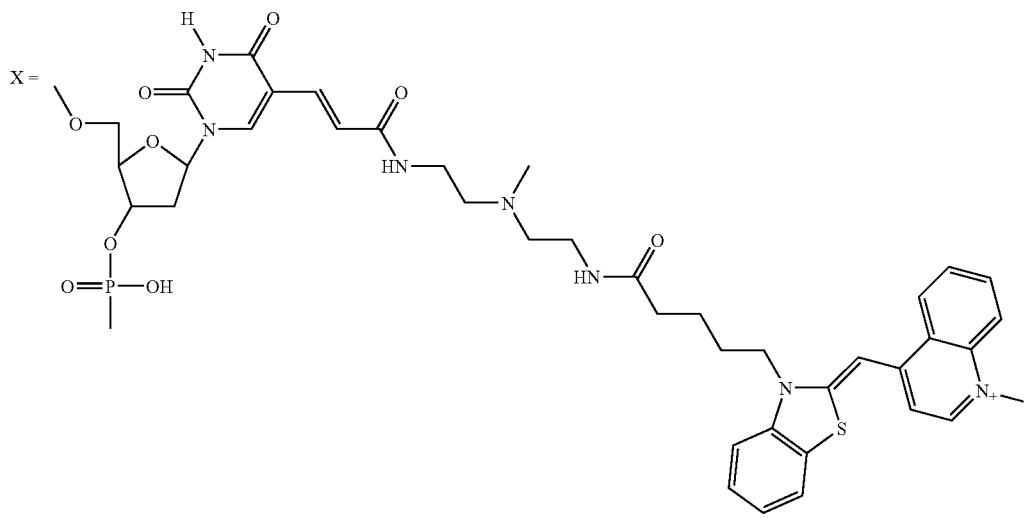

Furthermore, this DNA oligomer was used as a fluorescence probe in the same manner as in the respective examples described above, and the performance thereof was evaluated through fluorescence measurement.
2.5 μM probe (strand concentration)
50 mM phosphoric acid buffer (pH 7.0)
100 mM NaCl
2.5 μM complementary strand (strand concentration)

Figure 16:
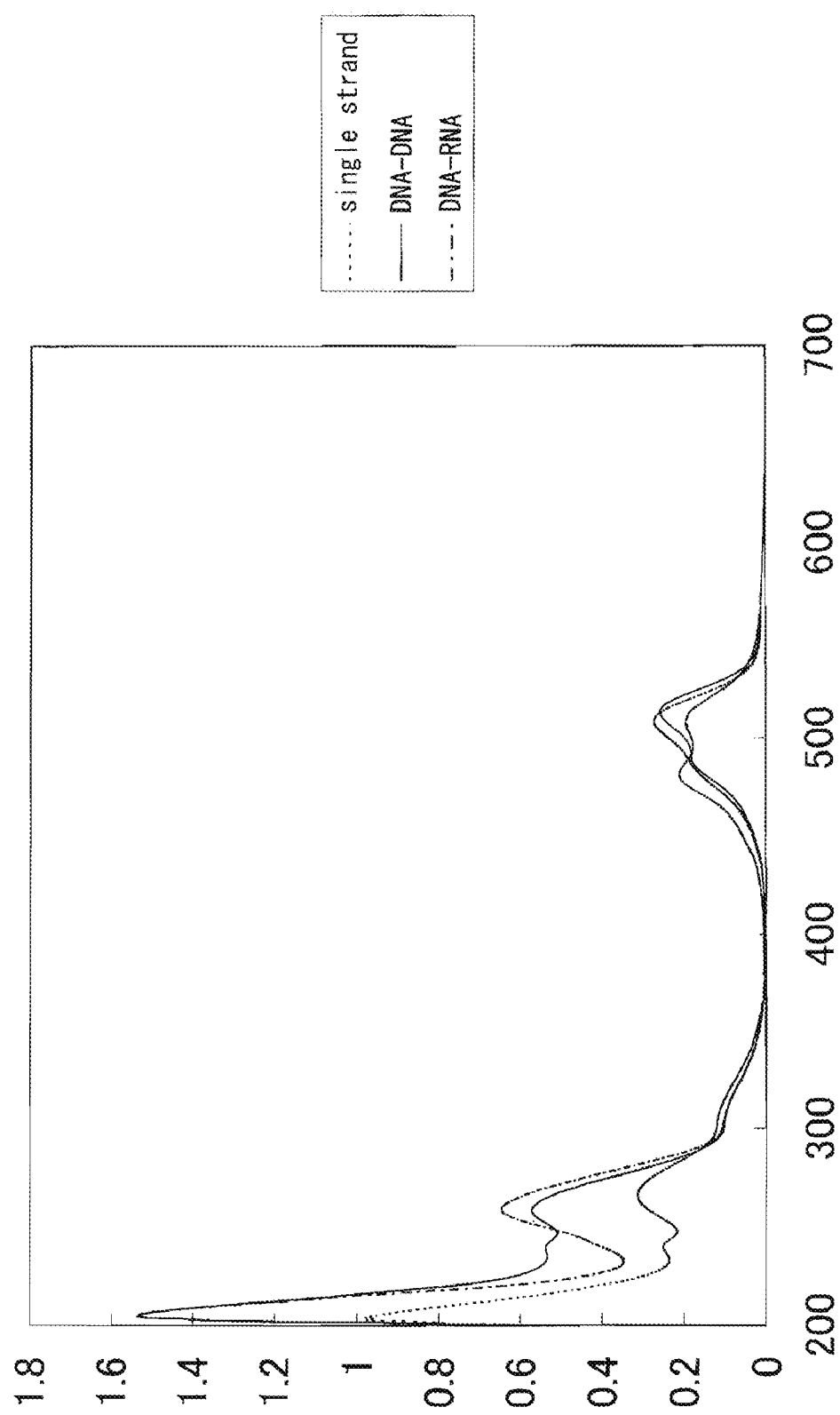
FIG. 16 shows UV spectra of three samples of a fluorescent probe according to yet another example that were in a single strand state, a DNA-DNA double helix state, and a DNA-RNA double helix state, respectively.
Figure 17:
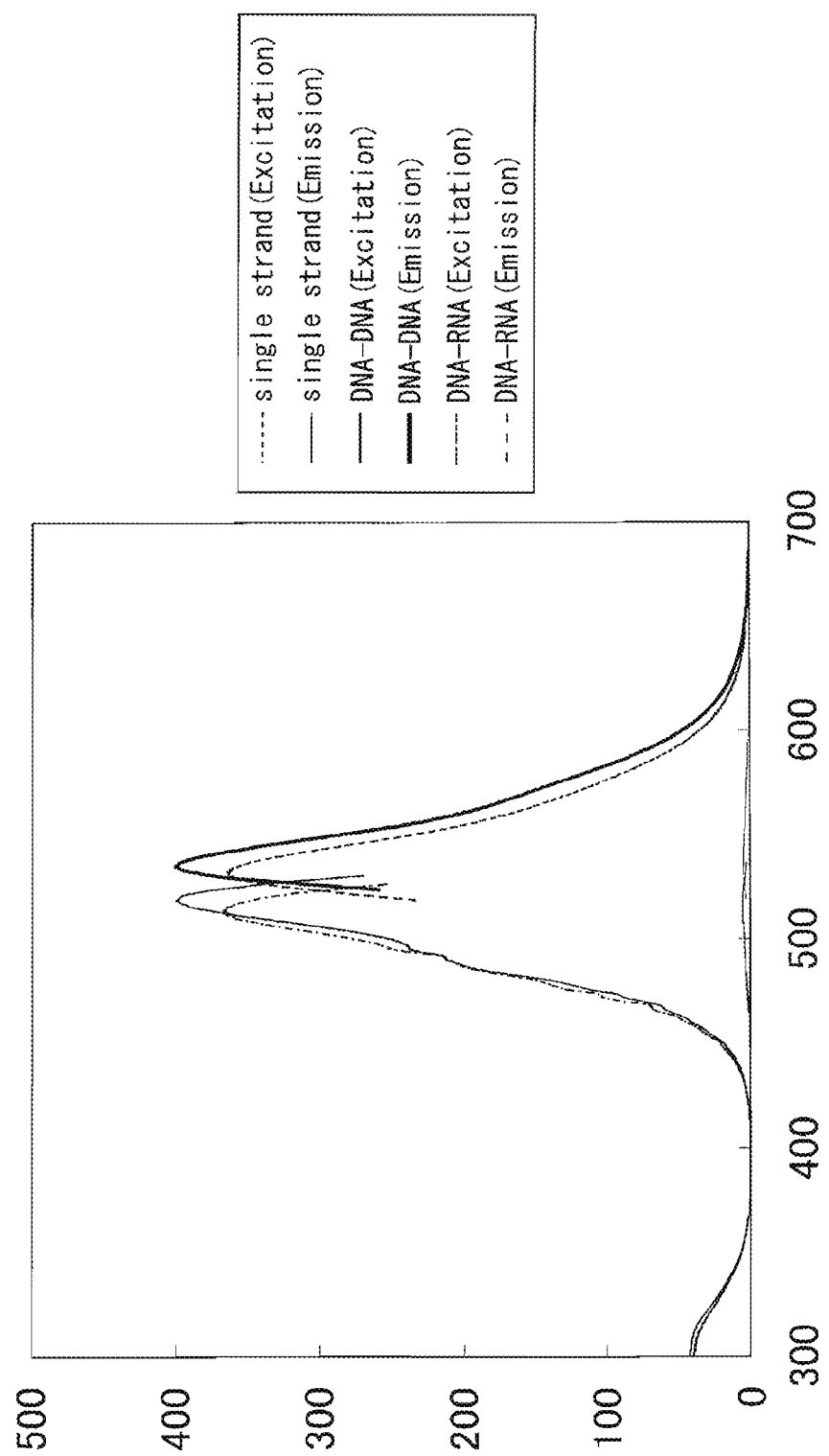
FIG. 17 shows fluorescence spectra of the three samples of the fluorescent probe shown in FIG. 16 that were in a single strand state, a DNA-DNA double helix state, and a DNA-RNA double helix state, respectively.

The results are shown in FIGS. 16 and 17. FIG. 16 is a diagram showing absorption spectra (the dotted line shows the spectrum of the single strand, the solid line shows the spectrum of the DNA-DNA strand, and the chain line shows the spectrum of the DNA-RNA strand), and FIG. 17 is a diagram showing both excitation spectra and fluorescence emission spectra. In FIG. 17, the curves located on the left side (the shorter wavelength side) indicate the excitation spectra while the curves located on the right side (the longer wavelength side) indicate the fluorescence emission spectra. In both the excitation spectra and the fluorescence emission spectra, the single strand exhibited the lowest emission intensity, the DNA-RNA strand exhibited the emission intensity higher than that of the single strand, and the DNA-DNA strand exhibited the highest emission intensity. As shown in FIGS. 16 and 17, even when two successive nucleotides, each of which contains a dye introduced therein, are sequenced, an exciton effect was exhibited because it was possible to locate the dyes at a short distance, and the states before and after hybridization with target nucleic acid can be differentiated clearly from each other by fluorescence intensity.

Example 13

Compounds (DNA oligomers) represented by Chemical Formula 113 or 114, i.e. the respective ODNs indicated in Table 5 below, were synthesized with the linker length n and nucleic acid sequence being changed variously. The "ODN" denotes oligodeoxyribonucleotide (DNA oligomer) as described above. The synthesis was carried out in the same manner as in Examples 1 to 4, 6, 8, 9, and 12 except that in each of the compounds prepared the carbon number (chain length) of 5-bromovaleric acid (5-bromopentanoic acid) used as a raw material was changed according to the linker length, and the sequence was changed suitably in the synthesis of oligodeoxyribonucleotide. ODN1 is identical to oligodeoxyribonucleotide (DNA oligomer) synthesized in Example 8, and ODN4 and ODN5 are identical to oligodeoxyribonucleotide (DNA oligomer) synthesized in Example 9. In the synthesis, N-hydroxysuccinimidyl ester (Compound 109) of thiazole orange used herein was at least 50 equivalents of active amino group. After the synthesis, the development time in reversed-phase HPLC was 20 to 30 minutes or longer as required. In Table 5 indicated below, for example, $[113]_{(n)}$ or $[114]_{(n)}$ denotes that a nucleotide represented by Chemical Formula 113 or 114 has been inserted in that site, and n denotes a linker length. In Table 5, ODN1' indicates a DNA strand complementary to ODN1. Similarly, ODN2' denotes a DNA strand complementary to ODN2, and ODN3' indicates a DNA strand complementary to ODN3.

TABLE 5

| | Sequence (5'→3') | |
|---|---|---|
| ODN1 | CGCAAT$[113]_{(n)}$TAACGC | SEQ ID NO. 1 |
| ODN1' | GCGTTAAATTGCG | SEQ ID NO. 2 |
| ODN2 | TTTTTT$[113]_{(4)}$TTTTTT | SEQ ID NO. 4 |
| ODN2' | AAAAAAAAAAAA | SEQ ID NO. 5 |
| ODN3 | TGAAGGGCTT$[113]_{(4)}$TGAACTCTG | SEQ ID NO. 6 |
| ODN3' | CAGAGTTCAAAAGCCCTTCA | SEQ ID NO. 7 |
| ODN4 | CGCAAT$[114]_{(4)}$TAACGC | SEQ ID NO. 1 |
| ODN5 | CGCAAT$[114]_{(4)}[114]_{(4)}$AACGC | SEQ ID NO. 8 |

TABLE 5-continued

| Sequence (5'→3') | | |
|---|---|---|
| ODN(anti4.5S) | GCCTCCT[113]$_{(4)}$CAGCAAATCC[113]$_{(4)}$ACCGGCGTG | SEQ ID NO. 9 |
| ODN(antiB1) | CCTCCCAAG[113]$_{(4)}$GCTGGGAT[113]$_{(4)}$AAAGGCGTG | SEQ ID NO. 10 |

With respect to each ODN synthesized as described above, the concentration was determined through enzymatic digestion in the same manner as in Example 4. Furthermore, each ODN synthesized as described above was identified with a MALDI TOF mass spectrum. The mass spectrometry values are indicated below.

ODN1 (n=3), CGCAAT[113]$_{(3)}$TAACGC, calcd for $C_{178}H_{213}N_{56}O_{78}P_{12}S_2$ ([M.H]$^+$) 4820.7, found 4818.9;
ODN1 (n=4), CGCAAT[113]$_{(4)}$TAACGC, calcd for $C_{180}H_{217}N_{56}O_{78}P_{12}S_2$ ([M.H]$^+$) 4848.8, found 4751.4;
ODN1 (n=5), CGCAAT[113]$_{(5)}$TAACGC, calcd for $C_{182}H_{221}N_{56}O_{78}P_{12}S_2$ ([M.H]$^+$) 4876.8, found 4875.6;
ODN1 (n=6), CGCAAT[113]$_{(6)}$ TAACGC, calcd for $C_{184}H_{225}N_{56}O_{78}P_{12}S_2$ (([M.H]$^+$) 4904.9, found 4903.6;
ODN2, TTTTTT[113]$_{(4)}$TTTTTT, calcd for $C_{184}H_{227}N_{34}O_{92}P_{12}S_2$ ([M.H]$^+$) 4822.8, found 4821.4;
ODN3, TGAAGGGCTT[113]$_{(4)}$TGAACTCTG, calcd for $C_{251}H_{305}N_{81}O_{124}P_{19}S_2$ ([M.H]$^+$) 7093.2, found 7092.3;
ODN (anti4.5S), GCCTCCT[113]$_{(4)}$CAGCAAATCC [113]$_{(4)}$ACCGGCGTG, calcd for $C_{377}H_{456}N_{116}O_{173}P_{27}S_4$ ([M.3H]$^+$) 10344.9, found 10342.7;
ODN (antiB1), CCTCCCAAG[113]$_{(4)}$GCTGGGAT[113]$_{(4)}$AAAGGCGTG, calcd for $C_{381}H_{456}N_{124}O_{172}P_{27}S_4$ ([M.3H]$^+$) 10489.0, found 10489.8.

Among ODNs indicated in Table 5, with respect to each of ODNs (ODN1, ODN2, and ODN3) containing [113](n) that were obtained with the sequence and linker length being changed variously, the absorption spectrum, excitation spectrum, and emission spectrum were measured before and after hybridization with a complementary strand. The results are indicated together in Table 6 below as well as FIGS. 18 and 19.

TABLE 6

| | $\lambda_{max}$/ nm($\epsilon$) | $\lambda_{em}$/ nm[b] | $\Phi_f^c$ | $I_{ds}$/ $I_{ss}^d$ | Tm/ °C. |
|---|---|---|---|---|---|
| ODN1 (n = 3) | 480(117000) 510(93800) | 537 | 0.096 | — | — |
| ODN1 (n = 3)/ODN1' | 505(145000) | 529 | 0.298 | 7.6 | 66 |
| ODN1 (n = 4) | 479(156000) 509(104000) | 538 | 0.059 | — | — |
| ODN1 (n = 4)/ODN1' | 509(179000) | 528 | 0.272 | 14.4 | 65 |
| ODN1 (n = 5) | 480(139000) 510(107000) | 538 | 0.043 | — | — |
| ODN1 (n = 5)/ODN1' | 508(172000) | 529 | 0.208 | 8.1 | 67 |
| ODN1 (n = 6) | 479(139000) 509(93300) | 536 | 0.053 | — | — |
| ODN1 (n = 6)/ODN1' | 509(164000) | 528 | 0.265 | 10.9 | 65 |
| 5'-CGCAATTTAACGC-3'/ODN1' | — | — | — | — | 58 |
| ODN2 | 478(221000) 505(115000) | 545 | 0.010 | — | — |
| ODN2/ODN2' | 513(209000) | 536 | 0.469 | 160 | 62 |
| ODN3 | 482(146000) 510(145000) | 535 | 0.074 | — | — |
| ODN3/ODN3' | 509(191000) | 530 | 0.232 | 4.5 | 74 |

Measurement conditions: 2.5 µM DNA, 50 mM sodium phosphate buffer solution (pH = 7.0), 100 mM sodium chloride
[b]Excitation at 488 nm
[c]Excitation at $\lambda_{max}$ (excitation at $\lambda_{max}$ on the longer wavelength side when there are two $\lambda_{max}$)
[d]Fluorescence intensity ratio at $\lambda_{em}$ between a double-stranded state and a single-stranded state In Table 6, ODN1 (n=3 to 6) has the same structure as that of oligodeoxyribonucleotide (5'-d(CGCAATXTAACGC)-3', where X was the site where a dye 113 had been introduced) of Example 8. In Example 8, the fluorescence quantum yield $\Phi_F$ and the fluorescence intensity ratio ($I_{ds}/I_{ss}$) between the double-stranded state and a single-stranded state were measured through excitation carried out at a wavelength of 488 nm. However, in this example (Example 13), as described above, they were measured through excitation carried out at $\lambda_{max}$ in the UV absorption spectrum. Therefore Table 1 (Example 8) and Table 6 (Example 13) indicate the same substance with different fluorescence quantum yield OF and fluorescence intensity ratio ($I_{ds}/I_{ss}$).

Figure 18:
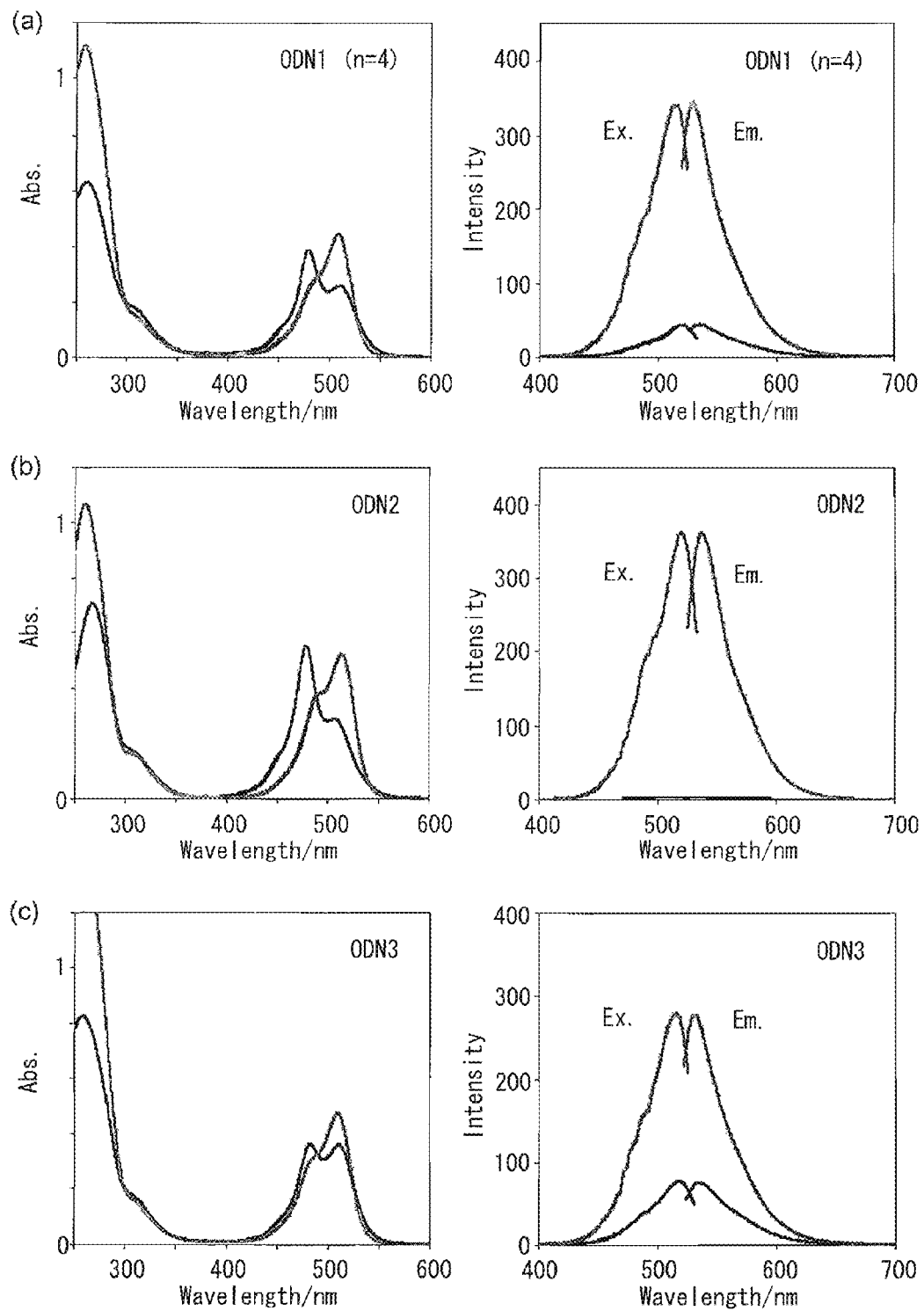
FIG. 18 shows graphs illustrating absorption spectra, excitation spectra, and emission spectra of several types of fluorescent probe according to an example.

FIG. 18 shows graphs, each of which illustrates the absorption spectrum, excitation spectrum, and emission spectrum of [113]$_{(4)}$-containing ODN. In each of FIGS. 18(a), (b), and (c), the graph shown on the left side illustrates the absorption spectrum, with the horizontal axis indicating the wavelength and the vertical axis indicating the absorbance. The graph shown on the right side illustrates the excitation spectrum and the emission spectrum, with the horizontal axis indicating the wavelength and the vertical axis indicating the emission intensity. Each measurement was carried out at 25° C. using, as a sample, [113]$_{(4)}$-containing ODN in a 50 mM sodium phosphate buffer solution (pH=7.0) containing 100 mM sodium chloride. In each graph shown in FIG. 18, the black line indicates the measurement result with respect to the single-stranded ODN (ss), and the gray line indicates the measurement result with respect to ODN (ds) hybridized with a corresponding complementary strand DNA.

FIG. 18(a) shows the measurement result with respect to ODN1 (n=4) (2.5 µM). With respect to the excitation spectrum, the emission intensity at a wavelength of 534 nm was measured with respect to the ss, and the emission intensity at a wavelength of 528 nm was measured with respect to the ds. The emission spectra were measured, with the ss being excited at a wavelength of 519 nm and the ds being excited at a wavelength of 514 nm.

FIG. 18(b) shows the measurement result with respect to ODN2. The strand concentration was 2.5 µM in the graph shown on the left side, and it was 1 µM in the graph shown on the right side. With respect to the excitation spectrum, the emission intensity at a wavelength of 534 nm was measured with respect to the ss, and the emission intensity at a wavelength of 537 nm was measured with respect to the ds. The emission spectra were measured, with the ss being excited at a wavelength of 517 nm and the ds being excited at a wavelength of 519 nm.

FIG. 18(c) shows the measurement result with respect to ODN3. The strand concentration was 2.5 µM. With respect to the excitation spectrum, the emission intensity at a wavelength of 535 nm was measured with respect to the ss, and the emission intensity at a wavelength of 530 nm was measured with respect to the ds. The emission spectra were measured with the ss being excited at a wavelength of 518 nm and the ds being excited at a wavelength of 516 nm.

Figure 19:
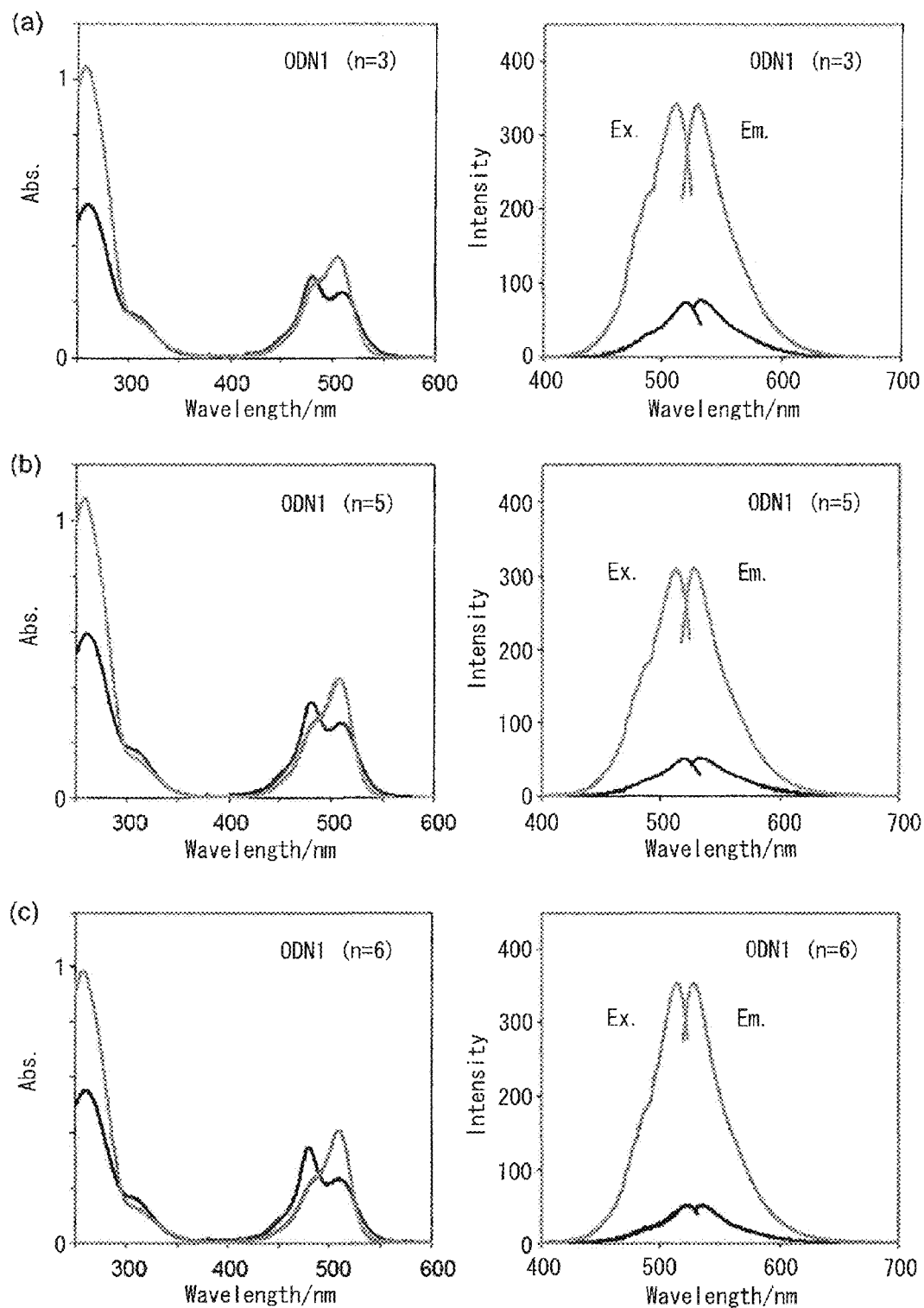
FIG. 19 shows graphs illustrating absorption spectra, excitation spectra, and emission spectra of other fluorescent probe according to an example.

FIG. 19 shows graphs, each of which illustrates the absorption spectrum, excitation spectrum, and emission spectrum of ODN1 (n=3, 5, and 6). In each of FIGS. 19(a), (b), and (c), the graph shown on the left side illustrates the absorption spectrum, with the horizontal axis indicating the wavelength and the vertical axis indicating the absorbance. The graph shown on the right side illustrates the excitation spectrum and the emission spectrum, with the horizontal axis indicating the wavelength and the vertical axis indicating the emission intensity. Each measurement was carried out at 25° C. using, as a sample, ODN1 (n=3, 5, or 6) in a 50 mM sodium phosphate buffer solution (pH=7.0) containing 100 mM sodium chloride. In each graph shown in FIG. 19, the black line indicates the measurement result with respect to the single-stranded ODN (ss), and the gray line indicates the measurement result with respect to ODN (ds) hybridized with a corresponding complementary strand DNA.

FIG. 19(a) shows the measurement result with respect to ODN1 (n=3) (2.5 µM). With respect to the excitation spectrum, the emission intensity at a wavelength of 537 nm was measured with respect to the ss, and the emission intensity at a wavelength of 529 nm was measured with respect to the ds. The emission spectra were measured, with the ss being excited at a wavelength of 521 nm and the ds being excited at a wavelength of 511 nm.

FIG. 19(b) shows the measurement result with respect to ODN1 (n=5) (2.5 µM). With respect to the excitation spectrum, the emission intensity at a wavelength of 538 nm was measured with respect to the ss, and the emission intensity at a wavelength of 529 nm was measured with respect to the ds. The emission spectra were measured, with the ss being excited at a wavelength of 520 nm and the ds being excited at a wavelength of 512 nm.

FIG. 19(c) shows the measurement result with respect to ODN1 (n=6). The strand concentration was 2.5 µM. With respect to the excitation spectrum, the emission intensity at a wavelength of 536 nm was measured with respect to the ss, and the emission intensity at a wavelength of 528 nm was measured with respect to the ds. The emission spectra were measured with the ss being excited at a wavelength of 523 nm and the ds being excited at a wavelength of 514 nm.

As shown in Table 6 as well as FIGS. 18 and 19, two absorption bands were observed in the range of 400 to 550 nm with respect to the respective $[113]_{(n)}$-containing ODN samples. The absorption band on the shorter wavelength side (up to 480 nm) was increased when the 1(n)-containing ODN sample was in the single-stranded state, while the absorption band on the longer wavelength side (up to 510 nm) appeared prominently (dominantly) when the 1(n)-containing ODN sample hybridized with a complementary strand. The absorption band on the longer wavelength side (up to 510 nm) is a typical absorption band of thiazole orange alone. In the emission spectrum, a single broad absorption band was observed up to 530 nm. With the hybridization of a $[113]_{(n)}$-containing ODN sample with a complementary strand, the emission intensity was changed clearly. That is, the $[113]_{(n)}$-containing ODN sample hybridized to a target DNA strand exhibited strong fluorescence, but the $[113]_{(n)}$-containing ODN sample before being hybridized exhibited only very weak fluorescence as compared to that exhibited after hybridization. Particularly, the fluorescence of ODN2 formed of a polypyrimidine sequence was quenched almost completely in the single-stranded state. The fluorescence intensity ratio ($I_{ds}/I_{ss}$) between the double-stranded state and the single-stranded state of ODN2 reached 160 at the maximum emission wavelength. When ODN3' as a 20-mer ODN chain and ODN3 having a common sequence were hybridized with each other, the emission intensity was clearly different before and after hybridization. Furthermore, as can be seen from Table 6 as well as FIG. 18(a) and FIG. 19, when the linker length n was changed from 3 to 6 in ODN1 of this example, a large $I_{ds}/I_{ss}$ value was obtained with any linker length. As described above, all the ODNs indicated in Table 6 exhibited high quenching ability although there was a difference in quenching ability depending on the linker length and the sequence of the probe.

As indicated in Table 6 above, the melting point ($T_m$) of ODN1 (n=4)/ODN1' increased by 7 to 9° C. as compared to the native double strand, 5'-CGCAATTTAACGC-3'/ODN1'. This increase in $T_m$ value implies that two cationic dyes contained in the probe were bonded effectively to a double strand formed together with the target sequence. Furthermore, as can be seen from FIGS. 18 and 19, the excitation spectrum indicated a single broad peak around 510 nm regardless of the structure of the compound. This wavelength agreed well with one wavelength in the absorption band. That is, conceivably, the absorption associated with fluorescence emission occurs only in the absorption band around 510 nm, and the absorption band around 480 nm hardly affects the emission. Furthermore, the exciton coupling energy was estimated to be 1230 cm$^{-1}$ based on the absorption band shift from 510 nm to around 480 nm that was caused by dye aggregation. This is equivalent to the coupling energy that has been reported for the H-aggregate of cyanine dyes. However, these theoretical considerations do not limit the present invention.

[Absorption Spectrum]

Figure 20:
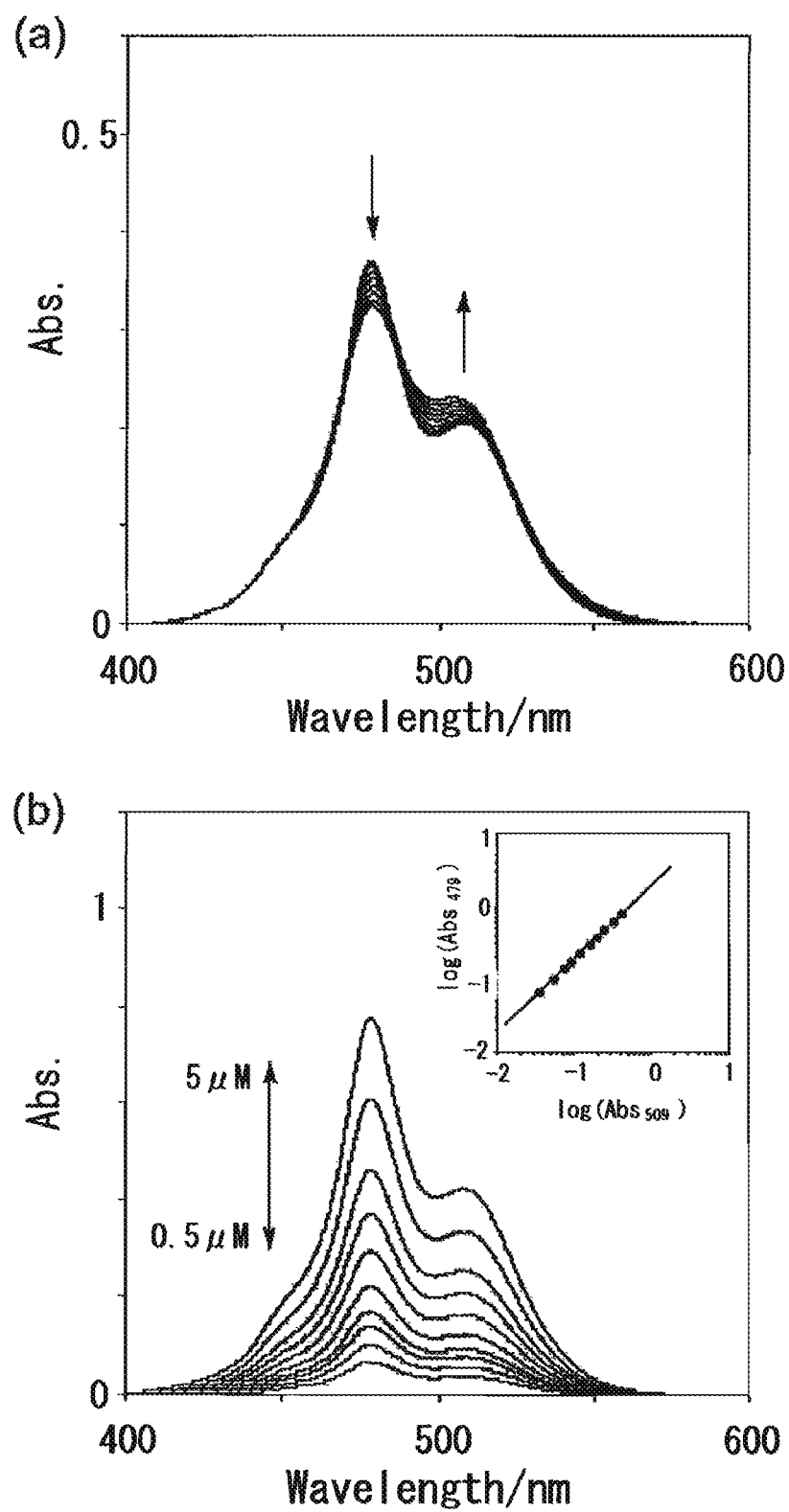
FIG. 20 shows diagrams illustrating absorption spectra obtained by measuring the absorption spectra of a fluorescent probe according to an example at various temperatures and concentrations.

The absorption spectra of the ODN1 (n=4) were determined at various temperatures and concentrations, and the effects of the temperature and concentration on the absorption band were checked. The results are shown in the absorption spectrum diatram in FIG. 20. In FIGS. 20(a) and 20(b), the horizontal axis indicates the wavelength, and the vertical axis indicates the absorbance. Each measurement was carried out using, as a sample, ODN1 (n=4) contained in 50 mM sodium phosphate buffer solution (pH=7.0) containing 100 mM sodium chloride.

FIG. 20(a) shows a change in absorption spectrum obtained when the solution temperature was changed. The ODN concentration was 2.5 µM. The spectrum was measured at 10° C. intervals from 10° C. to 90° C.

FIG. 20(b) shows a change in absorption spectrum obtained when the solution concentration was changed. The measurement temperature was 25° C. The ODN concentrations were 0.5, 0.75, 1.0, 1.2, 1.5, 2.0, 2.5, 3.0, 4.0, and 5.0 µM.

The inset is a graph showing the relationship between the logarithm of the absorbance at a wavelength of 479 nm (vertical axis) and the logarithm of the absorbance at a wavelength of 509 nm (horizontal axis).

As shown in FIG. 20(a), the absorbance ratio between the two absorption bands was changed slightly when the measurement was carried out with the sample temperature being changed. That is, with the increase in sample temperature, absorbance in the absorption band of 479 nm decreased gradually, and absorbance in the absorption band of 509 nm increased. However, as can be seen from FIG. 20(a), the change was very small. This indicates that in the probe of the present invention, ODN1 (n=4), the structure change caused according to the temperature change is very small, and therefore it can be used while hardly being affected by temperature. As shown in FIG. 20(a), an isosbestic point that indicated the presence of two spectrum components was observed at 487 nm.

On the other hand, as shown in FIG. 20(b), when the concentration of the sample, ODN1(n=4), was increased, an increase in absorbance was observed in both the absorption bands. Furthermore, as shown in the inset, the plot of log (Abs$_{479}$) versus log(Abs$_{509}$), i.e. the ratio between logarithms of the absorbances in the respective absorption bands, showed a straight line. This indicates that the ratio between the two spectrum components was almost constant regardless of the ODN concentration. In other words, the probe of the present invention, ODN1 (n=4), can be used without being affected by the concentration thereof, since the structure thereof hardly is changed even when its concentration in the solution is changed.

The cause of the spectrum changes shown in FIGS. 20(a) and (b) can be described, for example, as follows. However, these descriptions are examples of theoretical considerations and do not limit the present invention. That is, first, ODN1 (n=4) forms an intramolecular H-aggregate according to the dichroic system. Presumably, the spectrum change shown in FIG. 20(a) was caused because the structure of the H-aggregate had been loosened slightly due to increase in temperature. Conceivably, since the intramolecular H-aggregate is completed intramolecularly, the structure hardly is changed by, for example, an intermolecular interaction even when the concentration increases, and therefore the ratio between the two spectrum components is almost constant as shown in FIG. 20(b) and the inset. Conceivably, two conformation modes of an intramolecular H-aggregate and dye monomers (the dye portions have not been aggregated) exist in the sample solution of ODN1 (n=4). It is surmised that the absorption band located on the shorter wavelength side (479 nm) is derived from the intramolecular H-aggregate. On the other hand, it is surmised that the absorption band (509 nm) located on the longer wavelength side is derived from the dye monomers since it increased by heating.

[CD Spectrum]

Figure 21:
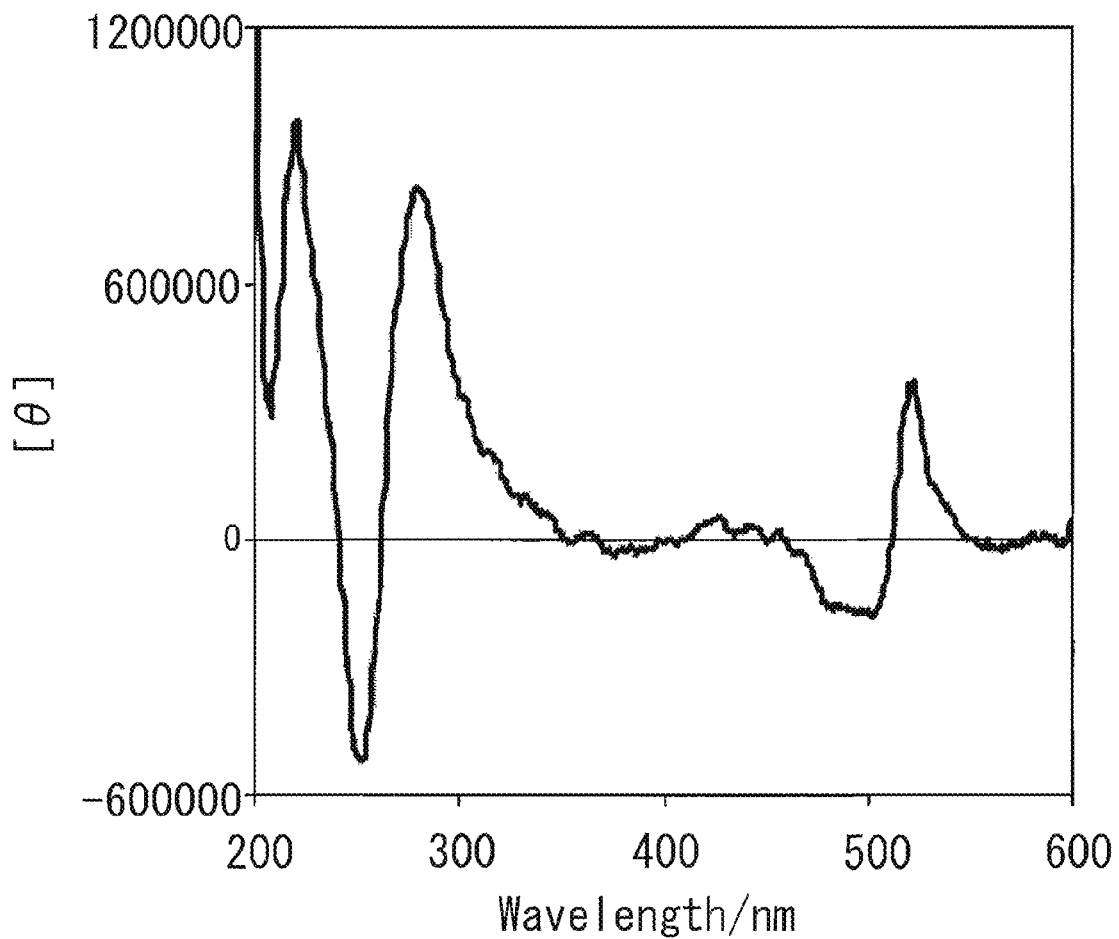
FIG. 21 is a CD spectrum diagram of a double strand obtained through hybridization of a fluorescent probe of an example.

The CD spectrum of ODN1 (n=4)/ODN1' was measured. The measurement was carried out at 25° C. in a 50 mM sodium phosphate buffer solution (pH=7.0) containing 100 mM sodium chloride, with the strand concentration being 2.5 µM. The measurement result is shown in the CD spectrum diagram in FIG. 21. In FIG. 21, the horizontal axis indicates the wavelength (nm), and the vertical axis indicates the angle θ. As shown in FIG. 21, the ODN1 (n=4)/ODN1' double strand exhibited a split-Cotton effect between 450 and 550 nm. That is, a measured CD pair showed a typical pattern observed when a thiazole orange dye intercalated into a DNA double strand. Conceivably, in other words, the dye portions of the ODN1 (n=4) intercalated into a double-stranded DNA that had been formed, and thereby a dichroic aggregate (H-aggregate) was prevented strongly from being formed. This CD measurement result implies, together with the $T_m$ measurement result, that when the dye portions of the ODN1 (n=4) bind to the double-stranded DNA, both the two dye portions intercalate into the major groove and thereby a thermally stable double stranded structure is formed. However, this theoretical consideration does not limit the present invention. The fact that the double-stranded structure to be formed is thermally stable indicates that the probe (nucleic acid) of the present invention can be used effectively for detecting the complementary sequence.

Example 14

With respect to the ODN5 (CGCAAT[114]$_{(4)}$[114]$_{(4)}$ AACGC), the absorption spectrum, excitation spectrum, and emission spectrum were measured in the double-stranded state and the single-stranded state. The results are shown in Table 7 below and FIG. 22.

TABLE 7

| | $\lambda_{max}/$ nm(ε) | $\lambda_{em}/$ nm$^b$ | $\Phi_f^c$ | $I_{ds}/I_{ss}^d$ | Tm/ ° C. |
|---|---|---|---|---|---|
| ODN5 | 483(123000) 511(118000) | 545 | 0.059 | — | — |
| ODN5/ODN1' | 509(180000) | 528 | 0.275 | 10.3 | 71 |

Figure 22:
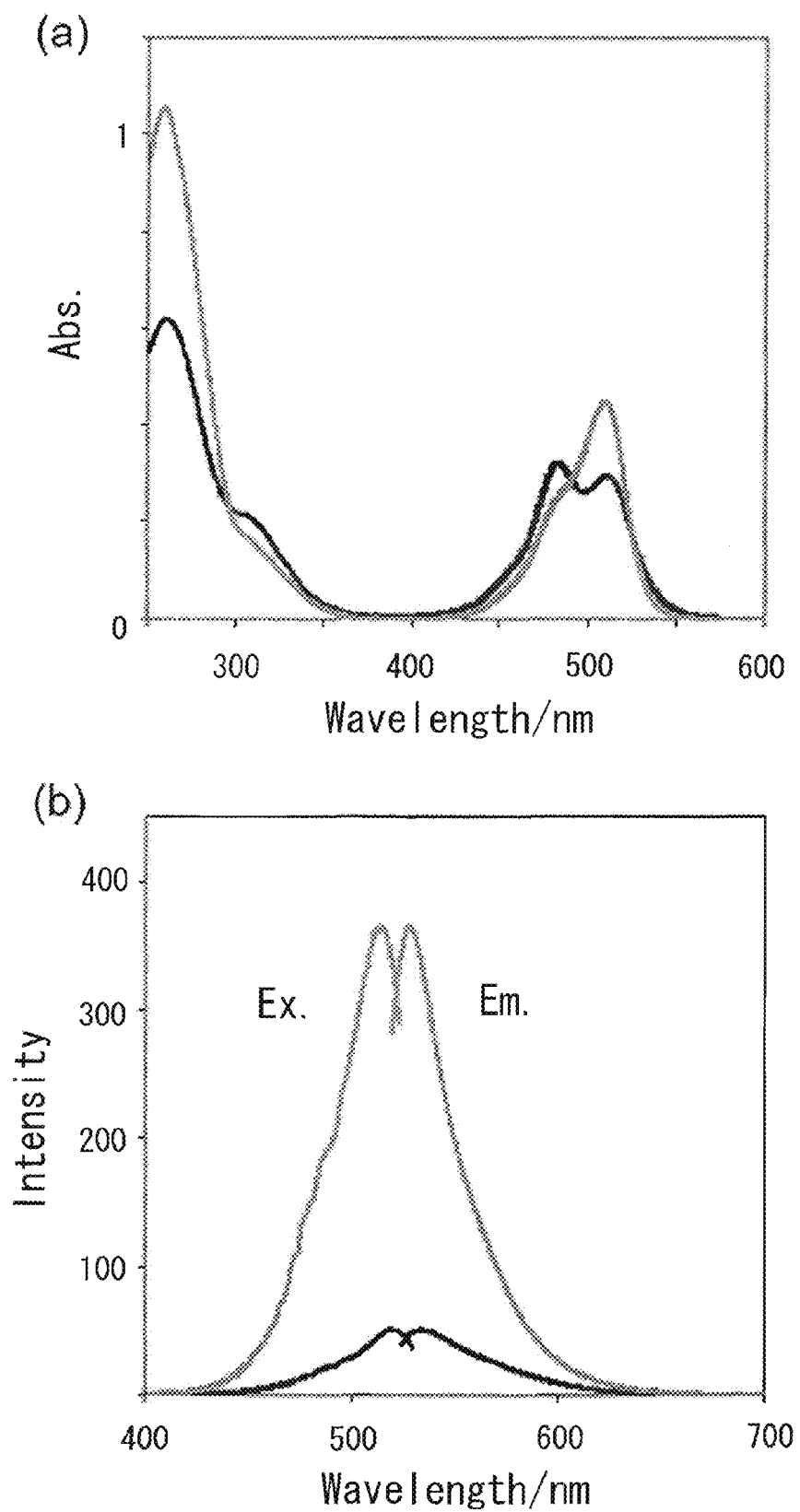
FIG. 22 shows graphs illustrating absorption spectra, excitation spectra, and emission spectra of another fluorescent probe according to an example.

Measurement conditions: 2.5 µM DNA, 50 mM sodium phosphate buffer solution (pH = 7.0), 100 mM sodium chloride
$^b$Excitation at 488 nm
$^c$Excitation at $\lambda_{max}$ (excitation at $\lambda_{max}$ on the longer wavelength side when there are two $\lambda_{max}$)
$^d$Fluorescence intensity ratio at $\lambda_{em}$ between the double-stranded state and the single-stranded state FIG. 22 shows graphs illustrating the absorption spectrum, excitation spectrum, and emission spectrum of ODN5, specifically, [114]$_{(4)}$-containing ODN. The measurement was carried out at 25° C. in a 50 mM sodium phosphate buffer solution (pH=7.0) containing 100 mM sodium chloride, with the strand concentration of ODN5 being 2.5 µM. The black line indicates the measurement result with respect to the single-stranded ODN5 (ss), and the gray line indicates the measurement result with respect to the double-stranded ODN5 (ds) hybridized with ODN1'. FIG. 22(a) shows the absorption spectrum, with the horizontal axis indicating the wavelength and the vertical axis indicating the absorbance. FIG. 22(b) shows the excitation spectrum (the curve located on the shorter wavelength side) and emission spectrum (the curve located on the longer wavelength side), with the horizontal axis indicating the wavelength and the vertical axis indicating the emission intensity. With respect to the excitation spectrum, the emission intensity at a wavelength of 534 nm was measured with respect to the ss, and the emission intensity at a wavelength of 514 nm was measured with respect to the ds. The emission spectra were measured, with the ss being excited at a wavelength of 528 nm and the ds being excited at a wavelength of 519 nm.

As shown in Table 7 and FIG. 22, the ODN 5 having a sequence containing two successive [114]$_{(4)}$ nucleotides exhibited further effective fluorescence quenching as compared to the emission suppression (Table 2 in Example 9) of the single-stranded ODN4 containing only one [114]$_{(4)}$ nucleotide. With respect to the absorption spectrum of ODN5, the absorption band was shifted to the shorter wavelength side in the single-stranded state. This implies that two [114]$_{(4)}$ nucleotides contained in the ODN5 formed an intramolecular H-aggregate. This aggregation resulted in quenching of the single-stranded ODN5 as is observed in the [113]$_{(n)}$-containing ODN. That is, conceivably, the cause of the fluorescence emission suppression (quenching) is that the dye portions of the two [114]$_{(4)}$ nucleotides contained in the ODN5 formed an H-aggregate and thereby an exciton coupling occurred between the dyes. This confirmed that the ODN5 containing two [114]$_{(4)}$ nucleotides was useful for detecting the complementary strand as in the case of the [113]$_{(n)}$-containing ODN.

Example 15

Figure 23:
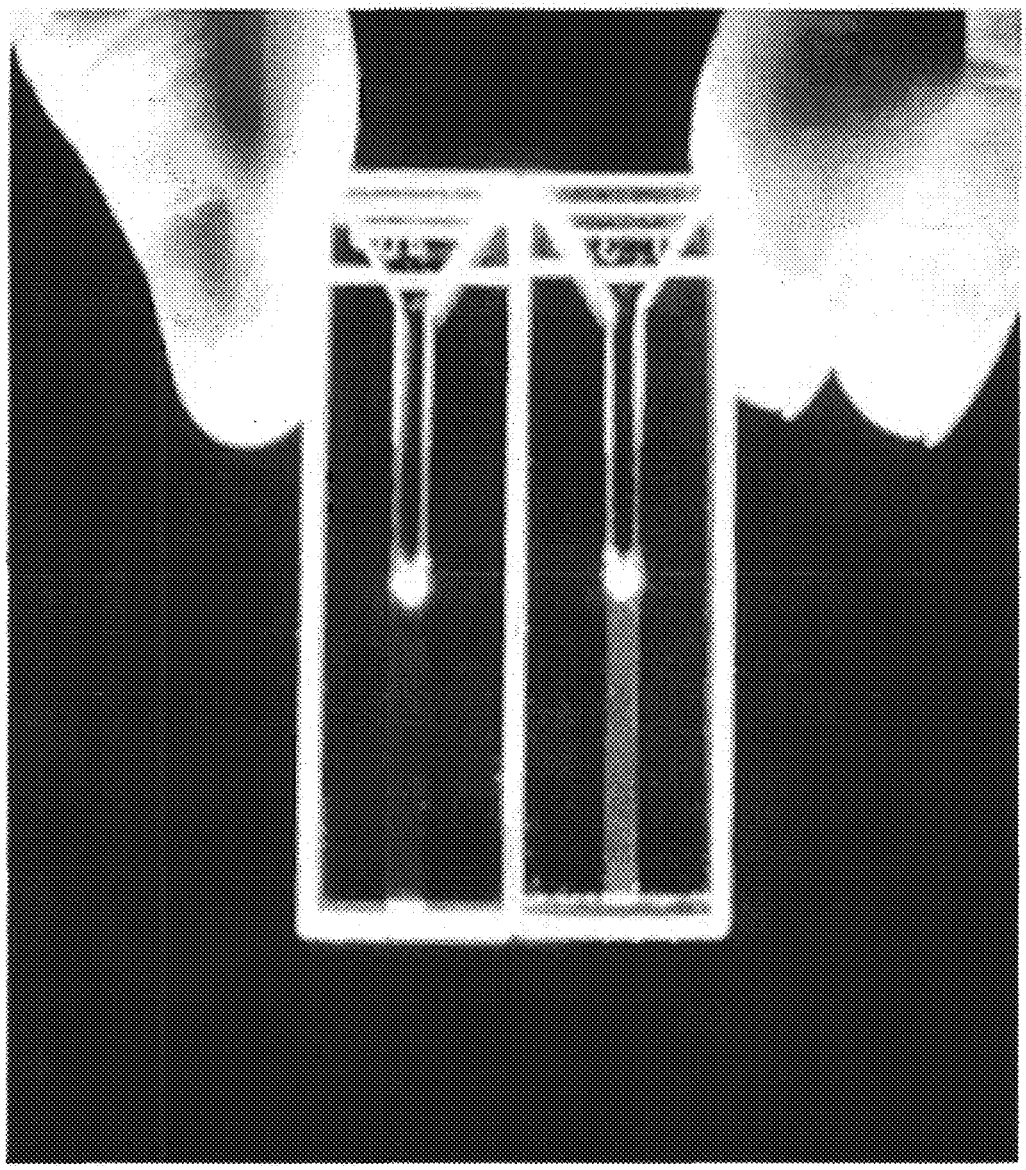
FIG. 23 is a diagram showing fluorescence emission of a double strand obtained through hybridization of another fluorescent probe of an example.

The fluorescence obtained when ODN1 (n=4) was hybridized with a complementary ODN1' was determined by the naked eye. The measurement result is shown in FIG. 23. In FIG. 23, the left cell is a cell containing an ODN1 (n=4) single strand, and the right cell is a cell containing an ODN1 (n=4)/ODN1' double strand. The respective cells show the states thereof obtained after irradiation with a 150 W halogen lamp. Each cell has a strand concentration of 2.5 µM and contains a 50 mM phosphoric acid buffer (sodium phosphate buffer solution) (pH 7.0) and 100 mM NaCl. As shown in FIG. 23, the left cell containing the ODN1 (n=4) single strand hardly emitted fluorescence after irradiation with the 150 W halogen lamp, but the right cell containing the ODN1 (n=4)/ODN1' double strand emitted light green fluorescence very clearly. Furthermore, the same result was obtained even when the complementary DNA strand ODN1' was replaced with a corresponding complementary RNA strand. Moreover, the same result was obtained in the cases of ODN2 and ODN2'. Furthermore, in the cases of ODN2 and ODN2', the same result was obtained even when ODN2' was replaced with a corresponding complementary RNA (A13-mer). In those cases, the strand concentration was 5 µM. In addition, the same results were obtained with respect to all ODNs indicated in Table 6 above. Thus, since the ODN of this example allows the fluorescence intensity to be changed clearly depending on hybridization, it was easy to determine the hybridizable target sequence by the naked eye. This indicates that those ODNs are useful for visible gene analysis.

Example 16

A DNA oligomer represented by Chemical Formula 120 below was synthesized in the same manner as in Example 8 except that a compound represented by Chemical Formula 119 below was used, as a dye, instead of compound 107.

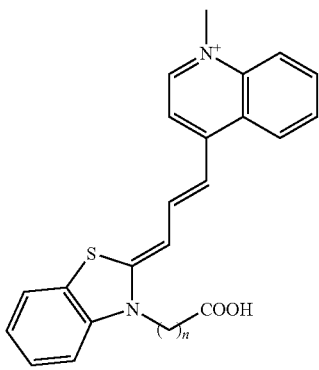

119

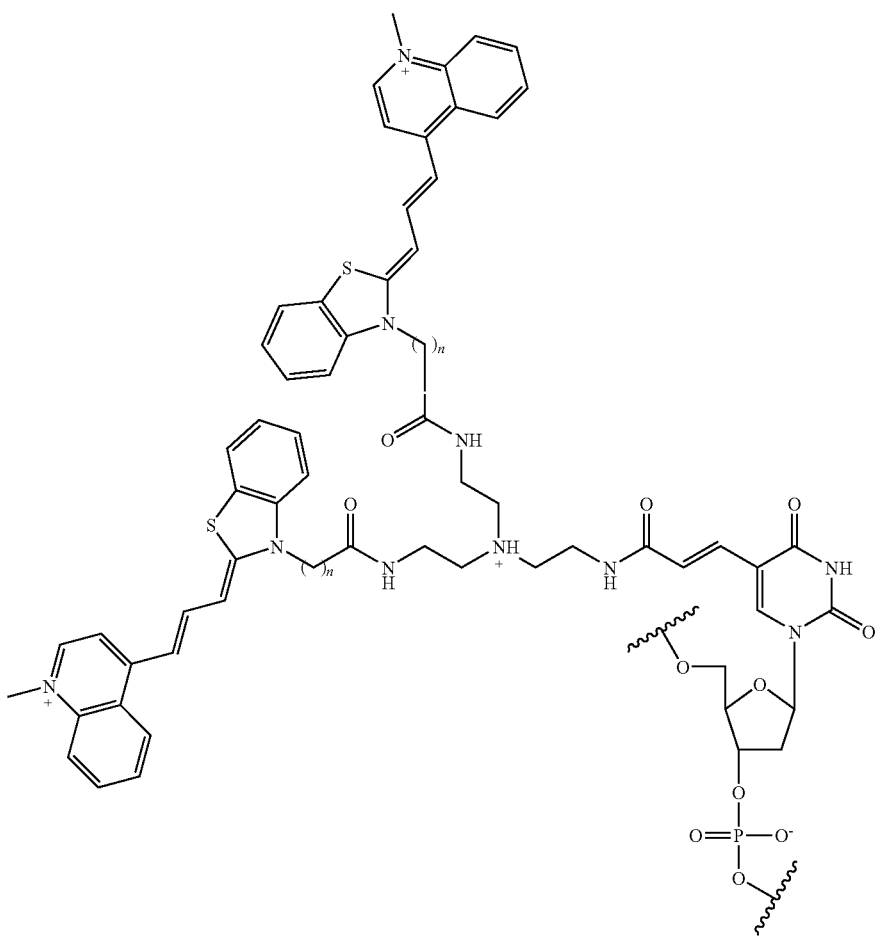

120

Figure 24:
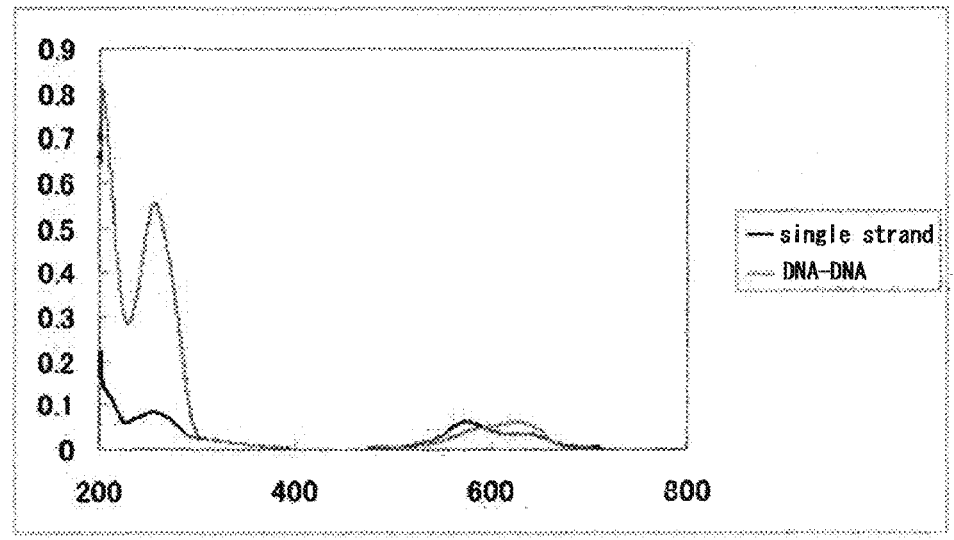
FIG. 24 shows graphs illustrating absorption spectra and emission spectra of another fluorescent probe according to an example.
Figure 24:
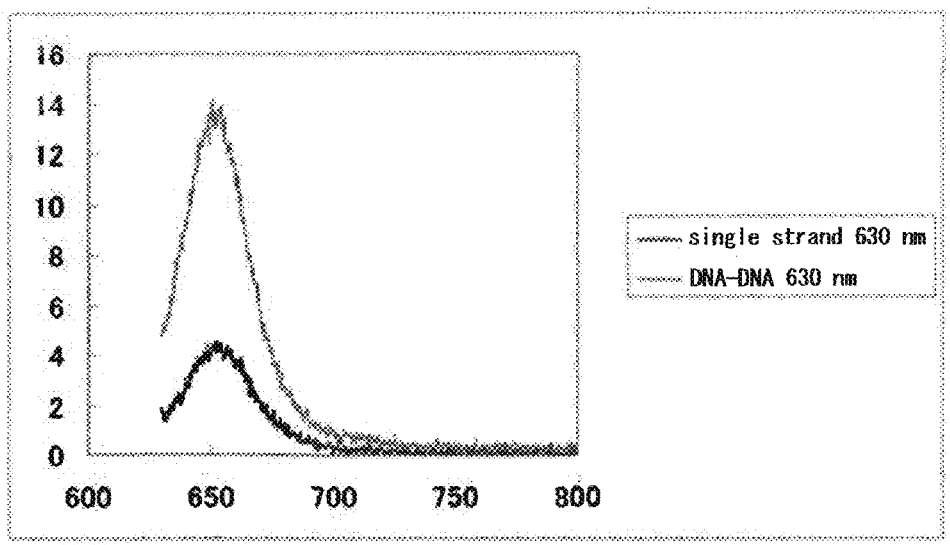

Compounds (oligodeoxyribonucleotides) represented by Formula 120, with n being 3, 4, 5, and 6, were synthesized in the same method. Furthermore, using ODN (referred to as ODN6 (n=5)) expressed by a sequence of 5'-d(CGCAAT[120]$_{(5)}$TAACGC)-3' as a fluorescence probe, the absorption spectrum and fluorescence emission spectrum were determined and the performance thereof was evaluated. The measurement conditions were the same as those employed in Example 7. FIG. 24 shows the measurement results. FIG. 24(a) shows the absorption spectra, with the horizontal axis indicating the wavelength (nm) and the vertical axis indicating the absorbance. FIG. 24(b) shows the fluorescence emission spectra, with the horizontal axis indicating the wavelength (nm) and the vertical axis indicating the emission intensity. The black line indicates the spectrum of the single-stranded ODN, and the gray line indicates the spectrum of the double-stranded ODN hybridized with a complementary ODN. As shown in FIG. 24(a), in the double-stranded ODN, the maximum wavelength of UV absorption around 600 nm was shifted to the longer wavelength side through the formation of a double helix. Furthermore, as shown in FIG. 24(b), in the double-stranded ODN, the fluorescence intensity increased considerably as compared to that of a single strand. Thus, it is conceivable that an exciton effect is exhibited in the single-stranded state. That is, although the ODN (Compound 120) of this example is different in absorption band from the ODN (Compound 113) of Example 8 and the ODN (Compound 117) of Example 11, it also exhibited a good exciton effect. This indicates that multicolor detection can be carried out using fluorescence probes that are different in absorption band from each other in the present invention.

Example 17

Formation of Double Strand with RNA

Figure 25:
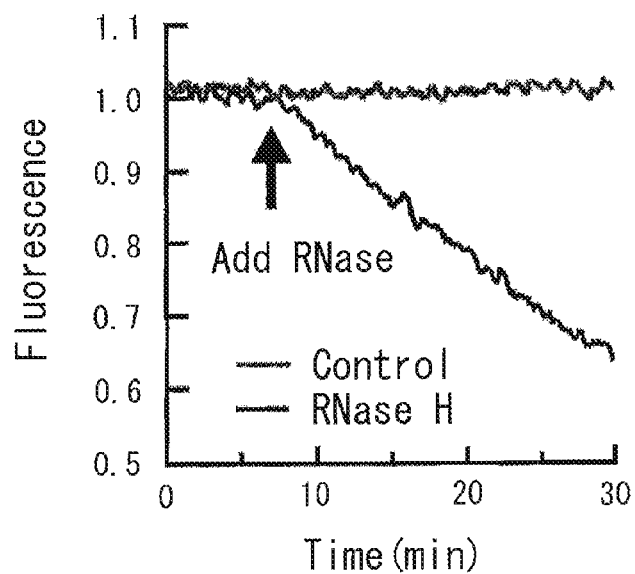
FIG. 25 is a diagram showing the change in fluorescence obtained when a RNA strand hybridized with a fluorescent probe of an example was digested with RNase H.

In a cuvette, a double-stranded ODN was formed with the ODN2 (with a sequence of 5'-d(TTTTTT[113]$_{(4)}$TTTTTT)-3') and a corresponding complementary RNA strand (RNA A13-mer), and the fluorescence emission spectrum thereof was measured. Furthermore, RNase H was added thereto, and the change in spectrum was observed. FIG. 25 shows the result. In FIG. 25, the horizontal axis indicates the time, and the vertical axis indicates the fluorescence intensity. In FIG. 25, the black line indicates the spectrum change of the double-stranded ODN to which RNase H was added during the measurement, and the gray line indicates the spectrum change of a control, i.e. the double-stranded ODN to which the RNase H was not added. The measurement was carried out using the fluorospectrometer, with stirring being performed at 37° C. As shown in FIG. 25, when the RNase H was added, the RNA that had been hybridized to the ODN2 was digested and thereby the ODN2 returned to a single strand, which resulted in a gradual decrease in fluorescence intensity. This also confirmed that the probe (nucleic acid) of the present invention was useful in fluorescence detection of complementary RNA.

Example 18

Figure 26:
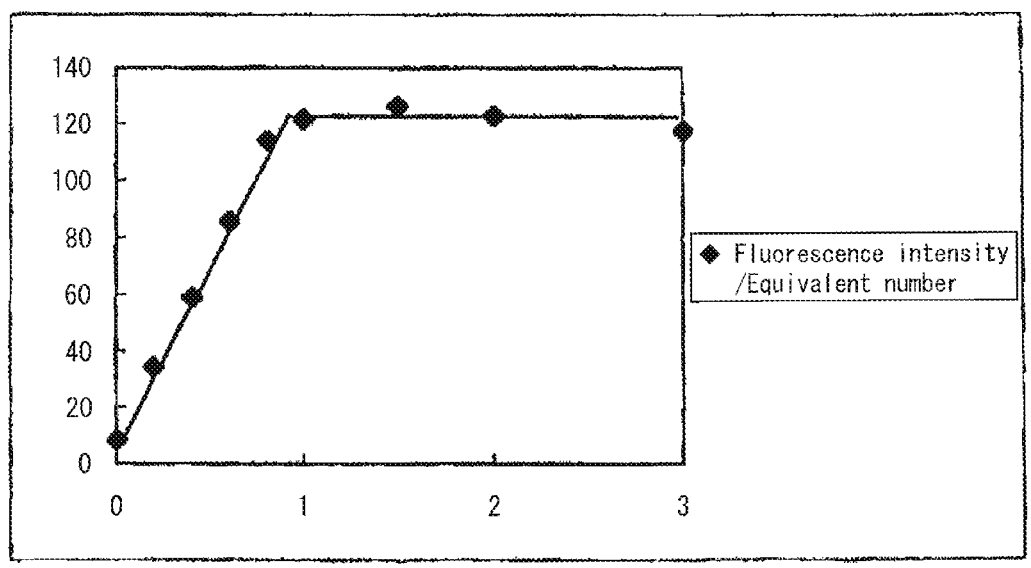
FIG. 26 is a diagram showing the results of observation of the change in fluorescence emission intensity obtained by changing the concentration ratio of the complementary DNA strand to a fluorescent probe according to an example.

The change in fluorescence emission intensity was observed with the concentration ratios of the ODN1' (with a sequence, 5'-d(GCGTTAAATTGCG)-3') being changed, where the ODN1' was a complementary DNA strand to the ODN1 (n=4) (with a sequence of 5'-d(CGCAAT[113]$_{(4)}$TAACGC)-3'). The measurement conditions were as follows. That is, the strand concentration of the ODN1 (n=4) was fixed at 1.0 µM, a 50 mM phosphoric acid buffer (pH 7.0) and 100 mM NaCl were used, and an excitation wavelength of 488 nm (with a width of 1.5 nm) was employed. The measurement was carried out, with the concentration of the complementary strand ODN1' being 0, 0.2, 0.4, 0.6, 0.8, 1.0, 1.5, 2.0, and 3.0 µM. The measurement results thereof are shown in FIG. 26. In FIG. 26, the horizontal axis indicating the equivalent number of the ODN1' with respect to the ODN1 (n=4), and the vertical axis indicates the fluorescence emission intensity (relative value) at $\lambda_{max}$ (529 nm) of fluorescence. As shown in FIG. 26, the fluorescence emission intensity indicated a directly proportional relationship with very high accuracy with respect to the equivalent number when the equivalent number of ODN1' was 1 or smaller, but it did not change after the equivalent number exceeded 1. This indicates that the ODN1 (n=4) hybridized with the ODN1' at an exact ratio of substance amounts (number ratio of molecules) of 1:1.

As described above, when the substance amount of the ODN1' (target DNA) is equal to or smaller than that of the ODN1 (n=4), the fluorescence intensity increases in proportion to the concentration of the target DNA. That is, it is possible to determine the quantity of the target DNA by measuring the fluorescence intensity when an excess of ODN1 (n=4) (probe) is added to the system where the ODN1' (target DNA) exists. Furthermore, it also is possible to determine the increase or decrease in the target DNA by tracing the increase or decrease in the fluorescence intensity.

In order to determine the quantity of the target DNA in the system, for example, a calibration curve may be prepared beforehand as shown in FIG. 26. For example, when a sample in which the concentration of ODN1' (target DNA) was unknown was measured under the same conditions as those employed in this example, if the fluorescence intensity obtained thereby was 80, the ODN1' (target DNA) concentration can be determined to be approximately 0.55 µM from FIG. 26.

In fact, when the quantity of the ODN1' (target DNA) sequence contained in nucleic acid was determined by the aforementioned method, it was possible not only to immediately detect the occurrence of phenomena such as amplification, degradation, and protein binding of the sequence concerned, but also to quantify such phenomena.

Example 19

Dot Blotting Analysis

With respect to a new probe (nucleic acid) synthesized this time, in order to observe the change in fluorescence properties that was caused by hybridization, a DNA analysis was carried out by dot blotting using the ODN (antiB1) and ODN (anti4.5S). For the target DNA sequence, a short-stranded DNA fragment containing the B1 RNA sequence was used. This sequence is one of the short interspersed nuclear elements of the rodent genome. Furthermore, the short-stranded DNA fragment contains the 4.5S RNA sequence. This sequence is one of the small nuclear RNAs isolated from a rodent cell and has extensive homology to the B1 family. In the present example, the ODN (antiB1) and ODN (anti4.5S) were prepared as blotting probes and two [113]$_{(4)}$ nucleotides were integrated thereinto, so that they were provided with a high sensitivity and a high fluorescence intensity. The structures of the ODN (antiB1) and ODN (anti4.5S) were as indicated in Table 5 in Example 13.

More specifically, the dot blotting analysis in the present example was carried out as follows. That is, first, the following two DNA fragments (1) and (2) were prepared with the automated DNA synthesizer.

(1) DNA double strand containing 4.5S RNA sequence and complementary DNA thereto as follows:

```
                                            (SEQ ID NO. 11)
5'-d(GCCGGTAGTGGTGGCGCACGCCGGTAGGATTTGCTGAAGGAGGCA

GAGGCAGGAGGATCACGAGTTCGAGGCCAGCCTGGGCTACACATTTTTT

T)-3'
```

(2) DNA double strand containing B1 RNA sequence and complementary DNA thereto as follows:

```
                                            (SEQ ID NO. 12)
5'-d(GCCGGGCATGGTGGCGCACGCCTTTAATCCCAGCACTTGGGAGGC

AGAGGCAGGCGGATTTCTGAGTTCGAGGCCAGCCTGGTCTACAGAGTGA

G)-3'
```

The DNA double strand was denatured with an aqueous solution containing 0.5 M sodium hydroxide and 1 M sodium chloride. An aliquot of this DNA thus denatured was dotted (spotted) on a positively charged nylon membrane (available from Roche). This positively charged nylon membrane sheet was moistened with an aqueous solution containing 0.5 M sodium phosphate and 1 M sodium chloride. Thereafter, it was incubated at 50° C. for 30 minutes in an aqueous solution containing 0.5 M sodium phosphate, 1 M sodium chloride, and 100 µg/mL salmon sperm DNA. Thereafter, the positively charged nylon membrane sheet was incubated at 50° C. for one hour in a probe aqueous solution (the probe was 150 µmol of ODN (anti4.5S) or ODN (antiB1)) containing 0.5 M sodium phosphate and 1 M sodium chloride. After this was cooled to room temperature, the hybridization buffer solution was removed, a new phosphoric acid buffer solution was added thereto, and fluorescence emitted by the positively charged nylon membrane sheet was observed with a Versa-Doc imaging system (trade name) available from BioRad. The excitation light used herein was light obtained by converting light emitted from an UV transilluminator Model-2270 (trade name) available from WAKENYAKU CO., LTD. by passing it through a UV/blue light converter plate (UVP).

Figure 27:
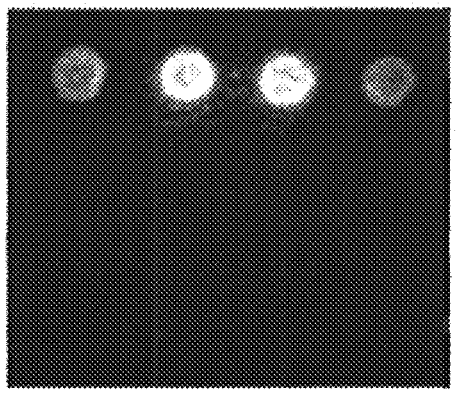
FIG. 27 shows diagrams illustrating the states of fluorescence emission in a blotting assay according to an example.
Figure 27:
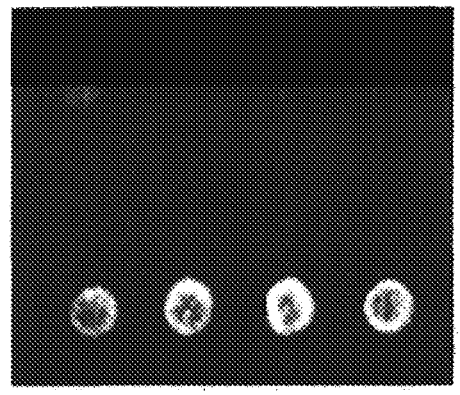

FIG. 27 shows the measurement results.

FIG. 27(a) is a schematic view showing the state where DNAs having different sequences from each other were blotted on a nylon membrane. The four spots in the upper row indicate 4.5S RNA sequence-containing DNA, and the four spots in the lower row indicate B1 RNA-containing DNA.

FIG. 27(b) is a diagram showing the fluorescence emission obtained after incubation was carried out in the ODN (anti4.5S)-containing solution.

FIG. 27(c) is a diagram showing the fluorescence emission obtained after incubation was carried out in the ODN (antiB1)-containing solution.

As shown in FIG. 27, it was possible to read the fluorescence of the blotted spots at room temperature with a fluorescence imaging system without carrying out washing repeatedly after the blotting assay. As a result of the incubation with the probes, when the ODN (anti4.5S) had been added, strong fluorescence emission derived from the spots of 4.5S sequence was obtained, but the fluorescence emission derived from the spots of B1 sequence was ignorable. By contrast, when the ODN (antiB1) had been added, the B1 spots exhibited strong fluorescence but only very weak fluorescence was observed from the 4.5S spots. Thus, the probe of the present invention can realize an assay that is clearly different from a conventional blotting assay in requiring neither a cumbersome multistep washing process nor an antibody or enzyme treatment process after blotting. Furthermore, unlike the on-off probe such as a molecular beacon, the probe of the present invention allows a plurality of fluorochrome-labeled portions to be introduced easily thereinto and thereby allows fluorescence intensity further to be increased. This is a great advantage of the present invention. The fluorochrome-labeled portions each may be, for example, one contained in $[113]_{(4)}$ nucleotide as in the present example.

Example 20

Figure 28:
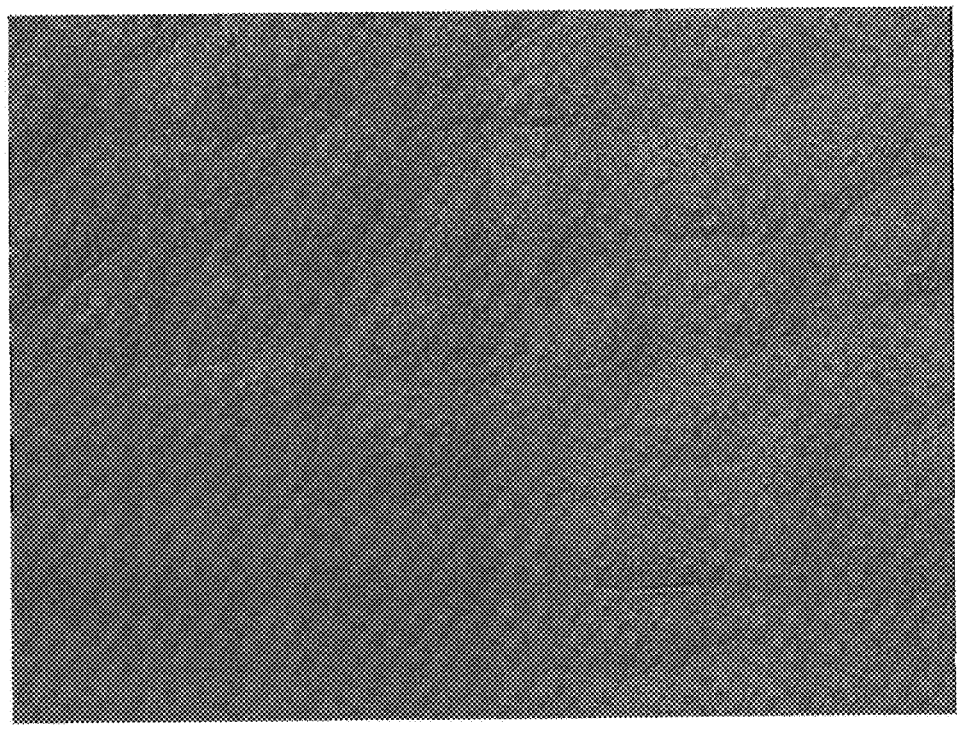
FIG. 28 is a photograph showing differential interference measured when a fluorescent probe of an example was introduced into a cell.
Figure 29:
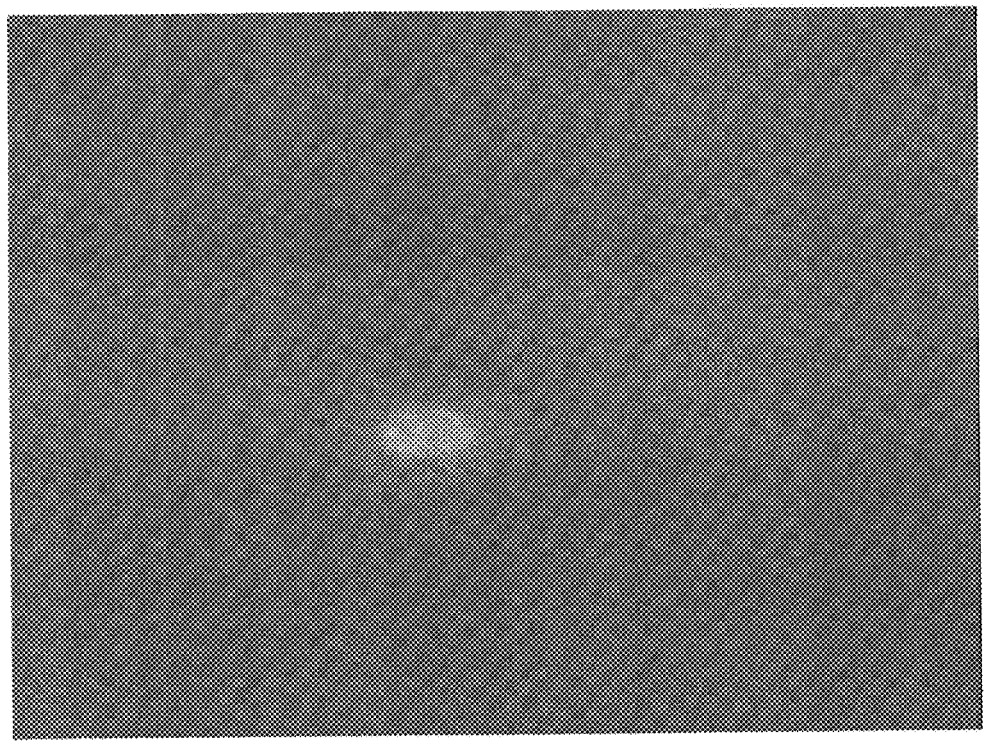
FIG. 29 is a photograph taken while fluorescence was observed when a fluorescent probe of an example was introduced into a cell.
Figure 30:
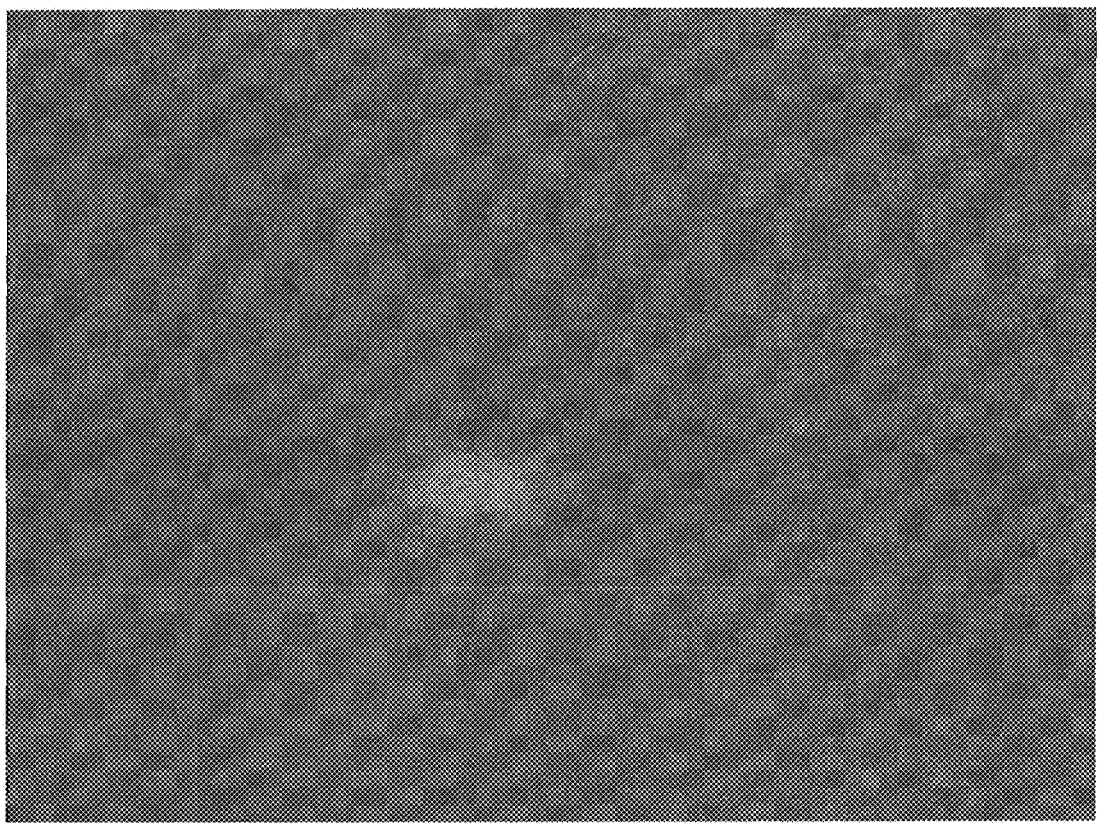
FIG. 30 is a photograph showing FIGS. 28 and 29 in a state of being superimposed on each other.

Poly T probe (the ODN2 described above) containing a dye with a linker length n of 4 used in Example 8 was introduced into a cell by microinjection technique using a micro glass tube, and the fluorescence emission was then measured with an inverted microscope equipped with a mercury lamp, a cooled CCD camera, and a fluorescence filter set (for YFP). FIGS. 28 to 30 show the results. FIG. 28 is a photograph taken in differential interferometry, FIG. 29 is a photograph taken during fluorescence observation, and FIG. 30 shows FIGS. 28 and 29 in state of being superimposed on each other. As shown in the figures, the fluorescence probe (labeling substance) of the present invention was bonded to a poly(A) end sequence of mRNA that was expressed intracellularly, and thereby emitted light. That is, the labeled DNA oligomer of the present invention is effective not only for in vitro gene detection but also in vivo gene detection.

Example 21

Figure 31A:
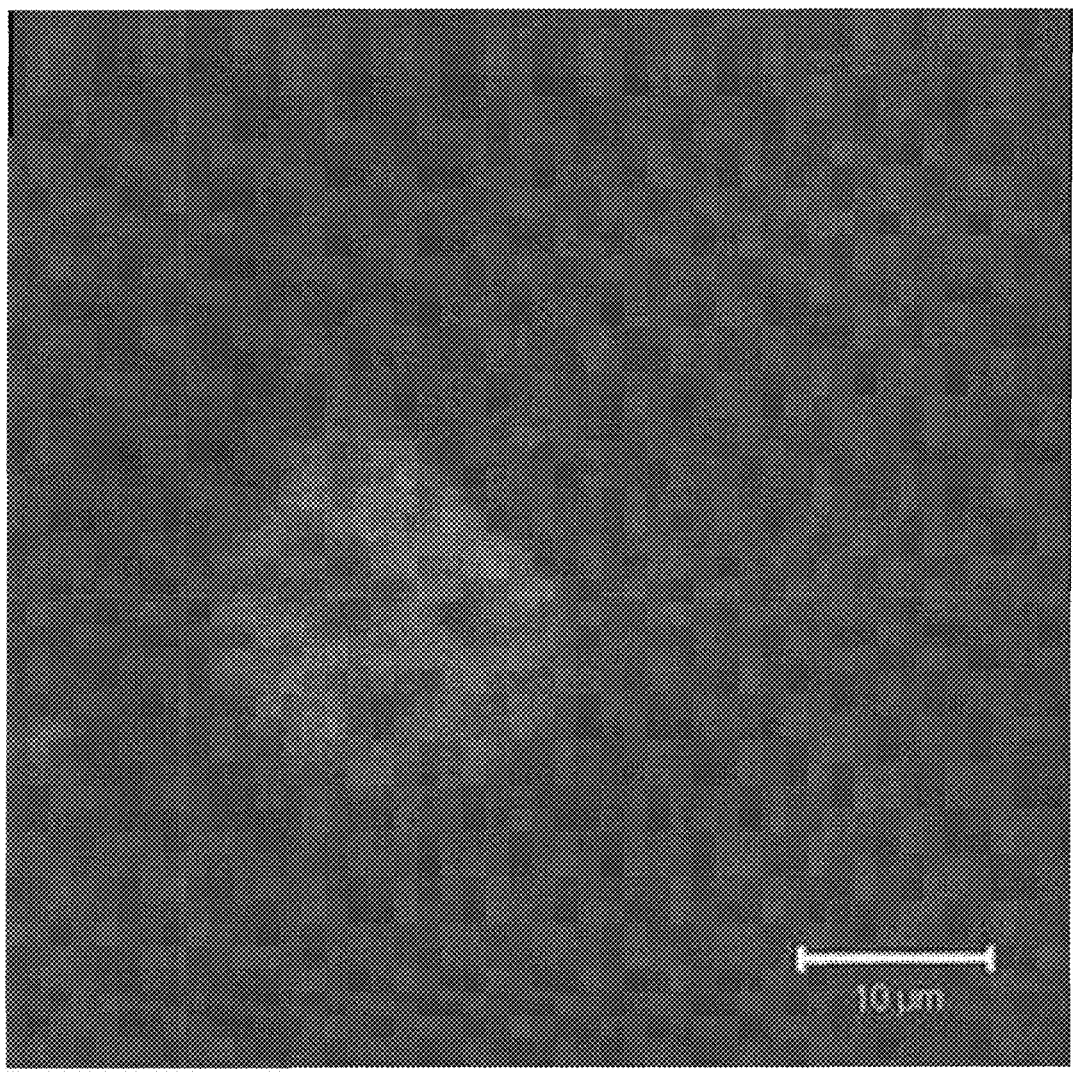
FIG. 31A is a photograph taken while fluorescence was observed when another fluorescent probe of an example was introduced into a cell.
Figure 31B:
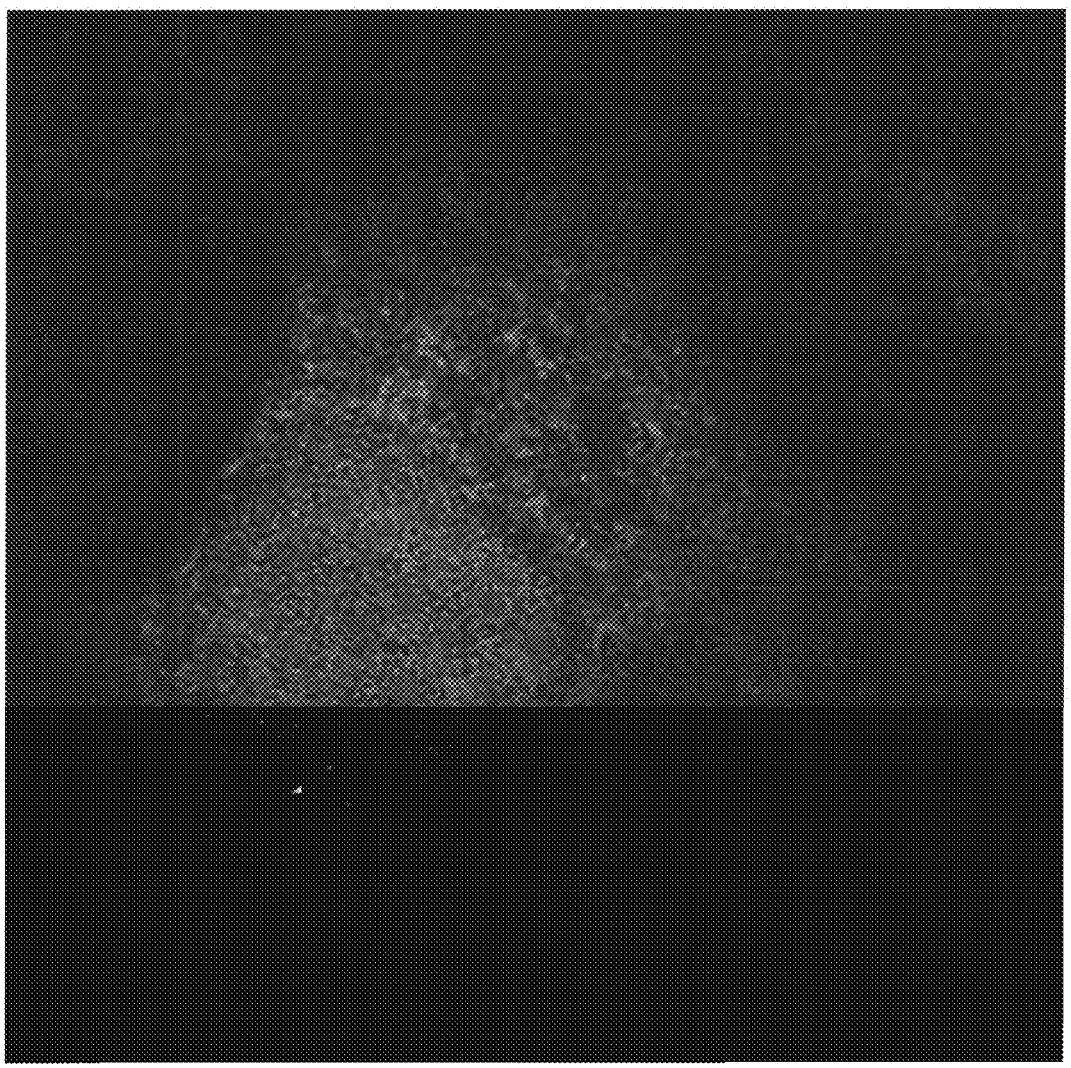
FIG. 31B is a photograph taken while fluorescence was observed when another fluorescent probe of an example was introduced into a cell.

Further, a common fluorescent dye, Cy5, was bonded to the ODN2 (with a sequence of 5'-d(TTTTTT[113]$_{(4)}$TTTTTT)-3') by a conventional method, which further was introduced into a cell by the aforementioned method. In this case, Cy5 was added to the 5' end of the ODN2 with an automated DNA synthesizer to be bonded thereto in the process of synthesizing the ODN2 (with a sequence of 5'-Cy5-d(TTTTTT[113]$_{(4)}$TTTTTT)-3'). The fluorescence emission was measured with a laser scanning confocal microscope. FIG. 31 shows the result. FIG. 31A shows fluorescence derived from Cy5, with the fluorescence with a wavelength of at least 650 nm being obtained by excitation at 633 nm. FIG. 31B shows fluorescence derived from two thiazole orange portions, with the fluorescence between 505 nm and 550 nm being obtained by excitation at 488 nm. As shown in the figures, the ODN2 was bonded to the poly(A) end sequence of mRNA that was expressed intracellularly, and thereby emitted light. This allowed the distribution of intracellular mRNAs to be traced. As described above, a plurality of types of dyes (atomic groups that exhibit fluorescence) may be introduced into the compound or nucleic acid of the present invention. This also allows multicolor detection to be carried out, since, for example, respective dyes are different in $\lambda_{max}$ of fluorescence from each other.

Example 22

Figure 32:
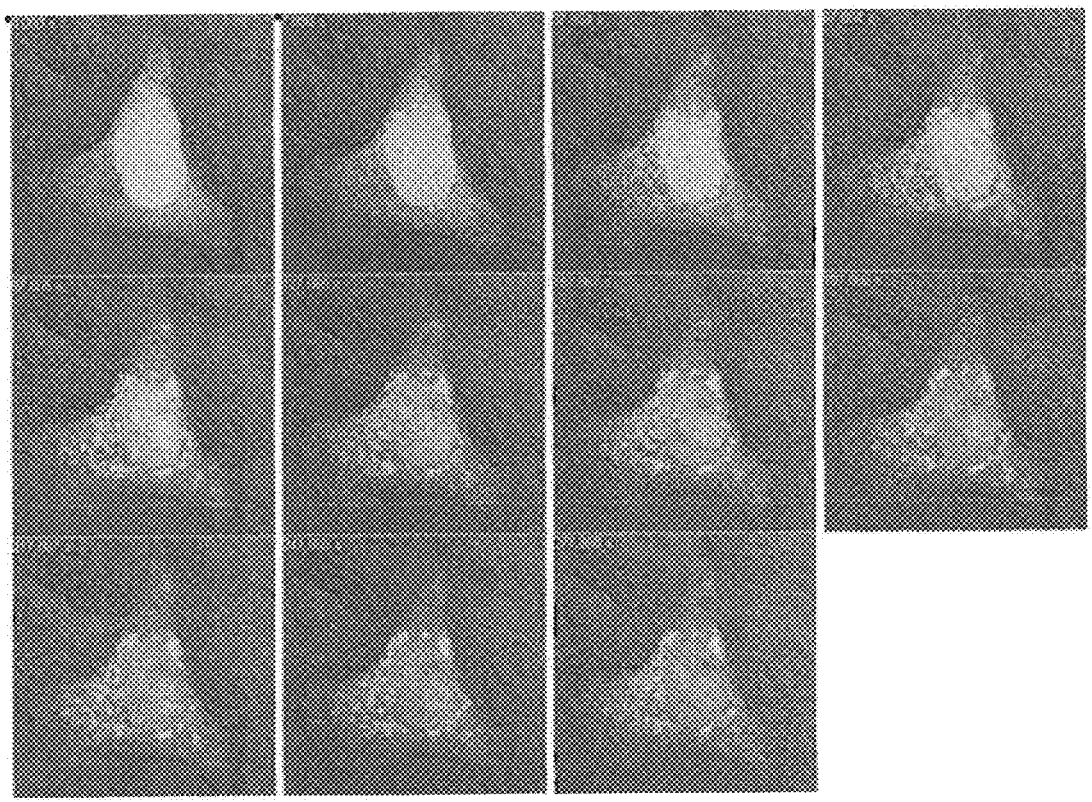
FIG. 32 shows diagrams illustrating the change in fluorescence with time after an identical probe to that shown in FIGS. 28 to 30 was injected into a cell nucleus.

The aforementioned ODN2 (with a sequence of 5'-d(TTTTTT[113]$_{(4)}$TTTTTT)-3') was injected into a cell nucleus by the aforementioned method, and the fluorescence emission was traced with the laser scanning confocal microscope from immediately after injection (0 second) to approximately 4.5 minutes (excitation at 488 nm, and fluorescence obtained between 505 nm and 550 nm). FIG. 32 shows the result. FIG. 32 include 11 diagrams that show the progress after injection of the ODN2, from left to right and from upper row toward lower row. In each diagram, the elapsed time (after injection of the ODN2) is as indicated in Table 8 below. As shown in FIG. 32, it was confirmed that the probe ODN2 was concentrated in the cell nucleus immediately after injection thereof but was dispersed gradually throughout the cell together with mRNA (poly A) hybridized therewith. According to the present invention, it also is possible to trace mRNA in the manner as described above.

TABLE 8

| 0 sec | 8 sec | 38 sec | 68 sec |
|---|---|---|---|
| 98 sec | 128 sec | 158 sec | 188 sec |
| 218 sec | 248 sec | 278 sec | — |

Example 23

An ODN was synthesized, in which the number of Ts located on each side of $[113]_{(4)}$ of the ODN2 was increased to 24. This is referred to as "ODN7". This was synthesized by the same method as that of synthesizing the ODN2. The sequence of the ODN7 is:

(SEQ ID NO. 13)
5'-d(TTTTTTTTTTTTTTTTTTTTTTTT[113]$_{(4)}$TTTTTTTTTTTT

TTTTTTTTTTTT)-3').

Figure 33:
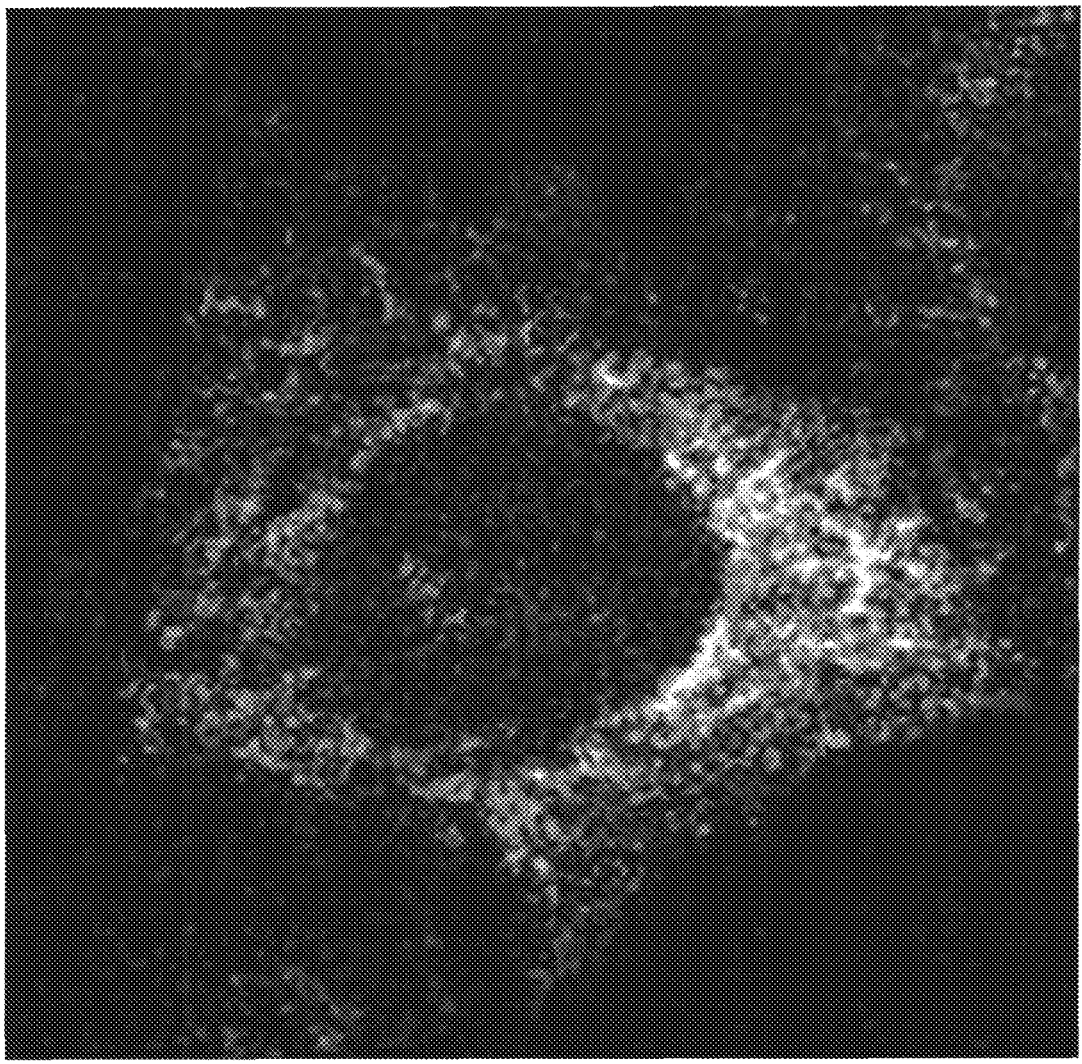
FIG. 33 is a photograph taken while fluorescence was observed when another fluorescent probe of an example was introduced into a cell.

This was injected into a cell nucleus by the same method as that employed in Example 22, and the fluorescence intensity was measured. FIG. 33 shows a fluorescence photograph taken after a lapse of a certain period of time. The ODN7 was concentrated in the cell nucleus immediately after injection but was dispersed gradually throughout the cell together with mRNA (poly A) hybridized therewith, as in Example 22, and finally, it was dispersed around the cell nucleus as shown in FIG. 33.

Example 24

Multicolor Detection

As described in, for instance, Examples 11 and 16, the fluorescence probes of the present invention allow multicolor detection of complementary strands by having, for example, different absorption wavelengths and emission wavelengths from each other. This multicolor detection can be achieved by using dye (atomic group exhibiting fluorescence) portions having different structures as in the cased of Compounds 113, 117, and 120. In the present example, further various fluorescence probes were synthesized (produced) and multicolor detection of complementary strands was carried out.

First, DNA strands (probes), each of which contained a nucleotide structure represented by the following formula (121), were synthesized, with the structures of dye (atomic group exhibiting fluorescence) portions being varied. In the following formula (121), "Dye" denotes the dye portion.

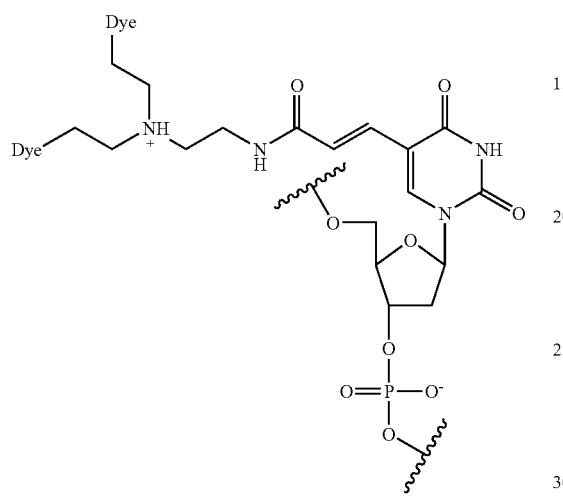

(121)

Specifically, compounds (DNA strands) 113, 120, 122, 123, and 124 were synthesized, which contain portions represented by the following formulae, respectively, as the "Dye" portion contained in the formula (121). In the following formulae, n is the linker length (the number of carbon atoms). With respect to the compounds 113, 120, 122, 123, and 124, compounds whose linker lengths n were 3, 4, 5, and 6 were synthesized, respectively. The synthesis was carried out by the same method as that employed in Examples 1 to 4, 6, 8, 9, 12, 13, and 16 except for using dyes with corresponding structures, respectively, instead of the dye 107. The synthesis of the dyes that replace the dye 107 also was carried out in the same manner as in the synthesis of the dye 107 (Scheme 5 in Example 6) except that the structures of the raw materials were changed suitably. Furthermore, Compounds 113 and 120 have the same structures as those of Compounds 113 and 120 of the respective examples described above, respectively.

(113)

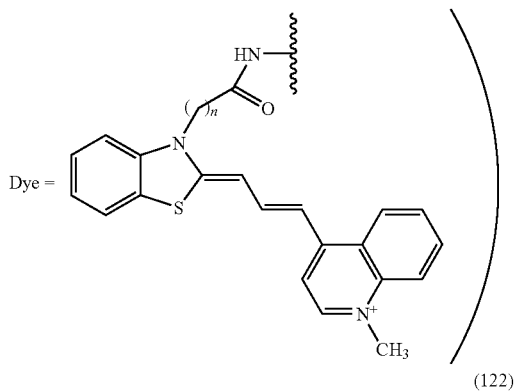

(120)

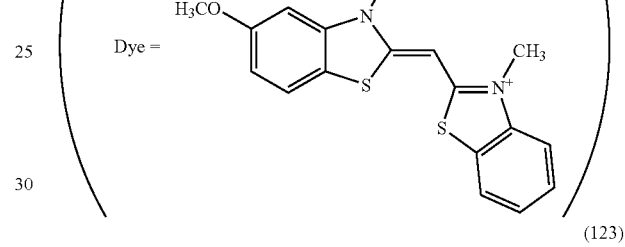

(122)

(123)

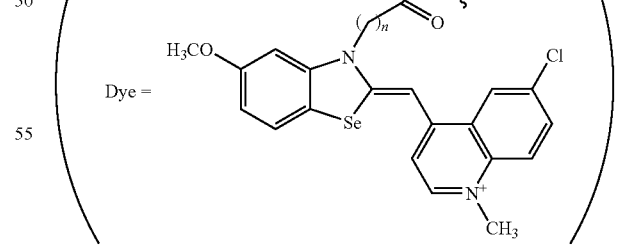

(124)

With respect to Compounds 113, 120, 122, 123, and 124, ODNs were synthesized, each of which was represented by a sequence of 5'-d(CGCAATX$_{(n)}$TAACGC)-3', where X is 113, 120, 122, 123, or 124, and n is the linker length. An ODN represented by a sequence of 5'-d(CGCAAT[113]$_{(n)}$TAACGC)-3' is identical to the aforementioned ODN1. An ODN represented by a sequence of 5'-d(CGCAAT[120]$_{(n)}$ TAACGC)-3' is identical to the aforementioned ODN6. An ODN represented by a sequence of 5'-d(CGCAAT[122]$_{(n)}$TAACGC)-3' is referred to as an "ODN8". An ODN represented by a sequence of 5'-d(CGCAAT[123]$_{(n)}$TAACGC)-3' is referred to as an "ODN9". An ODN represented by a sequence of 5'-d(CGCAAT[124]$_{(n)}$TAACGC)-3' is referred to as an "ODN10". With respect to each of the ODN1, ODN6, ODN8, ODN9, and ODN10, ODNs with linker lengths n of 3, 4, 5, and 6 were synthesized, respectively.

With respect to each of the ODN1 (n=4), ODN6 (n=4), ODN8 (n=4), ODN9 (n=4), and ODN10 (n=4), after each of them was allowed to form a double strand together with a complementary strand, ODN1', the fluorescence emission spectrum was measured. The measurement conditions were the same as those employed in each example described above except for the excitation wavelength. The result is indicated in Table 9 below. In Table 9, $E_x$ denotes excitation wavelength, and $E_m$ indicates the maximum wavelength of fluorescence emission. The excitation wavelength $E_x$ was set so as to be almost equal to the maximum wavelength $\lambda_{max}$ of absorption.

TABLE 9

| Structure of double strand | $E_x$ | $E_m$ |
|---|---|---|
| 5'-d(CGCAAT[113]$_{(4)}$TAACGC-3' (ODN1 (n = 4)/ODN1' | 514 nm | 528 nm |
| 5'-d(CGCAAT[120]$_{(4)}$TAACGC-3' (ODN6 (n = 4)/ODN1' | 650 nm | 654 nm |
| 5'-d(CGCAAT[122]$_{(4)}$TAACGC-3' (ODN8 (n = 4)/ODN1' | 436 nm | 456 nm |
| 5'-d(CGCAAT[123]$_{(4)}$TAACGC-3' (ODN9 (n = 4)/ODN1' | 534 nm | 550 nm |
| 5'-d(CGCAAT[124]$_{(4)}$TAACGC-3' (ODN10 (n = 4)/ODN1' | 541 nm | 563 nm |

As can be seen from Table 9, when the respective ODNs each formed a double strand, they exhibited different maximum wavelengths $E_m$ of fluorescence emission from one another in a wide wavelength range from 456 nm to 654 nm. That is, it was possible to carry out multicolor detection of complementary strand DNAs using the ODNs synthesized in this example (Example 24). Furthermore, with respect to Compounds (DNA strands) 113, 120, 122, 123, and 124 as well as ODN1, ODN6, ODN8, ODN9, and ODN10 of this reference example, their use in the same manner as in the respective examples described above, for example, detection of complementary strand RNA, dot blotting analysis, and detection of intracellular mRNA were carried out by multicolor, was confirmed.

Industrial Applicability

As described above, the present invention can provide a labeling substance that allows the double helix structure of a nucleic acid to be detected effectively, for example. The present invention also can provide a nucleic acid detection method and kit, that use the above-described labeling substance. The compound or nucleic acid of the present invention has a characteristic structure shown in the formula (1), (1b), (1c), (16), (16b), (17), (17b), (18), or (18b), so that it can be used as, for example, a labeling substance that allows the double helix structure of a nucleic acid to be detected effectively. Since the labeling substance of the present invention is excellent in detection sensitivity of a nucleic acid, it can be used for a wide range of applications, for example, study, clinical use, diagnosis, in vitro gene detection, and in vivo gene detection. Furthermore, the use of the compound and nucleic acid of the present invention is not limited thereto, and they can be used for any applications.

The invention claimed is:

1. A nucleic acid comprising at least one of structures represented by the following formulae (16), (16b), (17) or (17b) a tautomer or stereoisomer of the nucleic acid; or a salt of the nucleic acid, the tautomer, or the stereoisomer:

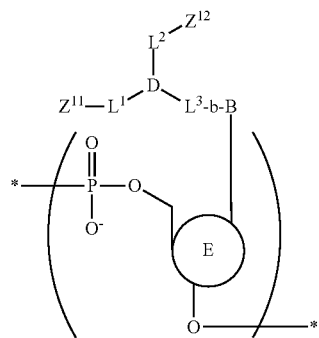

(16)

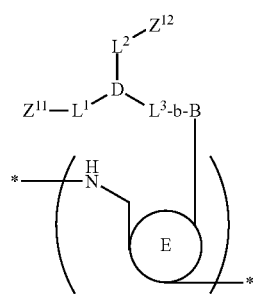

(16b)

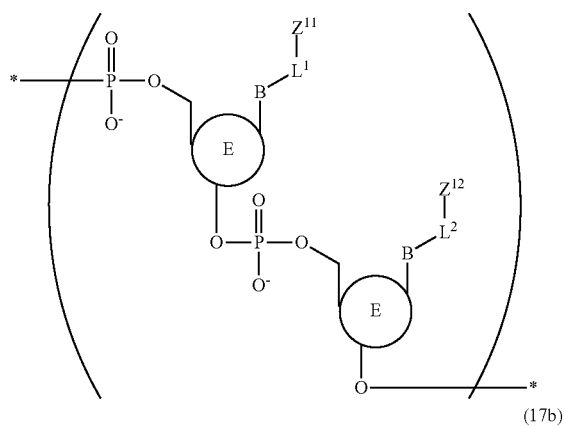

where in the formulae (16), (16b), (17) and (17b),
B is an atomic group having a natural nucleobase (adenine, guanine, cytosine, thymine, or uracil) skeleton or an artificial nucleobase skeleton,
each of $Z^{11}$ and $Z^{12}$ is an atomic group that exhibits fluorescence and exhibits an exciton effect, and $Z^{11}$ and $Z^{12}$ may be identical to or different from one another,
each of $L^1$, $L^2$, and $L^3$ is a linker (a linking atom or an atomic group), a length of a main chain (the number of main chain atoms) is arbitrary, each of $L^1$, $L^2$, and $L^3$ may or may not contain C, N, O, S, P, or Si in the main chain, each of $L^1$, $L^2$, and $L^3$ may or may not contain a single bond, a double bond, a triple bond, an amide bond, an ester bond, a disulfide bond, an imino group, an ether bond, a thioether bond, or a thioester bond in the main chain, and $L^1$, $L^2$, and $L^3$ may be identical to or different from one another, D is CR, N, P, P=O, B, or SiR, and R is a hydrogen atom, an alkyl group, or an arbitrary substituent, b is a single bond, a double bond, or a triple bond, or in the formula (16) and (16b), each of $L^1$ and $L^2$ is a linker, $L^3$, D, and b may not be present, and $L^1$ and $L^2$ may be bonded directly to B, where in the formulae (16) and (17), E is an atomic group having a deoxyribose skeleton, a ribose skeleton, or a structure derived from either one of them, and at least one O atom in a phosphoric acid linkage may be substituted with an S atom, in the formulae (16b) and (17b), E is an atomic group having a peptitude structure or a peptoid structure, and in the formulae (17) and (17b), the respective Bs may be identical to or different from each other, and the respective Es may be identical to or different from each other.

2. The nucleic acid according to claim 1, wherein in the formulae (16), (17), (16b) and (17b), $Z^{11}$ and $Z^{12}$ are each an atomic group that exhibits fluorescence, and may be identical to or different from each other;

a tautomer or stereoisomer of the nucleic acid; or a salt of the nucleic acid, the tautomer, or the stereoisomer.

3. The nucleic acid according to claim 1, wherein in the formulae (16) and (17), E is an atomic group having a main chain structure of DNA, modified DNA, RNA, modified RNA, or LNA;

a tautomer or stereoisomer of the nucleic acid; or a salt of the nucleic acid, the tautomer, or the stereoisomer wherein in the formulae (16b) and (17b), E is an atomic group having a main chain structure of PNA (peptide nucleic acid);

a tautomer or stereoisomer of the nucleic acid; or a salt of the nucleic acid, the tautomer, or the stereoisomer.

4. The nucleic acid according to claim 1, wherein in the formulae (16), the atomic group represented by:

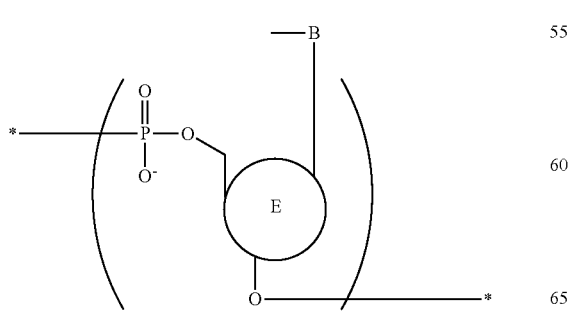

is an atomic group represented by the following formulae (2-1) or (3-1),

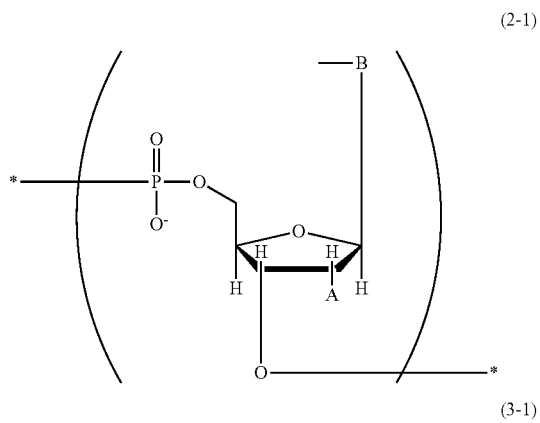

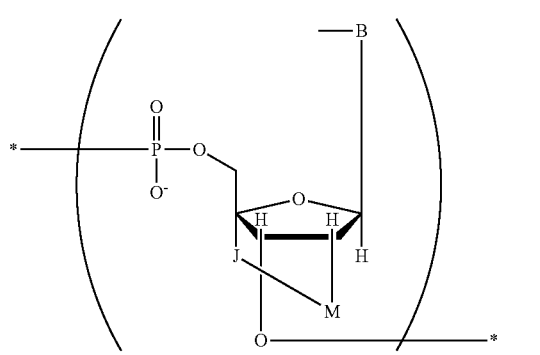

in the formula (16b), an atomic group represented by:

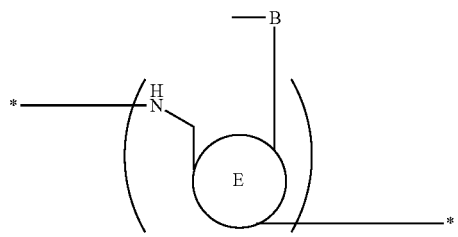

is an atomic group represented by the following formulae (4-1),

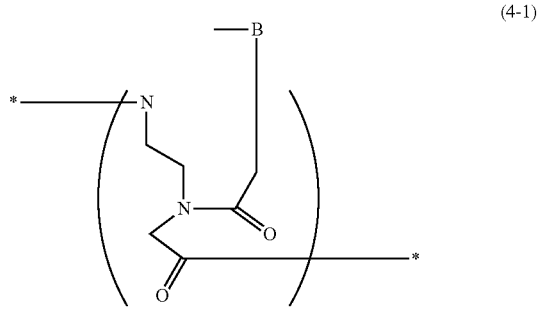

in the formula (17), an atomic group represented by:

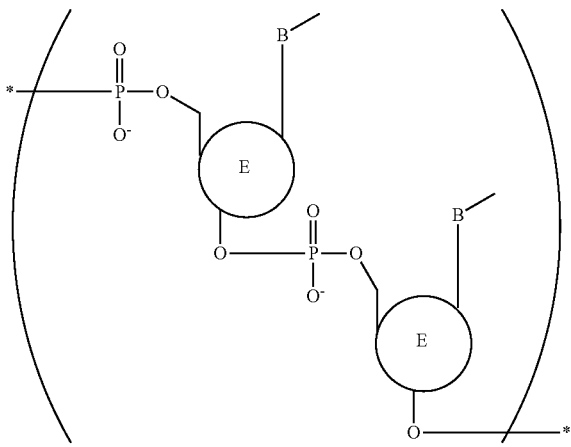

is an atomic group represented by the following formulae (2b-1) or (3b-1), (2b-1)

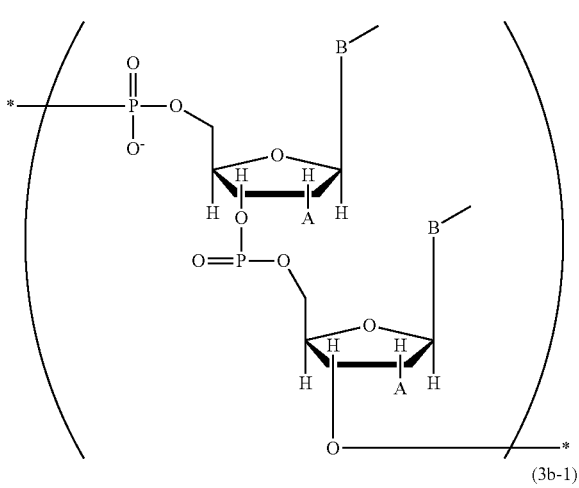

(3b-1)

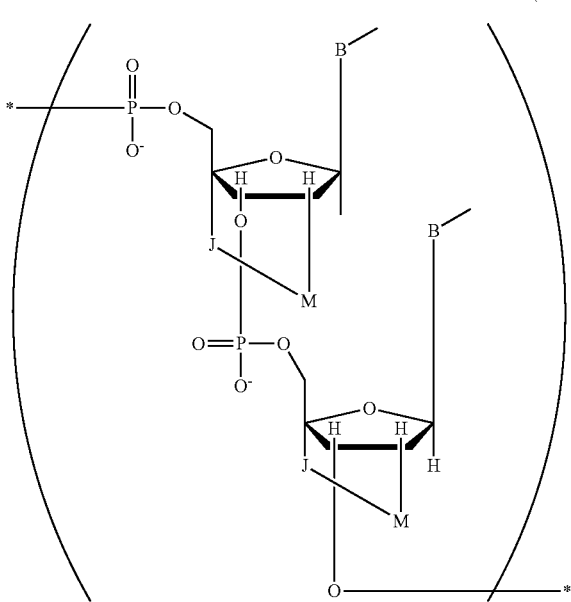

in the formula (17b), an atomic group represented by:

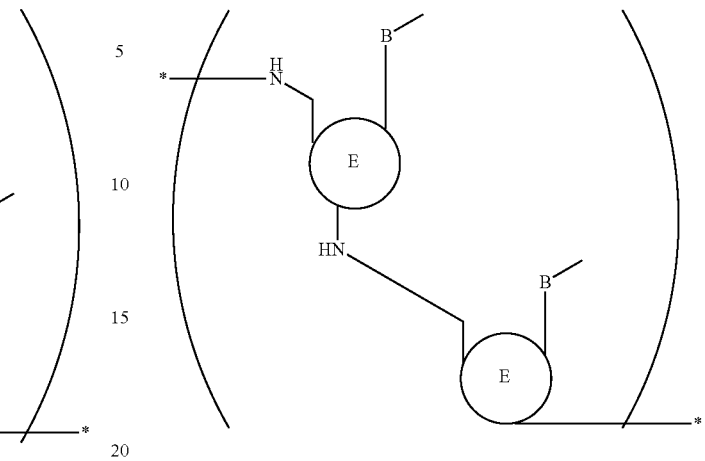

is an atomic group represented by the following formulae (4b-1), (4b-1)

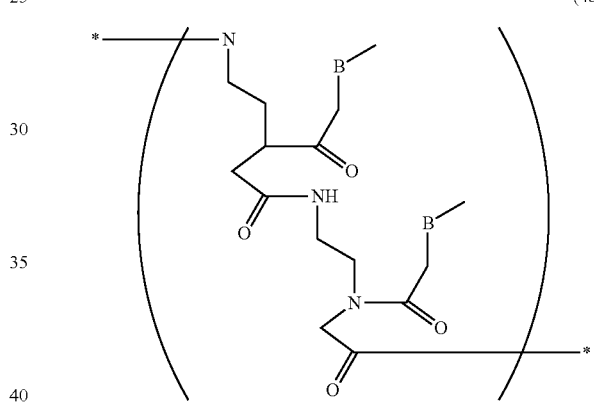

in the formulae (2-1), (3-1), (4-1), (2b-1), (3b-1), and (4b-1),
B is the same as in the formula (16), (16b), (17) and (17b),
in the formulae (2-1) and (2b-1),
A is a hydrogen atom, a hydroxy group, an alkyl group, a methoxy group, or an electron-withdrawing group,
in the formulae (3-1) and (3b-1),
M and J are each $CH_2$, NH, O, or S and may be identical to or different from each other, and
in the formulae (2-1), (3-1), (2b-1), and (3b-1), at least one O atom contained in a phosphoric acid linkage may be substituted with an S atom;
a tautomer or stereoisomer of the nucleic acid; or
a salt of the nucleic acid, the tautomer, or the stereoisomer.

5. The nucleic acid according to claim 4, wherein, in the formulae (2-1) and (2b-1), the electron-withdrawing group is halogen;
a tautomer or stereoisomer of the nucleic acid; or
a salt of the nucleic acid, the tautomer, or the stereoisomer.

6. The nucleic acid according to claim 1, wherein, in the formula (16), (16b), (17) or (17b), each main chain length (the number of main chain atoms) of $L^1$, $L^2$, and $L^3$ is an integer of 2 or more;
a tautomer or stereoisomer of the nucleic acid; or
a salt of the nucleic acid, the tautomer, or the stereoisomer.

7. The nucleic acid according to claim 1, represented by the following formula (16-1), (16-2), (16b-1), (16b-2), (17-1), or (17b-1); a tautomer or stereoisomer of the nucleic acid; or a salt of the nucleic acid, the tautomer, or the stereoisomer:

(16-1)

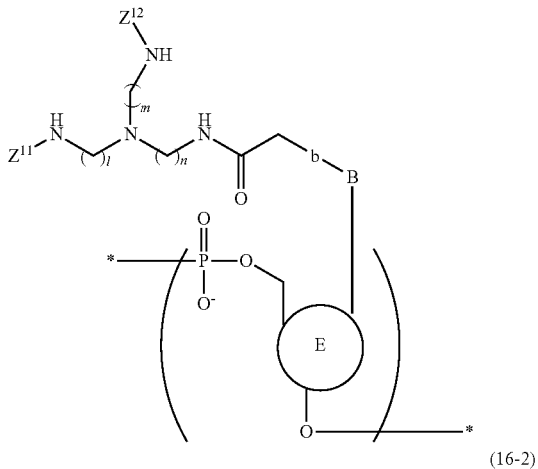

(16-2)

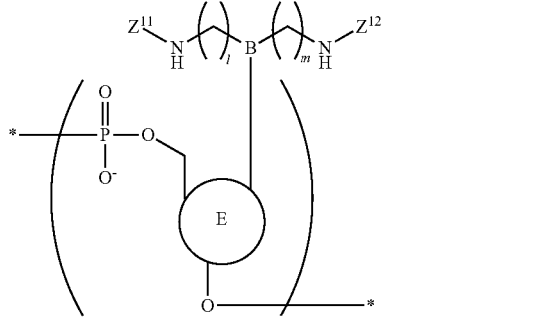

(16b-1)

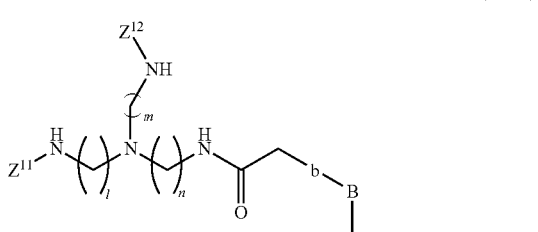

(16b-2)

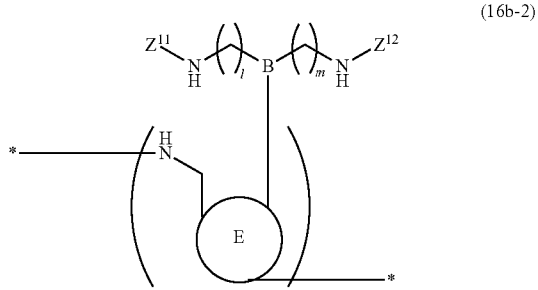

wherein the formulae (16-1), (16-2), (16b-1), (16b-2), (17-1), and (17b-1), the line length l, m, and n are arbitrary and may be identical to or different from one another, the linkers may or may not contain each of C, N, O, S, P, and Si in the main chain, the linkers each may or may not contain each of a single bond, a double bond, a triple bond, an amide bond, an ester bond, a disulfide bond, an imino group, an ether bond, a thioether bond, and a thioester bond in the main chain, and each of B, E, $Z^{11}$ and $Z^{12}$ is the same as in the formula (16), (16b), (17), or (17b), respectively, in the formulae (16-1) and (16b-1), b is the same as in the formula (16) or (16b).

8. The nucleic acid according to claim 7, wherein l, m, and n each are an integer of 2 or more;

a tautomer or stereoisomer of the nucleic acid; or a salt of the nucleic acid, the tautomer, or the stereoisomer.

9. The nucleic acid according to claim 1, wherein $Z^{11}$ and $Z^{12}$ are each independently a group derived from thiazole orange, oxazole yellow, cyanine, hemicyanine, another cyanine dye, methyl red, azo dye, or a derivative thereof;

a tautomer or stereoisomer of the nucleic acid; or a salt of the nucleic acid, the tautomer, or the stereoisomer.

10. The nucleic acid according to claim 1, wherein $Z^{11}$ and $Z^{12}$ are each independently an atomic group represented by any one of the following formulae (7) to (9): a tautomer or stereoisomer of the nucleic acid; or a salt of the nucleic acid, the tautomer, or the stereoisomer:

(7)

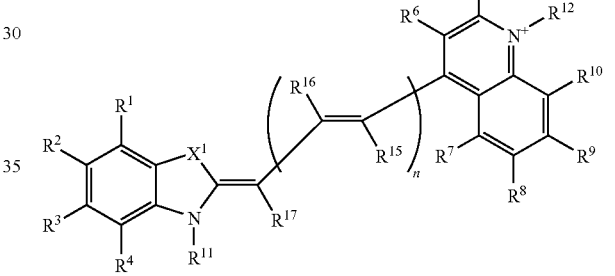

(8)

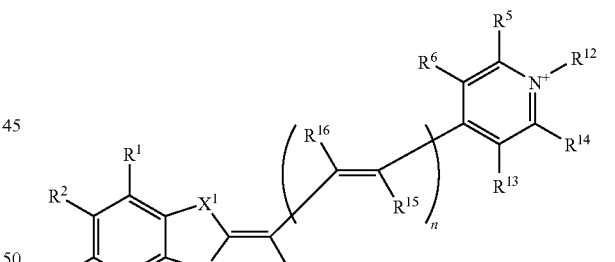

(9)

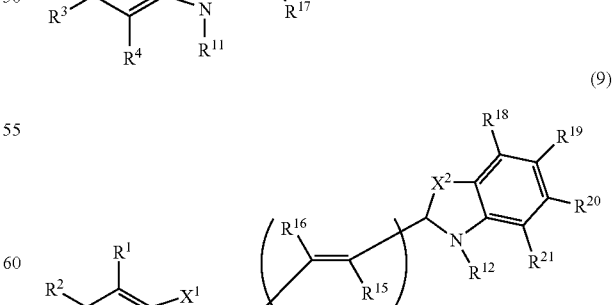

where in the formulae (7) to (9),
X¹ and X² are each S or O and may be identical to or different from each other,
n is 0 or a positive integer,
$R^1$ to $R^{10}$ and $R^{13}$ to $R^{21}$ are each independently a hydrogen atom, a halogen atom, a lower alkyl group, a lower alkoxy group, a nitro group, or an amino group,
one of $R^{11}$ and $R^{12}$ is a linking group that binds to $L^1$ or $L^2$ in the formula (16), (16b), (17) or (17b) or NH in the formula (16-1), (16-2), (16b-1), (16b-2), (17-1), or (17b-1), and the other is a hydrogen atom or a lower alkyl group,
  when a plurality of $R^{15}$s are present in the formula (7), (8), or (9), the plurality of $R^{15}$s may be identical to or different from each other,
  when a plurality of $R^{16}$s are present in the formula (7), (8), or (9), the plurality of $R_{16}$s may be identical to or different from each other, and
  $X^1$, $X^2$ and $R^1$ to $R^{21}$ in $Z^{11}$ and $X^1$, $X^2$ and $R^1$ to $R^{21}$ in $Z^{12}$ may be identical to or different from each other, respectively.

11. The nucleic acid according to claim 10, wherein in the formulae (7) to (9), in $R^1$ to $R^{21}$, the lower alkyl group is a linear or branched alkyl group with a carbon number of 1 to 6, and the lower alkoxy group is a linear or branched alkoxy group with a carbon number of 1 to 6;
  a tautomer or stereoisomer of the nucleic acid; or
  a salt of the nucleic acid, the tautomer, or the stereoisomer.

12. The nucleic acid according to claim 10, wherein in the formulae (7) to (9), in $R^{11}$ and $R^{12}$, the linking group is a polymethylene carbonyl group with a carbon number of at least 2 and binds to $L^1$ or $L^2$ in the formula (16), (16b), (17) or (17b) or NH in the formula (16-1), (16-2), (16b-1), (16b-2), (17-1), or (17b-1), by a carbonyl group moiety thereof;
  a tautomer or stereoisomer of the nucleic acid; or
  a salt of the nucleic acid, the tautomer, or the stereoisomer.

13. The nucleic acid according to claim 1, having a structure represented by the following formula (10-1) or (10-2); a tautomer or stereoisomer of the nucleic acid; or a salt of the nucleic acid, the tautomer, or the stereoisomer:

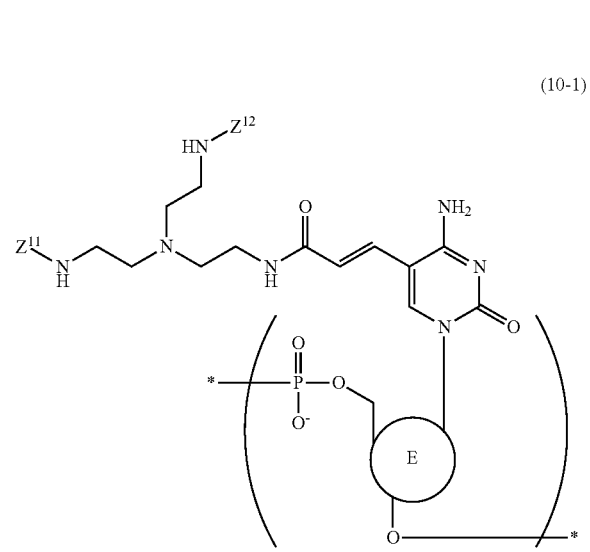

(10-1)

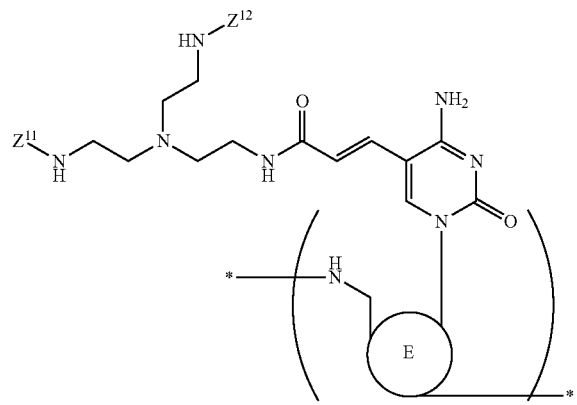

(10-2)

where in the formula (10-1),
  E, $Z^{11}$, and $Z^{12}$ are the same as in the formula (16);
in the formula (10-2),
  E, $Z^{11}$, and $Z^{12}$ are the same as in the formula (16b).

14. The nucleic acid according to claim 1, wherein in the formulae (16), (16b), (17) and (17b), B is a structure represented by Py, Py der., Pu, or Pu der.; a tautomer or stereoisomer of the nucleic acid; or a salt of the nucleic acid, the tautomer, or the stereoisomer:
where
  the Py is an atomic group having a covalent bond to E in a 1-position and a covalent bond to a linker moiety in a 5-position in a six-membered ring represented by the following formula (11),
  the Py der. is an atomic group in which at least one of all the atoms of the six-membered ring of the Py has been substituted with an N, C, S, or O atom, and the N, C, S, or O atom may have an electric charge, a hydrogen atom, or a substituent optionally,
  the Pu is an atomic group having a covalent bond to E in a 9-position and a covalent bond to a linker moiety in an 8-position in a condensed ring represented by the following formula (12), and
  the Pu der. is an atomic group in which at least one of all the atoms of a five-membered ring of the Pu has been substituted with an N, C, S, or O atom, and the N, C, S, or O atom may have an electric charge, a hydrogen atom, or a substituent optionally.

(11)

(12)

15. The nucleic acid according to claim 1, having a structure represented by the following formula (13-1), (13-2), (14-1) or (14-2), a tautomer or stereoisomer of the nucleic acid; or a salt of the nucleic acid, the tautomer, or the stereoisomer:

(13-1)

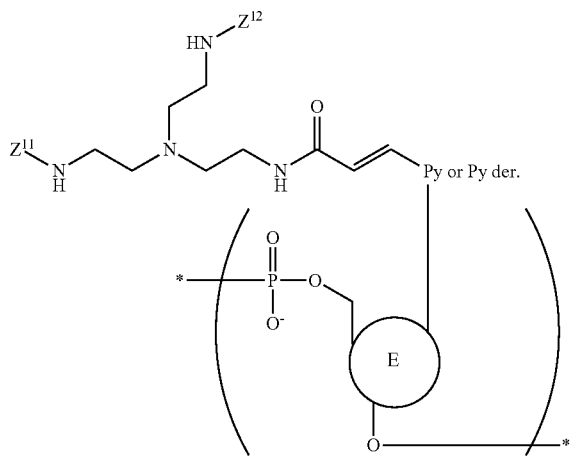

(13-2)

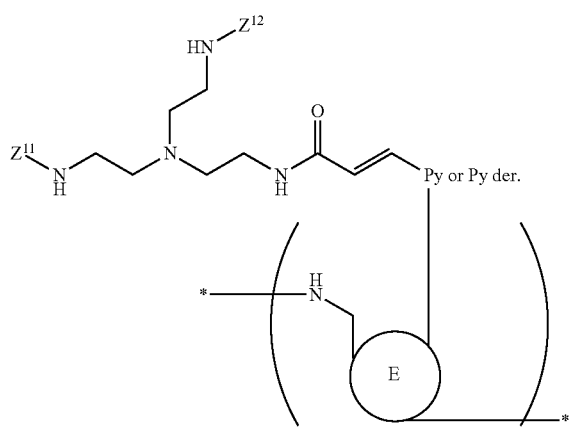

(14-1)

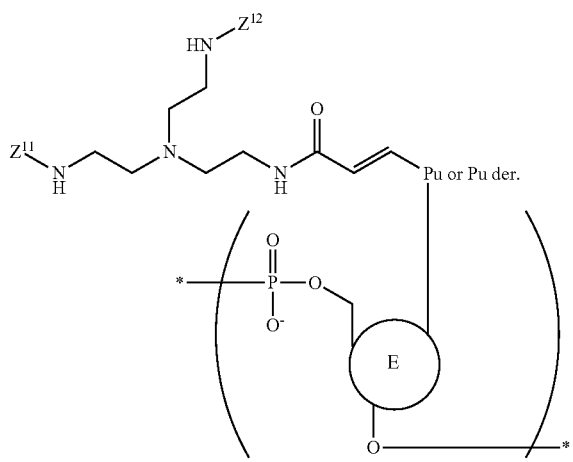

-continued (14-2)

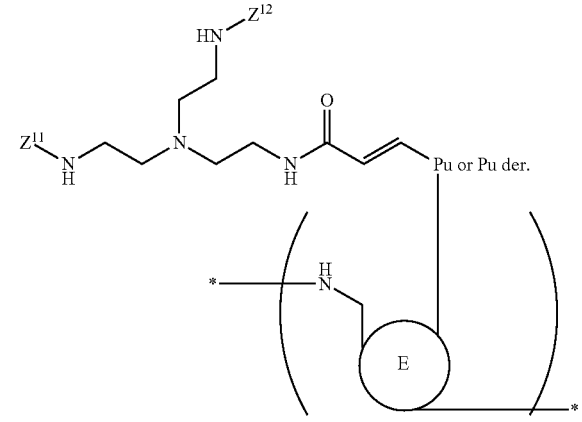

where in the formulae (13-1) and (14-1),
E, $Z^{11}$, and $Z^{12}$ are the same as in the formula (16);
in the formula (13-2) and (14-2),
E, $Z^{11}$, and $Z^{12}$ are the same as in the formula (16b), and Py, Py der., Pu, and Pu der. are as defined in claim 14.

16. A labeling substance that emits fluorescence, with two planar chemical structures contained in one molecule, which exist not in the same plane but with a certain angle formed therebetween, being located so as to be arranged in the same plane when the molecule undergoes intercalation into or groove binding to a nucleic acid,
wherein the labeling substance is formed of at least two dye molecule groups that do not exhibit fluorescence emission due to the exciton effect obtained when the at least two dye molecules aggregate in parallel to each other but exhibit fluorescence emission with the aggregation state being resolved when the molecules undergo intercalation into or groove binding to a nucleic acid;
wherein the labeling substance is:
the nucleic acid according to claim 1, where $Z^{11}$ and $Z^{12}$ each are an atomic group that exhibits fluorescence and exhibits an exciton effect;
a tautomer or stereoisomer of the nucleic acid;
or the salt of the nucleic acid, the tautomer, or the stereoisomer.

17. A complex labeling substance having, as a characteristic chemical structure, a chemical structure of at least two dye molecules contained in one molecule, with the at least two dye molecules not exhibiting fluorescence emission due to the exciton effect obtained when the at least two dye molecules aggregate in parallel to each other but exhibiting fluorescence emission with the aggregation state being resolved when the molecules undergo intercalation into or groove binding to a nucleic acid, the complex labeling substance optionally having a structure in which the at least two dye molecules are bonded to a linker molecule bonded to a nucleic acid to be labeled, with an additional linker molecule being interposed therebetween so as to have a branched structure, or are bonded directly thereto with no additional linker molecule being interposed there between,
wherein optionally the dye molecules each are the molecule described in claim 16.

18. A labeling substance selected from labeled mononucleotide, labeled oligonucleotide, a labeled nucleic acid, and a labeled nucleic acid analog, wherein the labeling substance is labeled with:
the labeling substance according to claim 16;
optionally with a linker molecule bonded to a carbon atom in a 5-position of a pyrimidine nucleus or a carbon atom in an 8-position of a purine nucleus of at least one base molecule contained in mononucleotide, oligonucleotide, nucleic acid, or a nucleic acid analog.

19. A method of detecting a nucleic acid, comprising:
carrying out nucleic acid synthesis using, as a substrate, the labeling substance according to claim 16 that is a labeled mononucleotide or labeled oligonucleotide, thereby synthesizing a double-stranded nucleic acid to which the atomic group that exhibits fluorescence or the dye molecule structure is bonded by intercalation or groove binding;
measuring a fluorescence intensity before and after the step of synthesizing the double-stranded nucleic acid; and
detecting the nucleic acid synthesis by comparing the fluorescence intensities to each other that are obtained before and after the step of synthesizing the double-stranded nucleic acid.

20. A method of detecting a nucleic acid, comprising:
carrying out nucleic acid synthesis by hybridizing, as a first nucleic acid, the labeling substance according to claim 18 that is a single-stranded nucleic acid to a second nucleic acid having a sequence complementary to the first nucleic acid or a sequence analogous to the complementary sequence, thereby synthesizing a double-stranded nucleic acid to which the atomic group that exhibits fluorescence or the dye molecule structure is bonded by intercalation or groove binding;
measuring fluorescence intensity before and after the step of synthesizing the double-stranded nucleic acid; and
detecting the hybridization between the first nucleic acid and the second nucleic acid by comparing the fluorescence intensities to each other that are obtained before and after the step of synthesizing the double-stranded nucleic acid.

21. A kit comprising:
a nucleic acid synthesis unit;
a labeling substance; and
a fluorescence intensity measurement unit,
wherein the labeling substance is the labeling substance according to claim 16.

* * * * *

SEQUENCE LISTING

<160> NUMBER OF SEQ ID NOS: 13

<210> SEQ ID NO 1
<211> LENGTH: 13
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (7)..(7)
<223> OTHER INFORMATION: n represents for modified pyrimidine

<400> SEQUENCE: 1
cgcaatntaa cgc                                                                13

<210> SEQ ID NO 2
<211> LENGTH: 13
<212> TYPE: DNA
<213> ORGANISM: Artificial
<220> FEATURE:
<223> OTHER INFORMATION: DNA oligomer

<400> SEQUENCE: 2
gcgttaaatt gcg                                                                13

<210> SEQ ID NO 3
<211> LENGTH: 13
<212> TYPE: DNA

```
<213> ORGANISM: Artificial
<220> FEATURE:
<223> OTHER INFORMATION: DNA oligomer
<220> FEATURE:
<221> NAME/KEY: misc_feature
<222> LOCATION: (7)..(8)
<223> OTHER INFORMATION: n represents for modified pyrimidine

<400> SEQUENCE: 3 tttttnntt ttt                                                          13

<210> SEQ ID NO 4
<211> LENGTH: 13
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (7)..(7)
<223> OTHER INFORMATION: n represents for modified pyrimidine

<400> SEQUENCE: 4
tttttntttt ttt                                                         13

<210> SEQ ID NO 5
<211> LENGTH: 13
<212> TYPE: DNA
<213> ORGANISM: Artificial
<220> FEATURE:
<223> OTHER INFORMATION: DNA oligomer

<400> SEQUENCE: 5
aaaaaaaaaa aaa                                                         13

<210> SEQ ID NO 6
<211> LENGTH: 20
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (11)..(11)
<223> OTHER INFORMATION: n represents for modified pyrimidine

<400> SEQUENCE: 6
tgaagggctt ntgaactctg                                                  20

<210> SEQ ID NO 7
<211> LENGTH: 20
<212> TYPE: DNA
<213> ORGANISM: Artificial
<220> FEATURE:
<223> OTHER INFORMATION: DNA oligomer

<400> SEQUENCE: 7
cagagttcaa aagcccttca                                                  20

<210> SEQ ID NO 8
<211> LENGTH: 13
<212> TYPE: DNA
```

```
<213> ORGANISM: Artificial
<220> FEATURE:
<223> OTHER INFORMATION: DNA oligomer
<220> FEATURE:
<221> NAME/KEY: misc_feature
<222> LOCATION: (7)..(8)
<223> OTHER INFORMATION: n represents for modified pyrimidine

<400> SEQUENCE: 8
cgcaatnnaa cgc                                                       13

<210> SEQ ID NO 9
<211> LENGTH: 28
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (8)..(8)
<223> OTHER INFORMATION: n represents for modified pyrimidine
<220> FEATURE:
<221> NAME/KEY: misc_feature
<222> LOCATION: (19)..(19)
<223> OTHER INFORMATION: n represents for modified pyrimidine

<400> SEQUENCE: 9
gcctcctnca gcaaatccna ccggcgtg                                       28

<210> SEQ ID NO 10
<211> LENGTH: 28
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (10)..(10)
<223> OTHER INFORMATION: n represents for modified pyrimidine
<220> FEATURE:
<221> NAME/KEY: misc_feature
<222> LOCATION: (19)..(19)
<223> OTHER INFORMATION: n represents for modified pyrimidine

<400> SEQUENCE: 10
cctcccaagn gctgggatna aaggcgtg                                       28

<210> SEQ ID NO 11
<211> LENGTH: 95
<212> TYPE: DNA
<213> ORGANISM: Artificial
<220> FEATURE:
<223> OTHER INFORMATION: DNA fragment

<400> SEQUENCE: 11
gccggtagtg gtggcgcacg ccggtaggat ttgctgaagg aggcagaggc aggaggatca    60
cgagttcgag gccagcctgg gctacacatt ttttt                               95
```

-continued

```
<210> SEQ ID NO 12
<211> LENGTH: 95
<212> TYPE: DNA
<213> ORGANISM: Artificial
<220> FEATURE:
<223> OTHER INFORMATION: DNA fragment

<400> SEQUENCE: 12
gccgggcatg gtggcgcacg cctttaatcc cagcacttgg gaggcagagg caggcggatt      60
tctgagttcg aggccagcct ggtctacaga gtgag                                 95

<210> SEQ ID NO 13
<211> LENGTH: 49
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (25)..(25)
<223> OTHER INFORMATION: n represents for modified pyrimidine

<400> SEQUENCE: 13
tttttttttt tttttttttt ttttnttttt tttttttttt ttttttttt                  49
```